United States Patent
Vigneault et al.

(10) Patent No.: US 11,795,434 B2
(45) Date of Patent: Oct. 24, 2023

(54) ENGINEERED STEM CELLS AND CELLULAR PRODUCTS PRODUCED AND SECRETED BY SUCH CELLS, METHODS OF PREPARING, AND USES THEREOF

(71) Applicants: Ottawa Heart Institute Research Corporation, Ottawa (CA); L'Institut de Cardiologie de Montréal, Montréal (CA)

(72) Inventors: Patrick Vigneault, Montreal (CA); Darryl Davis, Ottawa (CA); Stanley Nattel, Montréal (CA); Sandrine Parent, Ottawa (CA)

(73) Assignees: Ottawa Heart Institute Research Corporation, Ottawa (CA); L'Institut de Cardiologie de Montréal, Montréal (CA)

( * ) Notice: Subject to any disclaimer, the term of this patent is extended or adjusted under 35 U.S.C. 154(b) by 679 days.

(21) Appl. No.: 16/678,856

(22) Filed: Nov. 8, 2019

(65) Prior Publication Data

US 2020/0172871 A1 Jun. 4, 2020

Related U.S. Application Data

(60) Provisional application No. 62/758,160, filed on Nov. 9, 2018.

(51) Int. Cl.
| | |
|---|---|
| C12N 5/0775 | (2010.01) |
| A61K 35/34 | (2015.01) |
| A61K 35/12 | (2015.01) |
| A61P 9/00 | (2006.01) |
| C12P 1/00 | (2006.01) |
| C12N 15/86 | (2006.01) |

(52) U.S. Cl.
CPC ............ *C12N 5/0662* (2013.01); *A61K 35/12* (2013.01); *A61K 35/34* (2013.01); *A61P 9/00* (2018.01); *C12N 15/86* (2013.01); *C12P 1/00* (2013.01); *C12N 2510/00* (2013.01); *C12N 2740/15043* (2013.01)

(58) Field of Classification Search
CPC . C12N 5/0657; C12N 5/0662; C12N 2510/00
See application file for complete search history.

(56) References Cited

PUBLICATIONS

Liebau et al. "An Inducible Expression System of the Calcium-Activated Potassium Channel 4 to Study the Differential Impact on Embryonic StemCells" Stem Cells International vol. 2011, Article ID 456815, 12 pages (Year: 2011).*
Shen et al. "Therapeutic benefits of CD90-negative cardiac stromal cells in rats with a 30-day chronic infarct" Cell Mol Med. Mar. 2018; 22(3): 1984-1991. Published online Jan. 17, 2018. doi: 10.1111/jcmm.13517 (Year: 2018).*
Zhao et al. "Overexpression of the medium-conductance calcium-activated potassium channel (SK4) and the HCN2 channel to generate a biological pacemaker" Molecular Medicine Reports 20: 3406-3414, 2019 (Year: 2019).*
Uniprot Names & Taxonomy "Intermediate conductance calcium-activated potassium channel protein 4" accessed Sep. 22, 2022, 1 page (Year: 2022).*
Angelini et al., Foetal bovine serum-derived exosomes affect yield and phenotype of human cardiac progenitor cell culture, BioImpacts, 2016, 6(1), pp. 15-24.
Oualid Ayad et al., Functional BKCa channel in human resident cardiac stem cells expressing W8B2, The Febs Journal, 2018, pp. 518-530.
Xiaowen Bai et al., Electrophysiological properties of human adipose tissue-derived stem cells, the American Physiological Society, 2007, pp. C1539-C1550.
Henrike Berkefeld et al., Ca2+-Activated K+ Channels: From Protein Complexes to Function, the American Physiological Society, 2010, pp. 1437-1459.
Douglas J. Blackiston, Bioelectric controls of cell proliferation: Ion channels, membrane voltage and the cell cycle, NIH Public Access Author Manuscript, 2009, 24 pages.
Daniel Burkhoff et al., Assessment of systolic and diastolic ventricular properties via pressure-volume analysis: a guide for clinical, translational, and basic researchers, the American Physiological Society, 2005, pp. H501-H512.
Ke Cheng, PhD, et al., Human Cardiosphere-Derived Cells From Advanced Heart Failure Patients Exhibit Augmented Functional Potency in Myocardial Repair, NIH Public Access Author Manuscript, 2014, 20 pages.
Ke Cheng, PhD, et al., Relative Roles of CD90 and c-Kit to the Regenerative Efficacy of Cardiosphere-Derived Cells in Humans and in a Mouse Model of Myocardial Infarction, Journal of the American Heart Association, 2014, 10 pages.
L. Chilton et al., K+ currents regulate the resting membrane potential, proliferation, and contractile responses in ventricular fibroblasts and myofibroblasta, the American Physiological Society, 2005, pp. H2931-H2939.

(Continued)

*Primary Examiner* — Thane Underdahl
(74) *Attorney, Agent, or Firm* — Nyemaster Goode, P.C.

(57) ABSTRACT

There is disclosed a cardiac explant-derived stem cell (EDC), the cell comprising a gene encoding an intermediate-conductance $Ca^{2+}$-activated $K^+$ channel, and wherein the gene causes an overexpression of the intermediate-conductance $Ca^{2+}$-activated $K^+$ channel, and methods of producing same. There is also disclosed a method of producing engineered EDCs having a modulated bioelectric property, the method comprising: obtaining EDCs; introducing a KCNN4 gene into the EDCs to increase the expression of KCa3.1 channels, to produce engineered EDCs. There is also disclosed a composition for treating or ameliorating a damaged myocardium in a subject, the composition comprising extracellular vesicles isolated from cultures of engineered EDCs. There is also disclosed a method for treating or ameliorating a damaged myocardium in a subject, comprising administering the engineered EDCs or the extracellular vesicles isolated from cultures of engineered EDCs to the damaged myocardium of the subject.

19 Claims, 29 Drawing Sheets

Specification includes a Sequence Listing.

(56) References Cited

PUBLICATIONS

Jae Hyung Cho, MD, et al., Delayed Repolarization Underlies Ventricular Arrhythmias in Rats with Heart Failure and Preserved Ejection Fraction, HHS Public Access Author manuscript, 2017, 30 pages.

Darryl R Davis, et al., Isolation and expansion of functionally-competent cardiac progenitor cells directly from heart biopsies, NIH Public Access Author Manuscript, 2010, 20 pages.

Anke Diehlmann, et al., KATP channels in mesenchymal stromal stem cells: Strong up-regulation of Kir6.2 subunits upon osteogenic differentiation, Tissue and Cell, 2011, pp. 331-336.

Sung Hyun Choi et al., Direct Comparison of Distinct Cardiomyogenic Induction Methodologies in Human Cardiac-Derived c-Kit Positive Progenitor Cells, Tissue Engineering and Regenerative Medicine, vol. 9, No. 6, 2012, pp. 311-319.

S. Mark Duffy, PhD et al., The K+ channel iKca1 potentiates Ca2+ influx and degranulation in human lung mast cells, American Academy of Allergy, Asthma and Immunology, vol. 114, 2004, pp. 66-72.

Sanjiv Ghanshani et al., Up-regulation of the IKCa1 Potassium Channel during T-cell Activation, The Journal of Biological Chemistry, vol. 275, No. 47, 2000, pp. 37137-37149.

Lilian Grigorian-Shamagian et al., Cardiac and systemic rejuvenation after cardiosphere-derived cell therapy in senescent rats, European Society of Cardiology, Aug. 14, 2017, pp. 2957-2967.

Maxime Gueguinou et al., KCa and Ca2+ channels: The complex thought, Biochimica et Biophysica Acta, 2014, pp. 2322-2333.

Valerie Hinard et al., Initiation of human myoblast differentiation via dephosphorylation of Kir2.1 K+ channels at tyrosine 242, Research Article—Development 135, 2008, pp. 859-867.

Robyn Jackson et al., Paracrine Engineering of Human Cardiac Stem Cells With Insulin-Like Growth Factor 1 Enhances Myocardial Repair, Journal of the American Heart Association, 2015, 12 pages.

Robyn Jackson et al., Isolation of human explant derived cardiac stem cells from cryopreserved heart tissue, Plos One, 2017, 14 pages.

Alexander Kleger, MD PhD et al., Modulation of Calcium-Activated Potassium Channels Induces Cardiogenesis of Pluripotent Stem Cells and Enrichment of Pacemaker-Like Cells, http://ahajournals.org, 2010, pp. 1823-1836.

Alexander Kleger et al., Calcium-Activated Potassium Channels, Cardiogenesis of Pluripotent Stem Cells, and Enrichment of Pacemaker-Like Cells, TCM vol. 21, Nov. 3, 2011, pp. 74-83.

Stephane Konig et al., Membrane Hyperpolarization Triggers Myogenin and Myocyte Enhancer Factor-2 Expression during Human Myoblast Differentiation, The Journal of Biological Chemistry, vol. 279, No. 27, Issue of Jul. 2, 2004, pp. 28187-28196.

Nicholas Latham et al., Human Blood and Cardiac Stem Cells Synergize to Enhance Cardiac Repair When Cotransplanted Into Ischemic Myocardium, CIHR Author Manuscript, 2013, 16 pages.

Michael Levin, Molecular bioelectricity: how endogenous voltage potentials control cell behavior and instruct pattern regulation in vivo, MBoC Perspective, vol. 25, Dec. 1, 2014, pp. 3835-3850.

Tao-Sheng Li et al., Expansion of human cardiac stem cells in physiological oxygen improves cell production efficiency and potency for myocardial repair, European Society of Cardiology, 2011, pp. 157-165.

Stefan Liebau et al., Formation of cellular projections in neural progenitor cells depends on SK3 channel activity, Journal of Neurochemistry, 2007, pp. 1338-1350.

Stefan Liebau et al., An Inducible Expression System of the Calcium-Activated Potassium Channel 4 to Study the Differential Impact on Embryonic StemCells, SAGE-Hindawi Access to Research Stem Cells International, vol. 2011, Article ID 456815, 12 pages.

Ryo Matsumoto et al., Vascular Endothelial Growth Factor-Expressing Mesenchymal Stem Cell Transplantation for the Treatment of Acute Myocardial Infarction, Arterioscler Thromb Vasc Biol. available at http://www.atvgaha.org, 2005, pp. 1168-1173.

Audrey E. Mayfield et al., The effect of encapsulation of cardiac stem cells within matrix-enriched hydrogel capsules on cell survival, post-ischemic cell retention and cardiac function, CIHR Author Manuscript, 2014, 19 pages.

Audrey E. Mayfield et al., The impact of patient co-morbidities on the regenerative capacity of cardiac explant-derived stem cells. Stem Cell Research & Therapy, 2016, 7 pages.

Audrey E. Mayfield et al., Interleukin-6 Mediates Post-Infarct Repair by Cardiac Explant-Derived Stem Cells, Theranostics, vol. 7, Issue 19, 2017, pp. 4850-4861.

Lisa McGinley et al., Lentiviral vector mediated modification of mesenchymal stem cells & enhanced survival in an in vitro model of ischaemia, Stem Cell Research & Therapy, 2011, 18 pages.

Kelly A. McLaughlin et al.. Bioelectric Signaling in Regeneration: Mechanisms of Ionic Controls of Growth and Form, HHS Public Access Author Manuscript, 2018, 33 pages.

Martin Muller et al., Ca2+ Activated K Channels—New Tools to Induce Cardiac Commitment from Pluripotent Stem Cells in Mice and Men, Stem Cell Rev and Rep, vol. 8, 2012, pp. 720-740.

James R. Munoz et al., Human stem/progenitor cells from bone marrow promote neurogenesis of endogenous neural stem cells in the hippocampus of mice, PNAS, vol. 102, No. 50, Dec. 13, 2005, pp. 18171-18176.

Sze-Ying Ng et al., Role of Voltage-Gated Potassium Channels in the Fate Determination of Embryonic Stem Cells, Journal of Cellular Physiology, vol. 224, 2010, pp. 165-177.

Atricia K. Nguyen, MD, et al., Adult stem cell therapy and heart failure, 2000 to 2016: a systematic review, HHS Public Access Author Manuscript, Oct. 2016, 17 pages.

Xiao-Yan Qi et al., Fibroblast Inward-Rectifier Potassium Current Upregulation in Profibrillatory Atrial Remodeling, Cellular Biology available at http://circres.ahajournals.org, 2015, pp. 836-845.

Heidi Reich, MD et al., Repeated transplantation of allogeneic cardiosphere-derived cells boosts therapeutic benefits without immune sensitization in a rat model of myocardial infarction, The Journal of Heart and Lung Transplantation, 2016, pp. 1348-1357.

Thomas E. Robey et al., Systems Approaches to Preventing Transplanted Cell Death in Cardiac Repair, NIH Public Access Author Manuscript, 2008, 27 pages.

Ane M. Salvador et al., Intercellular Adhesion Molecule 1 Regulates Left Ventricular Leukocyte Infiltration, Cardiac Remodeling, and Function in Pressure Overload-Induced Heart Failure, Journal of the American Heart Association, 2016, 18 pages.

Gianluigi Savarese et al., Global Public Health Burden of Heart Failure, Radcliffe Cardiology available at www.CFRjournal.com, 2017, pp. 7-11.

Deliang Shen et al., Therapeutic benefits of CD90-negative cardiac stromal cells in rats with a 30-day chronic infarct, Journal of Cellular Molecular Medicine, vol. 22, No. 3, 2018, pp. 1984-1991.

Baskar Subramani et al., Generation and characterization of human cardiac resident and non-resident mesenchymal stem cell, Cytotechnology, vol. 68, 2016, pp. 2061-2073.

Sarah Sundelacruz et al., Membrane Potential Controls Adipogenic and Osteogenic Differentiation of Mesenchymal Stem Cells, PLoS ONE, vol. 3, Issue 11, Nov. 2008, 15 pages.

Sarah Sundelacruz et al., Role of Membrane Potential in the Regulation of Cell Proliferation and Differentiation, Stem Cell Rev and Rep, vol. 4, 2009, pp. 231-246.

Sarah Sundelacruz, PhD et al., Depolarization Alters Phenotype, Maintains Plasticity of Predifferentiated Mesenchymal Stem Cells, Tissue Engineering, Part A, vol. 19, Nos. 17 and 18, 2013, pp. 1889-1908.

Xian-Liang Tang, MD et al., Intracoronary Administration Of Cardiac Progenitor Cells Alleviates Left Ventricular Dysfunction In Rats With A 30-Day Old Infraction, NIH Public Access Author Manuscript, 2010, 25 pages.

Rong Tao et al., Functional ion channels in mouse bone marrow mesenchymal stem cells, Am J Physiol Cell Physiol 293, 2007, pp. C1561-C1567.

(56) References Cited

PUBLICATIONS

Everad L. Tilokee et al., Paracrine Engineering of Human Explant-Derived Cardiac Stem Cells to Over-Express Stromal-Cell Derived Factor 1a Enhances Myocardial Repair, Stem Cells, vol. 34, 2016, pp. 1826-1835.
Patrick Vigneault et al., Calcium-dependent potassium channels control proliferation of cardiac progenitor cells and bone marrow-derived mesenchymal stem cells, The Journal of Physiology, 2018, pp. 2359-2379.
Patrick Van Vliet et al., Hyperpolarization Induces Differentiation in Human Cardiomyocyte Progenitor Cells, Stem Dell Rev and Rep, vol. 6, 2010, pp. 178-185.
Kai Wang et al., Electrophysiological Properties of Pluripotent Human and Mouse Embryonic Stem Cells, Stem Cells, vol. 23, 2005, pp. 1526-1534.
Jun Wu et al., Infarct stabilization and cardiac repair with a VEGF-conjugated, injectable hydrogel, Biomaterials, vol. 32, 2011, pp. 579-586.
Qiuling Xiang et al., ISL1 overexpression enhances the survival of transplanted human mesenchymal stem cells in a murine myocardial infarction model, Stem Cell Research & Therapy, 2018, 15 pages.
Mi-Hyeon You et al., Voltage-gated K+ channels in adipogenic differentiation of bone marrow-derived human mesenchymal stem cells, Acta Pharmacologica Sinica, vol. 34, 2013, pp. 129-136.
Shan Ping Yu et al., Preconditioning Strategy in Stem Cell Transplantation Therapy, NIH Public Access Author Manuscript, 2013, 22 pages.
Ying-Ying Zhang et al., Characterization of functional ion channels in human cardiac c-kit+ progenitor cells, Basic Res Cardiol, Apr. 2, 2014, 14 pages.

* cited by examiner

FIGURE 2A
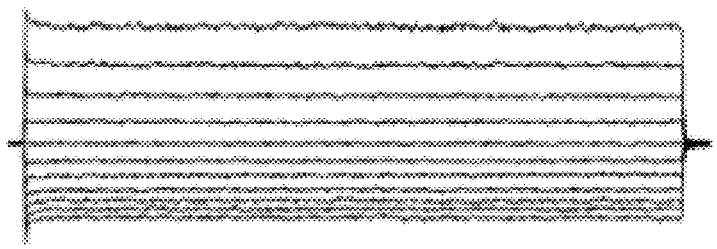
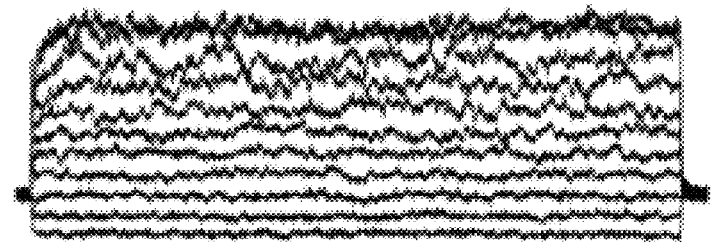

FIGURE 2C
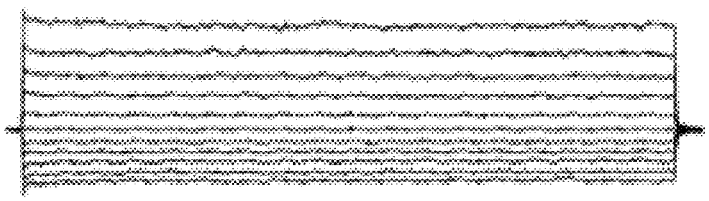
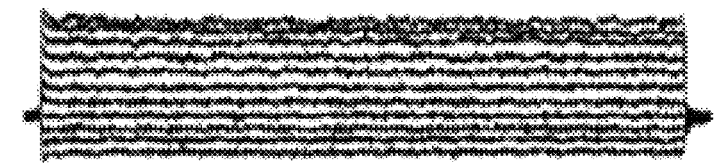

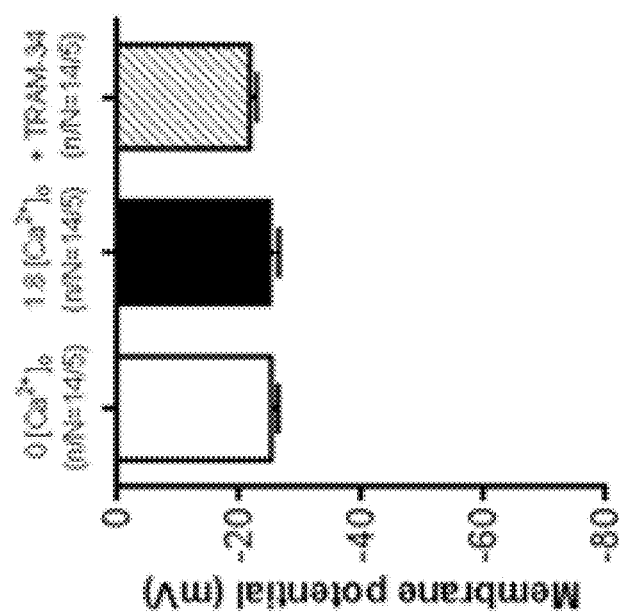
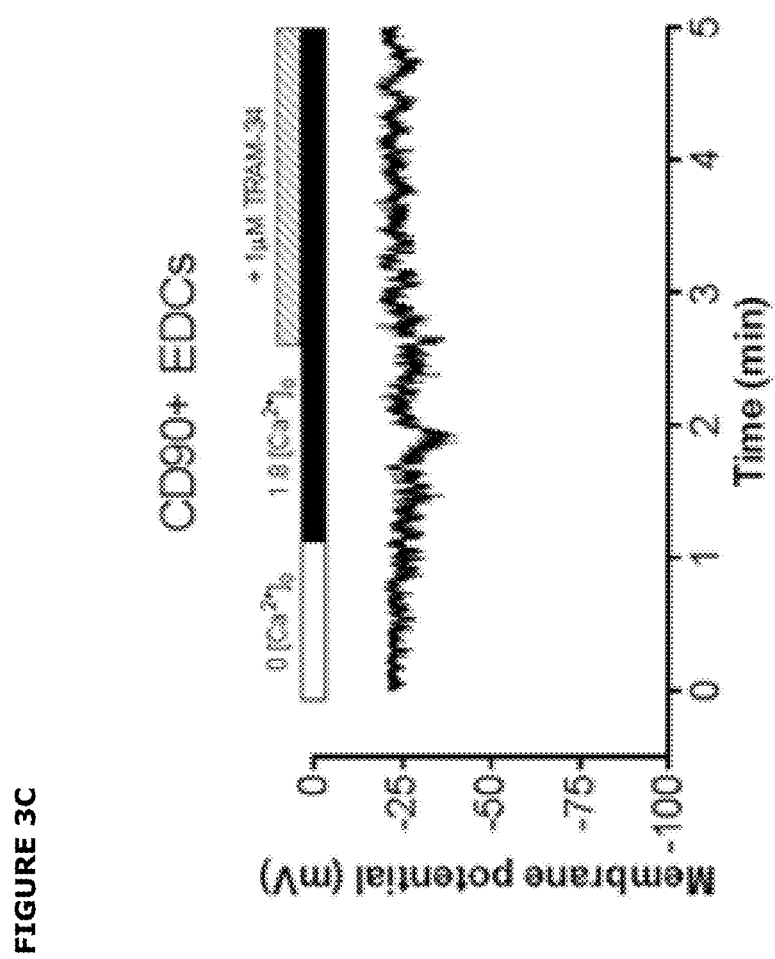
FIGURE 3C

FIG. 5A
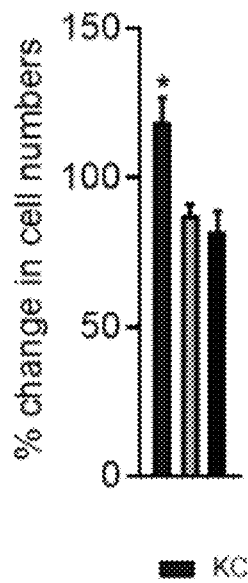
FIG. 5B
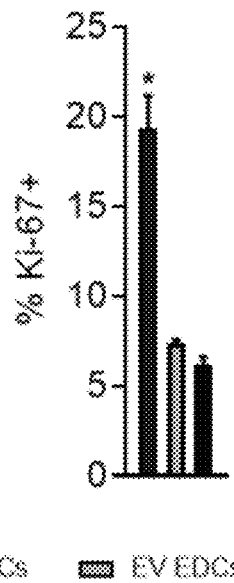
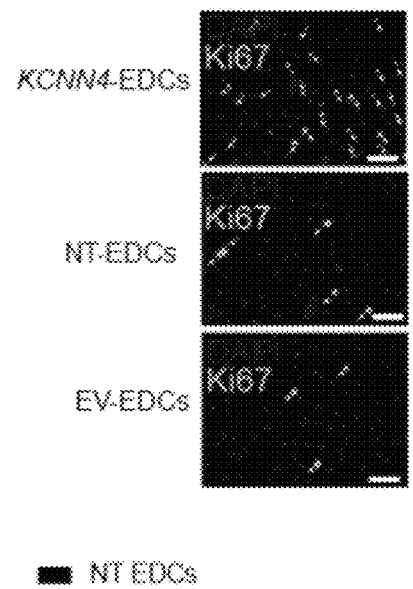
FIG. 5C
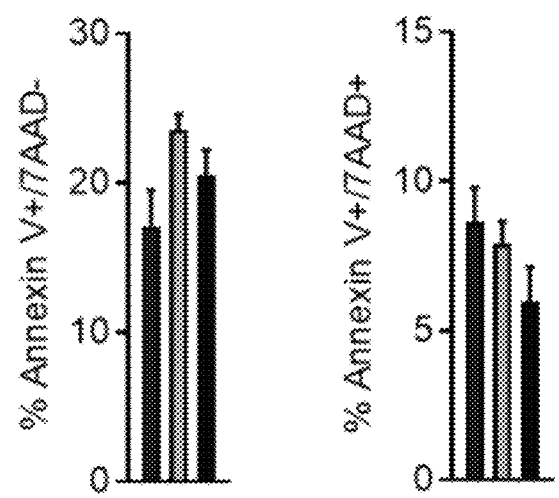

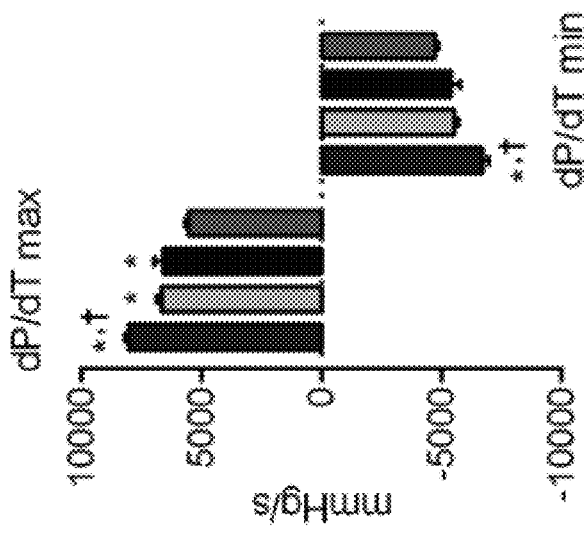
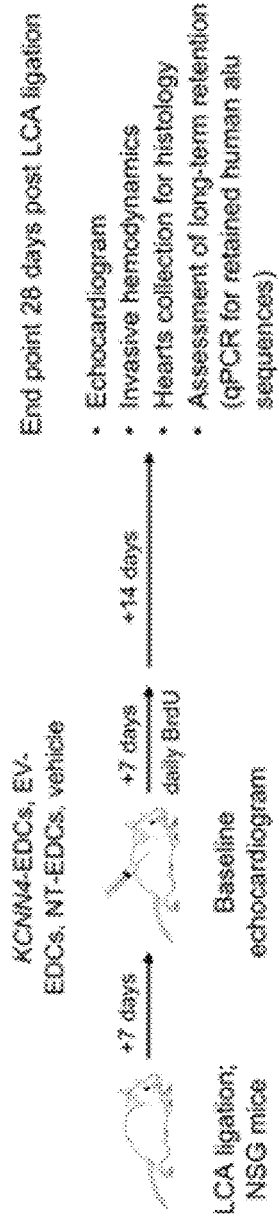
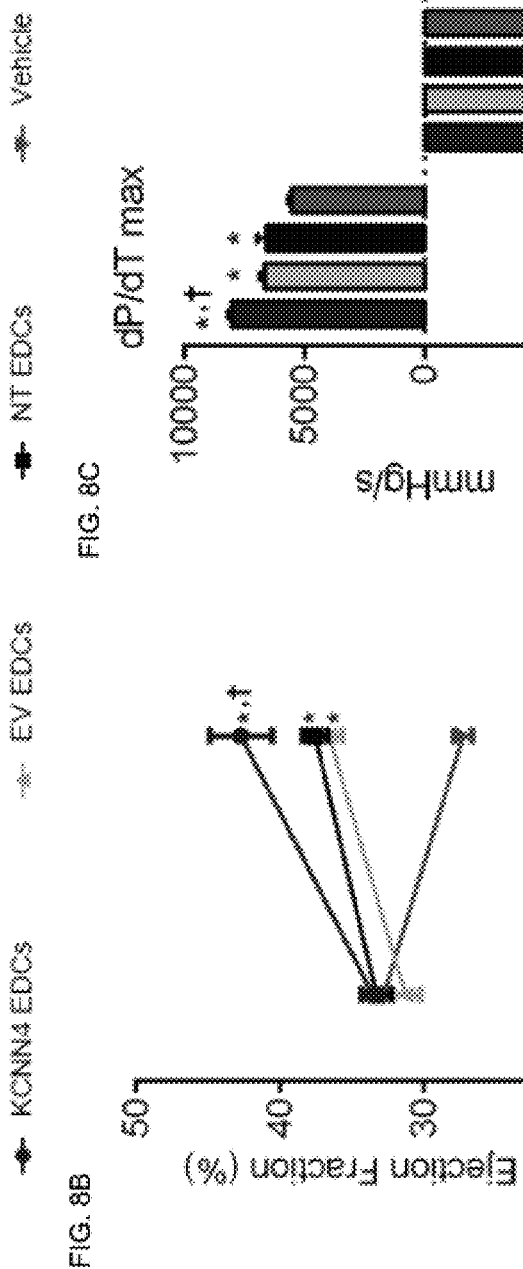
FIG. 8A
FIG. 8B
FIG. 8C

■ KCNN4 EDCs ▨ EV EDCs ■ NT EDCs ▨ Vehicle
FIG. 10A
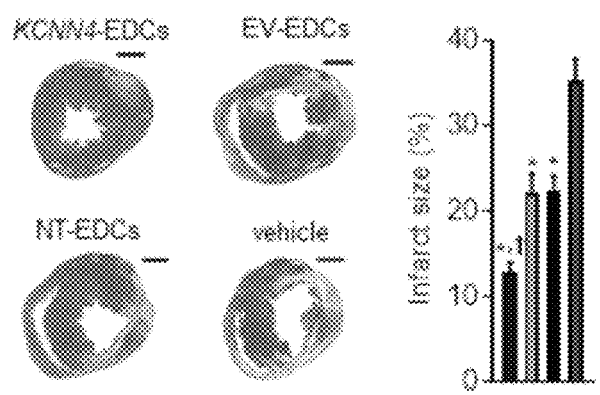
FIG. 10B
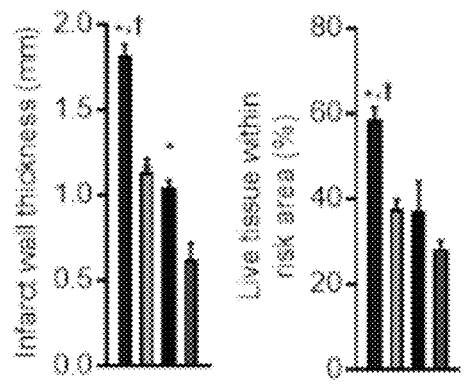
FIG. 10C
FIG. 10D
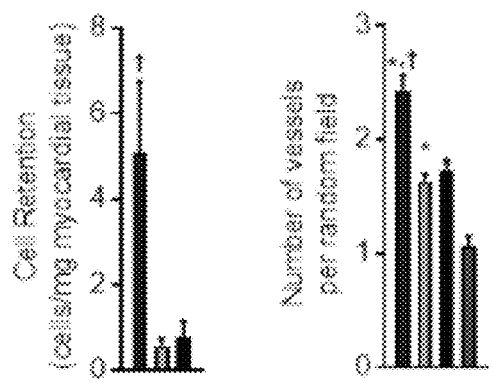
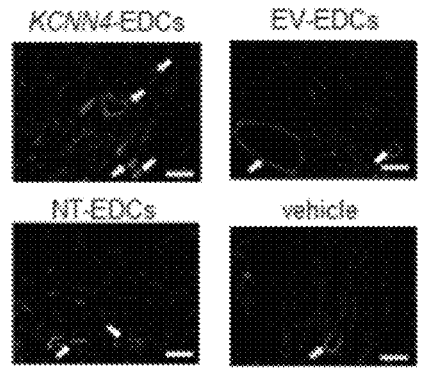
FIG. 10E
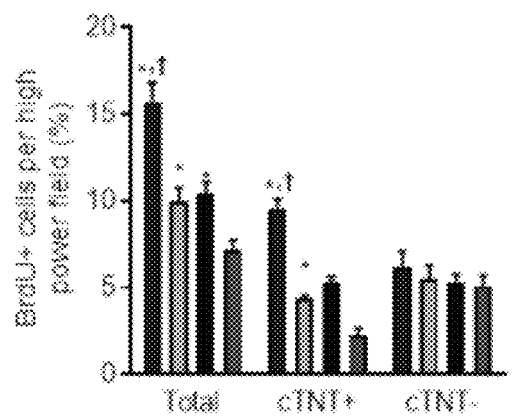
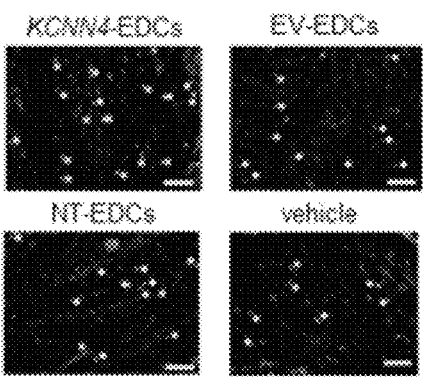

FIGURE 13A
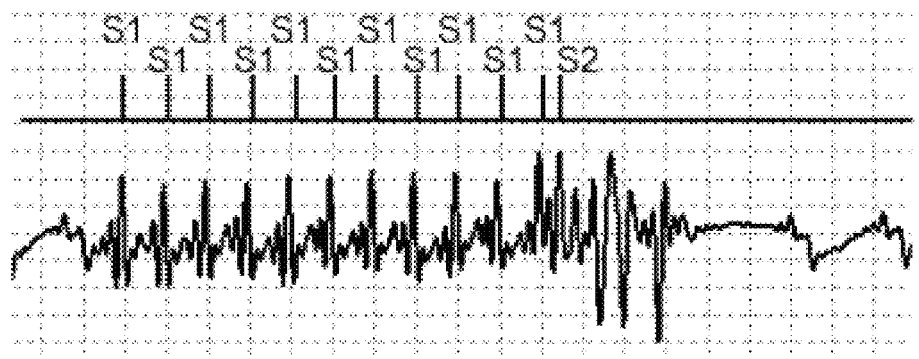
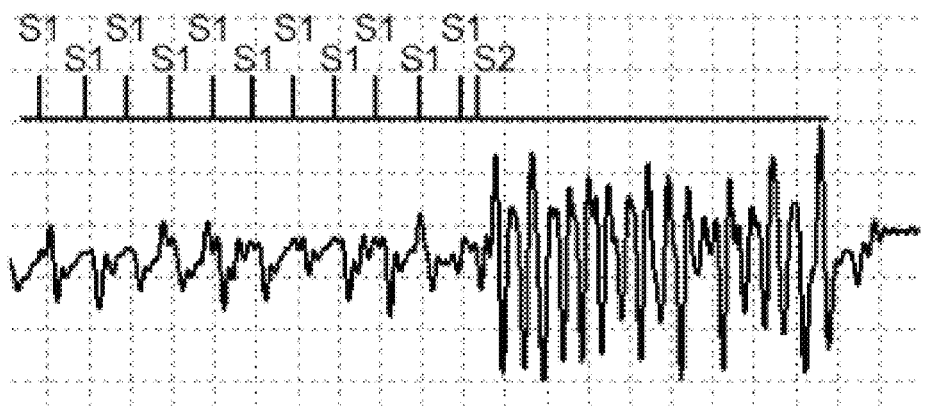
FIGURE 13B
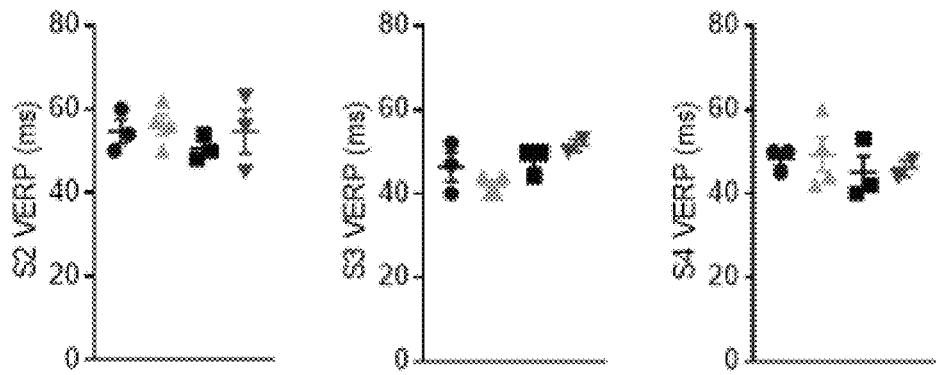

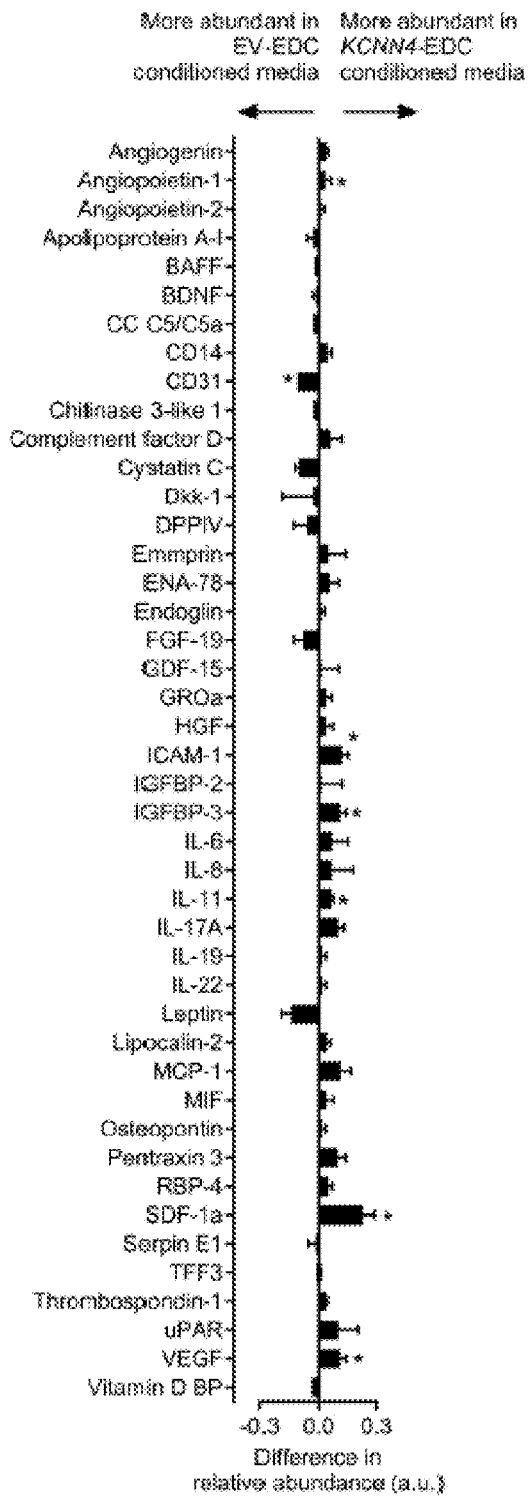
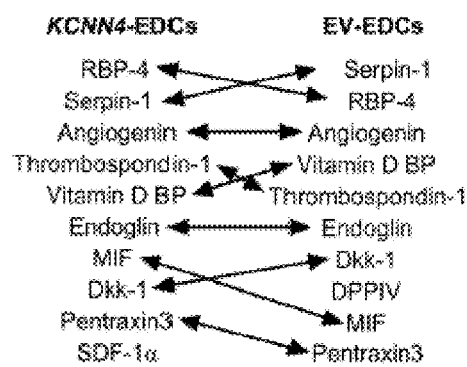
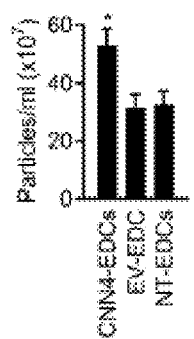
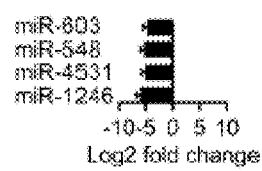
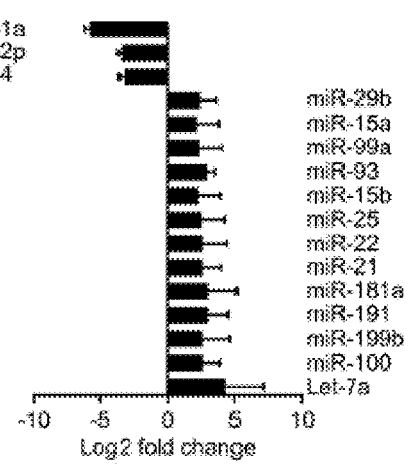

KCNN4 EDCs vs. EV EDCs
Upregulated

SEQUENCE LISTING

```
<160> NUMBER OF SEQ ID NOS: 3

<210> SEQ ID NO 1
<211> LENGTH: 22607
<212> TYPE: DNA
<213> ORGANISM: Homo sapiens

<400> SEQUENCE: 1
tcacatggtt gcattctgtt aggacaggac tggggcttta gccaagatag cttcattctc      60
cctgcatggc ctctccatgt gactagcttg ggcttcctta cagcatggtg gtcttctagt     120
tctaagggta caaaagcaga agcttctagt ttccttaaca tctggacctg gaactggttc     180
agtgtcatat ttgccacatt ctattagtca aagcaagtca tgagccagat agactgaagg     240
agaaggaaca tactgttcct tttcgtggga gaagccacct gccagtgcag ggaagggagg     300
agtcactggc aggcaacttg ggagacaatg tatcacaaga ctttaacata gaccaggcct     360
gctgttaggg ctccagacat tctctctcac ctaagcctca agcagccctg tcacatgga      420 aacataatcc ctcttttaca agtttcacag agcacacaac tatggatggc aactaggttt     480
gaactcaggt ttgtctctaa accaggctgt acgtataaca tattccatac aaaaataaag     540
ttaggccggg ggtggtgtct catccctcta atctcagccc tttgggaggc tgaggcaggt     600
ggatcatctg aggtcagaag ttcaagatca gcctggctag catggtgaaa ccccgtctct     660
actaaaaata ccaaaattag cctggtgtgg tggtgcatgc ctgtagtacc agctacttgg     720
gagtctgagg caggagaatc gcttgcatcc aggaggtgga ggttgcagtg agccaagatc     780
```

```
gtgccactgc actccagcct gggtgacaga gcgagactct gtcttgaatg aatgaatgaa    840
tgaatgaata aagtcagtgg tcacatcgag gcttaaaccg aggtctctag acttccatat    900
tgtgagatat agatatctgt atatcatata catctgtata cactatacat ctgtatacta    960
tgccatatac tatactacat atctgcatat actatatata gagtgtgggt gtatgtctct   1020
gtgtaataac ataatataca tacatttta  actggcgggg aacacagaga tacaaagaag   1080
aaaataaaag cagaaatgaa gaaaaaagga gaaggagaa  aagcatgcac ttggagacta   1140
agaccaggag atagaaacag agaagcaaga caaggcgcag tggctcacac ttgtaattcc   1200
agcaccttag gaggacgagg caggaggatg gcttgagacc aggagttcgc gaccagcctg   1260
gcaacatagt gggaactgat tttatgacca aaaaaatgtt tttaattaa  aaagagagag   1320 agaagagaaa gaaagaaaga aaagaaaaaa gaaagagaga gagaaagaag aaagaaagaa   1380
aaagagaaag aaagaaaaaa caaggacaat gatatacaga gagaaaaatg aagactgaga   1440
gcaaagaaga gactgagatt gatggaatca cgaggtctcc ctcctttagc ctggaaactc   1500
cacaagagca agaattttgt ccatttttgt tcattacata tcgccaactc cttgagcagt   1560
gcctggcact cagtaggtgt tttgctctat gttggcaaga aaccaggctg acagggaga   1620 gtgtctgcag ttgcctaagt gaacactagg tgacagtatt tataagccct ggagcttcca   1680
ggctccaagg tcccagagat ggcggtggag gatttgccgc cactgacctc tgactttcag   1740
gatctcttcc tcggggctca gccctgcctt tccctgcaca agccttgggc gatgaatgac   1800 cttccgcct  gagacaccct cttcactctc cttccaccagc ctgcccagtt aaacaactct   1860
ttgtccctgg ccccttcctg ctgggccccg aggcacctgg gttcttttcca ggcccggaga   1920 tggggctgcg acagaggtgg tgcagctggg acaaggccaa ggaaaaatcc tggagactct   1980
ggaatcagtt cttccagtgt atgagaccca gcccctcctc cctcagaccc aggggtccag   2040 acccccagcac ctcctccctc agaccagcag tccaggcccc agcctcctc  cctcagactc   2100 aggagtccag accccagatc ctcctccttc agacccagga gtccaggcct cagcccctcc   2160
tccctcagac ctaggagtcc agatccagcc cctcctctct cagaccagca gtctagaccc   2220
cagcccccct cctccctcag aaccaggagt ccagaccccc tgcccctcct ctctcagacc   2280
agcagtccag accccatccc ctccttcctc agacccagga gtccagaccc cagcccctcc   2340
tccctcagac cccctcctcc ctcagaacca ggagtccaga ccccagctt  cttcctcctg   2400 gaccttcct  cttaggcatt tgaggtcct  ctactattcc ctctccctct cttttacaca   2460 aaccctctc  tccctccact ccccattcta ggattgagac caagggtgag tcacaagaag   2520
ccctgaggcc ctgagtcacc tcgccctccc cccttggccc ctccctgggc tggaggcagc   2580
tggctgagga gtgaagcagt ttcctaggac tgaccctgc  atcccaggac tgcagtttga   2640
aggcaggtgc ccttcccact gtaacccat  cactgccacc caggcatgtc catgcccatc   2700
ctttgctgtt tttctctttc agtcatggcc tatttggaga caaaatttct ctgtgctcta   2760
acttccgtgt cttgattgtg ttttccggtt tctctgcacc tgtgggtctc tttgattttt   2820
tttaatacat gccccacca  tccctggctg aatgcctcga ggtctctctg attatctctc   2880
tctccctctg tgtcagtctc tgtctccgtt tttcacaagt gcctgaactg ggcacagat    2940 gccatggcat ggccgcagct ggagcgctat ttagtggctt ctgacccttg ggtggccaca   3000
gtctctggat cactggccct caaccccctga gtgggactgg ggtagaaccg gaaggaacca   3060
ggctgtccgt agatgtgcca gtgaacagca gagagaaact gaggcagaga caagcataga   3120
gaggcccgga gagagagaga gagacccaag aggagaccag gaggcaggga gagagtgaaa   3180
```

-continued

```
cagagacgga gagaaacacc gattcagcaa gagacagaca aaaacagagg gccctagaga      3240
cggagagatg gagacagagt gagacacgat gacagagaca caggcaatga tgaacacaga      3300
gagagacatg acagagagac agtgacgggg aagaaggaa acagaggagc agagagggac       3360
acgaagatgg agaaagggac agagcgatga gagagacaca gagaggctaa gagaggcaga     3420
gacagagaga cagagtgaag agagacagag agagacaaag gtaccaggag agaagaacag     3480
agacagagat aaagacaaac ctggccaggc acggtggctt acgcctgtaa tcccagaact     3540
ttgggaggcc gaggcgggtg gatcacctga ggtcagaagt tcacgaccag cctggccaac     3600
atggtgaaac ctcgtctcta ctaaaaatac gaaaattagc tgggtgtggt ggtgcacacc     3660
tgtaatatca gctactcggg aggttgaggt aggagaattg cttgaacctg ggaggtggag     3720
gttgcagtga gccgagatcg tgccactgca ctccagccat gggagacaga gcaagactct     3780
atctcaaaaa aaaaaaaaaa aaaaaaaag acaaacgcgg aggtttccag atcaggagag      3840
actgagacag gaagcaagtc ccaaagaacc agagaaagag ccggagaggg aggagagaga     3900
cgcagcgagc cgggcggcca gtgggcaggg gtgcccaggc tgcaggctca ggagtgcccg     3960
gcggctgcac tttccccaag tggacgcatg tgtggtgtct gggcgcgccc gggtgtgtct     4020
ccagccctct cccgccaagt ctcgccgagt gggtaattgt gtgtgccgag gggcggagcc     4080
cccgcaaggg ttgtgttttt gccactgggc gtgtccatgt gtatggtttg gtgtctctgg     4140
gtgtgtttgt gtgggctgcc ttggtgtgca gtcagacatg tctgtgcgtg tctcgcttcc     4200
ctggggctgg tgggtccagg gtcccacacg acctaggaca caaggagggg agggttgtg     4260 tccgcaggtt ccttgcagag gggtgtgcat gaggccaagg gcagtgtcac cagttcagtg     4320
catgatgctg ggaggtgatg tgcgtcacca ggtcagtgca tgcctgtgtg tctccacagg     4380
agggtttgat ctgtgtcgga gcgtatggtg tacagatcca tgagtggctc gtgctgcgac     4440
acatggagat gtcctatgtt gtgtgttgct ctgagagtca ccgtgcacat tccacactgg     4500
catttgctgt atctcacgtc agggtccatg tccctgttgg gggcctcttc cttctcagcc     4560
cccagcaccc accctgagtg ccaaccaccc caagtgtctt gtgtttgtgt agctgtgtgt     4620
tatgttgtgt cagaggatac accccccctcc cccgatgctg gtgttgtgtg ggtggcggta     4680
gacctcagtg tcagtagtat cagtgagtgg tgacatctgg tgttttatgg gacatgtggt    4740
cgtttgtgga aggttgggtg tgttggaaaa cattgtgttt atgtgttttg cgttactgtg     4800
tgctggtgta ttactccgcg tatgttgttg tgtggccacg catgttggaa tataacgtgt     4860
tgggttgtgt ggaggtattg tatgtcatgt ttgggtgtgg ctcatggctc agaggtgatg     4920
gtgtatgttg cgtttgtttt tttgttttg cttgttttag agataggatc ttgctatgtt     4980
gcccaggctg gtctcaaacc cctgggctcc agcaatcctc ccacctcaac ctcccaaact    5040
gctgggatta caggcatgag ccactgcacc cagccgtatg ttgcatttgg gcactggggt    5100
ctatgaaggt ccaaccccat ccccttcccc cagggcatca tcctggatgt tgtcctgtgt    5160
ggccagaata taccagaatc atcttgcttc aggcatgtgc ttcttgggtt tctccgtgtg    5220
tcgctgtacc ttgtaggtct ctgcatgcat ccactcagct tgtcctctga ccatacattt    5280
gaatcgcacc acacatcaga gcatgctgaa tcagtgcgtg ttttgaatca tcactgcgag   5340
cacttgtgtt cgagtcaaca ggcgccacaa tgtatgtgca attctctagc tctgggtgat   5400
tgggggctac tataggtatg tccctaaatg ttgtgtgtct acacgtattg ggtttcgttc   5460
caagggtgtg tagtgtttag gaaactggga ctgcacagtg tttgtgtcgg tgtgtggtgt   5520
gtggcatcag ggcgtcacta ctttaatata tattgtgtgt ttgtgtaaca cctggtgtat  5580
```

```
gttgtgtttg tgtggccaca gttgtgcatc gtcctatttg tggtgtttgg gtgtggctct    5640
ttgtgtcaga gaaagttgtg acaactttga gtgtaatatt tgtgcctgtg tgtggacggt    5700
gtttgggtgg ctgtgtgtgc cacgggatac tgcctgcttg ctaagtgctg gtgtgtgtca    5760
caccatgtgt gtggtgtctg ggtgtggctg tgggtttcag agcttgctgg gagttgtgag    5820
tcactctgtg taggttgtgt tgtgtgccct ggtgtgttag tctccgtctt gggctgtgga    5880
gtgtccttcg gtgtctgggt gtggtgagta gaggtgtgtg tcacaaagta cagaccattg    5940
tgtgtgacaa agcccatcgt gtgtctgtgt gtgtctttat ccacgtggat ggacgtctct    6000
ttcttgctct gccccaagac acaccctagc ccctccttat tctcaaaagg gggagctggg    6060
gagcctcccc ctaccctggg gcctcccctg ccctccccg cctgcctgg ccgtcaccac    6120 tccccagagg gcacagggct ctgctgtgcc tcagagcaaa agtcccagag ccagcagagc    6180
aggctgacga cctgcaagcc acagtggctg ccctgtgcgt gctgcgaggt gggggaccct    6240
gggcaggaag ctggctgagc cccaagaccc cggggccat gggcggggat ctggtgcttg    6300
gcctgggggc cttgagacgc cgaaagcgct tgctggagca ggagaagtct ctggccggct    6360
gggcactggt gctggcagga actggcattg gactcatggt gctgcatgca gagatgctgt    6420
ggttcggggg gtgctcggtg agtggggcat ggtggctggg agctgggact cctaggtctg    6480
agggaggagg ggctgggggt caggactctt gggtctgagg gaggggggc tggggggtcag    6540 gactcctggg tctgagggag gaggggctga gggtcaggac tcctgggtct gagggaggag    6600
ggactgggga cttggactcc tgggtctgag ggaggaggga ctgagggcct ggactcctgg    6660
gtctgaggga ggaggggctg ggggtcagga ctcctgggtc tgaggaggga ggggctgggg    6720
tctggactcc tgggtctgag ggaggagggg ctgggggtca ggactcctgg atctgaggga    6780
ggagaggttg ggggcctaga ctcttgggtc tgagggagga ggggctttgg ctgggactcc    6840
tgggtgctcc caggagacag ttgctggggt ccttctctgc aaaaggaagg gaatatttgt    6900
ttcagtgttt cagtctttga agatgttgcc attagacggc cagaggtcca ggaccctgg    6960 aggccagagg gtggctgatc agacactcaa gcccccaag agccaataag gggagaggta    7020
gccccaggtt tggtgaaggg agagtggagg aaagacaaag ttcttccagt aggcggcagc    7080
tctttggtcc ttgtctaacc tctaatgttt acccagtgcc ttagatgcaa aggacagaaa    7140
aaactgcctt gggggtgggg atgggaaatg ggaaacaaac ctctcccccg acctgcctcc    7200
ccccaccaac cccaacccag tctccactgt taacaagctc aatttctccc caaatctgca    7260
tgctgattag tcagggaaat agtggagagg taggcttaca gtggcctgga ctcctaggta    7320
ccaggagagg aggggctgg gtcctggatt cctgagtctt aaggagaagg gggttttgat    7380
tgcttttggg gaagagggc tgactccgaa gatgagtggt gagtagggaa gaaaggggaa    7440
agtggggtca gggcaggtct cagcaggctc ccgtcacatt ccagccctgg tcaggccagt    7500 gatgggcag atcaaggaca agggttggaa taagtggctt gaggggagaa cagacttgct    7560
caacaggaaa ggaggggctg gagacctctc tggcagaagg gttgtggaac tgggctggta    7620
gggccagatg cggacactga tatgaagatt gggtagattc ctgagggtct gatgttccga    7680
cttggatctg gagggggtgg tggcagctc tgaagtgacc aggagccaca tggagggtca    7740
ggcatgcagc ttcctctggc aggcggcggg cactgagggg gtgggccgc gaagtccat    7800 gccaacagga agcatggccg gggcctgccc gccgctccca cgccgaagca ccgcacccag    7860
aagccgaggt gggaacacag tgaccctggc agatgggaag agacgggtc catcctaccc    7920 cacttcaccc ctctgctttc tcacccctca tttcttcctt ccctccacca tggccaggcc    7980
```

```
actgcctcta tcagtgggac cttggggaag ctgttacaac cctctgaacc tcagtttccc    8040
catctgtaaa ttggggtgag ggttaaaata catgaccta aggtcaccc tccacccttt     8100 ttattttatg tagagatggg accttgcttt gttgcctagg ctggtcttga actcctggac    8160
tcaggcaatc ctcctgcctc aaagtgctgg gattacaggc ctgagccaca gctcctcagt    8220 cccctttga ggactctctt aataacatcc accgcccctc accacctcca tctcaatcta    8280
atgagctcat ttctgcaaag gacccagaca cctgctcccc aggggagggg ctggcagag    8340 aggcaggtgc aaaaccctag ggagtccaag ggaactggat agagatatcc aaaagcacca    8400
ggtggggtgg aggaggaggg atggggagag gtacagagag agacagagac acagagatac    8460
atggagagaa aaagagagat ggagacaaaa atgcagaaag atagagaagt acagctaaag    8520
agaaagacaa atagggctat caagctactg agaaatccac cagtgagaga tacacacaca    8580
gcgttagaaa agacaataga gggccgggcg cggtggctca cgcctgtaat cccagcactt    8640
tgggaggccg aggtgggcgg atcacaaggt caggacatcg agaccatcct ggctaacaca    8700
gtgaaacccc atctctacta aaaacacaaa aaattagcca ggcatggcgg cgtgtgcctg    8760
tagtcccagc tactcaggag gctgaggcag gagaatggtg tgaacccagg aggcggagct    8820
tgcaatgagc caagatcgtg ccactgcact ccagcctggg tgacagagca agactccgtc    8880
tcaaaaaaaa aaagagacaa tagaaacaaa gaccctcaaa acacatagaa agacagcaac    8940
aaccatccct agagacaggg aaattcagag aacagagtac aggcccaagt gcagacaggt    9000
ccgggatttg ggggaagagg aaatggaaaa gtagagagga ccaccagaga agcaaattgc    9060
agtgtgagga gggagcttgt tgtctagtgg tgtgggcagt taagacagac tgaagaaaga    9120
ggcagggaac caggagcca tagaaggtgg gggagggctg gtgacaacag cactattgtt    9180
ctgatagggg gttggggagc aggccctgg ggcaggaaac tggccctctt ccctgctca    9240 gaggcgggat gctggcccag ccaggggagc tggcagccct cttaggagaa acaggtgcaa    9300
tgctttgtaa ggacgcccag gtggtccct ccctgcaa ataccgcca ggcagggacc       9360 aaccctctt aggaaatcca acagtcccag tcccctctaa atccctctct ccagaattct    9420
agattcctcc aaggttgtgc cacacaaaga gaggaaaaaa aaaaaaagga acaatttctc    9480
cgtggtttct ggaggccctg tgcttccggc cagatctgcc ctgggcttag agccagaaga    9540
gaggggtggc agtggggagc tgcagggggg cagaaccgag ggggctgtct cagagctgag    9600
gctgggtctc agggactcag ccctccggat gagagcagag aagggtgtga ctcagtcttt    9660
gaggattgaa tggtagtttc tacattcttc cagatctggg gttggggttg attgaagttg    9720
gtttctagga caacaccagg tgggtaggaa gggaagggga ggggcactc tctagaggct     9780 agatgtcttt ttctagacac cacacacaca caccacaca cacacacaca cacacacaca    9840
cctgaagaac tattttgat gtgaaatggg acaggaataa gaaggaatgt gagtttcaag     9900 gtccccttc atgggtatgg gtcttgggag aagagctgag gaagaggta gacaccagca      9960 tctggacagg gttgtcctgt tggggagaaa gagagcattc ctggggacca gatgatggtg   10020 ttttttgtt tgtttgtttg cttgcttgct tgtttcgaga cggagactcg ctctgttgcc    10080
caggctggag tgcagtggcg cgatctctca gctcactgca acttccacct cctgggttca   10140
agattctggt tcctcagcct cccaagtagc tgggattaca cacccagcta attttttgtt   10200
tttttagtag agactgggtt tcaccatgtt ggccaggggg tctcaaactc ccgaccttcg   10260
gtgatccacc tgcctcagcc tcccagagtg ttggattaca ggtgtgagc caccgcactg   10320 ggcccagatg atggttttga gacttctcca gaaccgacac atcaagaggg actgatttgc   10380
```

-continued

```
aggggaagga ggctaggaaa attgggaatc aaaaaaaaaa aatggtggtt ttgaaggaaa    10440
ggtggagggc caggcggagg gagacctggg atctcacacc gcttttccg tcccccctga     10500
cagtgggcgc tctacctgtt cctggttaaa tgcacgatca gcatttccac cttcttactc    10560
ctctgcctca tcgtggcctt tcatgccaaa gaggtccagg tagggcaggc cccgcccta     10620
agccttgctc cctccaaccc cctcagcgcc ctgtcagctc acactttcca ccctcctcct    10680
cctcctgatc tgagtaatga agttcttctg ccctaggtgc tgcgtccaca ccctcaccta    10740
cccagatggg atgaaccatg agcagacagg cagagcctcc cccaccagct ccgccttccc    10800
ctgtagtccc cagcccccc ttgcacactc acggatgctg agagtgccct tgcagccctg     10860
cttccgcccc caggcctctg tccactctgc tcccaggcac tcagcttccc agatctctgt    10920
gctccgacat ggcatcccca atccagtcct caagcaacct aaggtcctag gctgcccac     10980
tcctttttt tttttttttt tttttttttt ttgagacaag gtcttgctct gttgcccagg     11040
ctagagtgga gtggcacgat ctctgctcac tgcaacctcc acctcctggg ttcaaacaat    11100
tctcatgcct cagcctccca agtagctgtg actacaggca gatgccacca cgcccagcta    11160
attttttgt attttagtag aaacggggtt tcactatgtt gtccaggctg gtctccaact     11220
actgagctca agcagtctgc ccaccttgtc ctcccaaagt gctaggatta cgggcttgag    11280
ccactgcacc tggtccggtc caggggtgc ccactcctaa tcaccctatc tctgtgccaa     11340
taacctccct cttgccccag acccaggagc tctccccatc cataccccac cttgggtctc    11400
acccagacac atcccatccc ctattgtccc attgccccag atcctgttgc tccattccct    11460
ttcccctctt cccctctcc tatcataact ttgcatgtaa aatgggatt attggccatg      11520
tgtggcaatt ctatgagcag tgcctggcac ataagaggtg ctcagtaaac agtgcacatt    11580
atcatcttat catagagtag ctaagtagcc tgtagcccag tgcgccattg cccatggaag    11640
ggacctgggc ctcagcttcc acatctataa aatggggca ataataatat caatctcact     11700
gggttgtggg catttactaa gtcacaatat gtaaacggga tagagcagta cctggcgtat    11760
ccacggtgcc cagtacatgc tgatttttgt attgttattg ttttgtttat tttgagatgg    11820
agtctcgctc tgtcacccag gctagagtgc agtggcatga cctcagctca ctgcaacctc    11880
tgcctcctgg gttcaagtga ttctcctacc tcagactccc cagaagctgg gactataggt    11940
gtgcgccacc atgcccggct tattttgta ttttcagta gagatggagt ttcaccatgt      12000
tggccaggct tgtctcaaac tcttgacctc aagtgatcca cccaccgcag cctcccaaag    12060
tgctgggatt acaggcgtaa gccatcgcgc ccggcccatg gctttgttat tgctgatatt    12120
attattacag ttattacgcg tgtcaaccga aaggggagta ggagcgagct ccaggcatgt    12180
ggaatgcaag ctctagggag gcaggggggt ctgttgggtt cactgtgtat ccttagcaca    12240
tagaacaatg tcaggcacac agtcggcgct cagtcagtgt tcaaaggctg gaagtgggct    12300
gaaactagtg gggtgggtgg tggggaagga ggaaaaagtg gaaagatgtc ttcctcaagt    12360
cctgtcccgc tccctcccta tccctctccc gccctgcact ccctccctcc tggccaggcg    12420
gcacacccca cttatctcag ggcgcaggca ggcgcgggcc gccgcctgac ctgcgcctga    12480
cctgctcctg acccctccct tcttggcccc ctaccggcag ctgttcatga ccgacaacgg    12540
gctgcgggac tggcgcgtgg cgctgaccgg gcggcaggcg gcgcagatcg tgctggagct    12600
ggtggtgtgt gggctgcacc cggcgcccgt gcgggcccg ccgtgcgtgc aggatttagg     12660
ggcgccgctg acctccccgc agccctggcc gggattcctg ggccaagggg aagcgctgct    12720
gtccctggcc atgctgctgc gtctctacct ggtgccccgc gccgtgctcc tgcgcagcgg    12780
```

```
cgtcctgctc aacgcttcct accgcagcat cggcgctctc aatcaagtcc gcttccgcca    12840
ctggttcgtg gccaagcttt acatgaacac gcaccctggc cgcctgctgc tcggcctcac    12900
gcttggcctc tggctgacca ccgcctgggt gctgtccgtg gccgagaggt gagggtgatg    12960
gaggcataaa tgcgcagggg ggaaccccgg acagccacgg cggccgtcct gtgccgcggt    13020
gcaggttgag gcccctagg accaagcagt ggagaaagtt cacactttga ccccttctcc     13080
tcttgctggc tgaaatttgc ccacactccc atcaactggg gtgagaggaa ccaacagaca    13140
agcccccagc caatcctcca cctgcagcct tcagtctccc caaacgcaca cacagaccct    13200
agaaagcccc tcccttccgg ctgcctgacc tctgcctcag gtttacaggc catctgttcg    13260
gtctccgaac ctatctctgg gacctgccta aagggttgcc tctgccttgg aggaaggaga    13320
catattttcc caattagcac ggaatgcact gtaggtaggt gcttttttgtg atcctaggaa   13380
ggggatgatt tggaactgct ctggaaaata attccaagca gggaattgga actagatcct    13440
ggttgccagc tagatactgt gtaacccgat gccgcgcctc aatttctatc cctttcagag    13500
aaaaacgagg ttgggagtga tctcagccag tggtcctcaa agtgtgattt caagaccagc    13560
agcatcacct gggaacttgc aaatgaaaac tctcaggtcc cttccagacc tactgaatcc    13620
tggagggtag ggccagcaat ccactttagc aagccttcca ggtgattcta tggcccaacc    13680
aaggttgaga acctctggtc tagtgtatgt ggcaaagatc cttcagggca ggaggagaat    13740
gagaagatct ggctttagat ctctcctctc tgagcctcag tttcctcatc tgaaaaatgc    13800
atgtcacgtt ccaccatctg tagtctccct ggcagttctt gttttttgat ctggagtctc    13860
aattatccag gctagcgtgc agtggcacaa tctctgctcc ctgcaacctc tgcctcccgg    13920
cttcaagcaa ttctcatgcc tcagcctccc tagtggctgg gattacggat gtgcaccacc    13980
atgcctgact agttttttgta ttttagtag agaccacgtt accgtgttgc ccaggctggt    14040
tttgaactct tgattcaag tgatcctcct gcctaagcct cccaaagtgc tgggattacc     14100
atgcccgccc tctgtcatga gtttaaactc cttcaccttc caggatctta gttttcacaa    14160
ttgggaaatt ggtcagaatc aggattaatg aatgatcccc ccaccatgtt tctcaattga    14220
atgatgggag aatggggagg aagtcaaagt tccacattcc aaggcagaag tcctgaaaact   14280
agaatgtact tcggaatgag ggggtgggt ttgtgaacag tacagattcc atcttcgctc     14340
ctagaaactc caacccggtg ggtctggggt gtcaggggcc ctcatgaatg aagctttccc    14400
tgctggtctt gcggcaaggg gcctgtggac aaagttagac aaatctcaat gtttcaaccc    14460
cttccatggc tggacttaaa tgtctcctct gtgaagtgag aggaaaggaa ggccgagtcc    14520
caccaagcct ttttagagtc cttttttggtc ctgatagggc cacttctgga ccacacagca   14580
tctttgtgga aattagaaaa atatacccct tcctctgggt ggatgtagcc accagtcagg    14640
gtctgactgg gttttggccc cctatcgact ctccaccctc aaccacacgc tctgaatgct    14700
acagcagccc gggtagccta gctgagacca taccggcatt gggattggcc agacccagtc    14760
tcaaatccca gagtggctaa gcaacttgcc caggtcacac agcagagagg aggccatgca    14820
ggctttccaa agctcagaac ttaatggctt tttgtccagg tgattcttag gactatgggt    14880
gtatactggg aggggaaggg agggaaccag agggaagggg atgggagggt atagagggaa    14940
ggggagtgaa tatcatggaa acctctatgg tggggtttta gaactaacct acccttcccc    15000
ataggcaggc tgttaatgcc actgggcacc tttcagacac actttggctg atccccatca    15060
cattcctgac catcggctat ggtgacgtgg tgccgggcac catgtgggc aagatcgtct     15120
gcctgtgcac tggagtcatg gtgagtacag ctgccttggg gacatgatcc ctatcccaaa    15180
```

```
ctggtcatcc tctggcccca ggaagccatg attaaatggg ttcaacacag gctctcaggg    15240
acagctcctg agaaacttga gtgtctgggg cccccagagc cccattctct cttcaagaac    15300
aagatactca cctgtaatcc caatattttg ggaggccaag gtgggaggat cacttgagcc    15360
caagagtttg agggtacagt gagctatgat catactgctg cactccagcc tgggtggcag    15420
agtgagaccc tgtctcttaa aaaataaaat aaaaaatcag acctaggaat ccagcccta    15480 agtccttgct ctctctagaa cctagggccc cagcccttat cctcctcagg gacccaggct    15540
cctgacttcg cagccccatt ttcttccaga actgggaaat cgtctcccag cctccatcaa    15600
gggtgtagag tccagttatc aagtgcatac ctgtggggcc aggctacctg ggtccgaatc    15660
ctgcggctgc cacttcctgg ctggggagct caggcgagcc acgtgatctc tcggggcctc    15720
actttcctca tctataaaat ggggatgctg atgctcctca tgggcttgct gagatgatta    15780
aatgggtcca actacgtaaa gtgcttccaa cagtgcccag cccacaggag gtgctcagta    15840
aacaggtcta ggggtggcca ggcatccagc caccccacac cagctcctgt tgccctcaag    15900
gatgaggcag aggctctgca gcctgagtca gcctcttcct gaaccctgac atccacctcc    15960
ttccctccat agacccagtc actcaggtcc tcccacccag ccctggcccc ctctagagac    16020
tagcacctaa tgccttggcc ttcacctccc tacaagatcg ggttcccctc accctcgggg    16080
acctaagcca ccagcaccta gcccagatgt gggcctagga aggacatatt catcccccaa    16140
tccctaggtg cacaggtgaa ggatgtggtg acctccactc cccagtggt gagtctttgg    16200 agcaagggaa gaggggcaga gactcagtta gggacctgca gcaccgctca ggacctcctc    16260
cctcatttga caaaggaga aacagaaacc tagagagata gggtgatgtg cacttgagct    16320
cacagcctgc tcctggaaga aaggctccat ggcatggttg ggccataaaa gcttactttt    16380
ccggagcaca tactctgtgc cagtctctgc cctacacact tgccagggt aattcatgaa    16440 atccacctag taaccctgtg aggccatttc acagatgaga cactgaaata ctgagagatt    16500
aaataacttg ctcagagctg ggcttggaac ccaggcagtc ccctggagcc agcgtttgtg    16560
actggaagtt gttctgagtg atcaagagct gaaactatag ggttgggat gcttcctagg    16620 aagattcctt ctaacttggg gacaggtgag cagatgccac aagcagctag gaattgccaa    16680
ggccttgaag ggccaggagc attgggagaa ggaagggagg agaatgagtg ttcggaggaa    16740
ggtgctcagg gagggcaggc agcatggagc cagggctgag ttgtccaggt gggaggcata    16800
gaccttggaa ggccttggga gccaggctga gacgttcagg ccagtggaag cctgggagat    16860
tagaggggac caaggggtt aggggaggat gagtgggagg ctggagacgg tccaggagag    16920
agaagacagg gctggagcta ggaagaagtt gtgggagtgg gagaaggatg gtcgccctcc    16980
acagtgcaat ggctgaccac atgagcactg aggacccaga ggcctgcccc tggctcagaa    17040
cccagccttc ctctcactcc tccaatccta tccttcattc aagaggccac cctgagggtg    17100
tgaatgctat gcatcaaatt tgggctcgga cgtatgcgat ttatgattct agctccaccg    17160
ctctgagctg ggaccttggc tctcctctct gagcctcttt gcttgtctgc taactgggga    17220
tggtcgtgcc taccgtctgt ggctgttggg cgggttcaag gagggagtcg gtggcacagc    17280
ctcatgccac ggtgcctgct gtgcccacag ggtgtctgct gcacagccct gctggtggcc    17340
gtggtggccc ggaagctgga gtttaacaag gcagagaagc acgtgcacaa cttcatgatg    17400
gatatccagt ataccaaaga ggtgagatgg gcatatggca cccatgggac acccctcttc    17460
caagaagcag gagtccaggc gcccctgctt ccccctaggac ccaagagtcc cagccctagc    17520
cctgccttcc cagaaccgta agggtctatc tccacggaca ctgtgccacc cacccccaga    17580
```

```
tgaaggagtc cgctgcccga gtgctacaag aagcctggat gttctacaaa catactcgca    17640
ggaaggagtc tcatgctgcc cgcaggcatc agcgcaagct gctggccgcc atcaacgcgt    17700
gagggccgct ttgtatgcac acgtgtccat gtgcacccat gtccaagtca cctctctgca    17760
cggctgtgtg tgtgcatgtc catgcctgtc caggtcagga cacccaggtg tggtctcact    17820
caacatccag gtctcacctg gatctgaccg tgcatgactc tatgtgtctg tgctggtttg    17880
tctccgcata tctcggtgtg tctgcggacc tgggtacctg ggtttctact ggggatgggg    17940
gctcgtgggg aggcagggtg catcccctcc cactctttca gctcttcgac aactttgttt    18000
ctttgttttg tttcttcatg tgcctctcct cccttcattc ctcccctgag ctacagctac    18060
attcagggac caggcttgta aaactgactc cccacttctt cccacaggtt ccgccaggtg    18120
cggctgaaac accggaagct ccgggaacaa gtgaactcca tggtggacat ctccaaggta    18180
ctaggatccc gtgggaggag gtcttgaaga agggggaggt tggggccaca gggagggaaa    18240
tctggcccta gaacagggaa ccttggcagg ggcctggcac acacagcctg tcagtaaagg    18300
tctgtggttg aatgaaggaa ggaaggaatg aatgatgcaa cacagagctt cttacattca    18360
tgaaaggcac agatccctta caaactgaaa aaaaaaaat tgcacaaaga accccagtgt    18420
ttggtttcaa attatcttta ttgttaagtt acttacatgt ggacggatat aaaattcctt    18480
ccaactacag ctcatacaat aaaaccaaag caaatttaca aaccaagccc atagacggca    18540
aaaccaatac aattaaaatg aacaacactg acaaggacaa aggtgacatt gtttccgtaa    18600
aactcaatct ctgctgctct tgtggagggg tactcagggc aacagggacg tccatgcaag    18660
tttgcctggc caaggcgtga ctcagctacc cgccccttc ttctgctgag accatttgat    18720
ttcgccagtg cttagggaca atgatgtcac aacacccct tggcctggct cacagcatct    18780
tctgcttatc tggtggcctt tgcttttct cgttagccca cgacagttca aacagtggcc    18840
cctggcagca atgccatggt aagcacggtc acagatgcag gccccaaaac cgcatggcag    18900
gtctcagtga cgaggcagtg gcccagatct gcaggaattg gcaggtggta atttctgaag    18960
gttatcaagc caaaaacaca gaattcaaga atttccatag aaaatccaca aaccctcagg    19020
gatcaactag tgaatcctag ccagagaatg cagtaaaaga ctatgtggat ttggaagtca    19080
ggcatcatcc atgctagaaa tatctaatga gcacctgcta tgttctaggt cttatttcag    19140
gagctgcttt gggcatgtca tttaactgtt ccatgcctgt ttcctcagct gtaagacagg    19200
aacaggattc ccactccctg tggcttttgg gaggatttta aaccatatag ggaaacacct    19260
gggcaggtag ctgggaagtg gtaggtggtc aatacatggt aacagttatt gtcgagggta    19320
atcctcagag gaccataagg atgtggtcaa tattggttcc attgccttac gctatggagt    19380
aggtgggggt cgaccccagc ccgacacct ctgatcctct cctcccaccc agatgcacat    19440
gatcctgtat gacctgcagc agaatctgag cagctcacac cgggccctgg agaaacagat    19500
tgacacgctg gcggggaagc tggatgccct gactgagctg cttagcactg ccctggggcc    19560
gaggcagctt ccagaaccca gccagcagtc caagtagctg gtgaggggc tgggacttgg    19620 gcaggaaggc atcctggagg aagggttcct gtggccagca ccctatgtgg ctaaggggc    19680 gggggatggc tgggagacaa ggccgccttt tctcatcagc tctggcactg tctgaggaa    19740 aggactcagt tcggggctgg actggcagtg aaggaagatg gtgtaccctc tccccttcac    19800
tgacccttga tggccttctc cctctttgct tggtctctct ctctctctct gcctgtcctg    19860
ggcacattgt ctggctgtcc atccaatgtc tctgtctaaa tgccctcctg cccctggcc    19920 tcggggcccg gaaacacctg ccccctgtct cccacttctg cccaccggtt tctgtctgca    19980
```

-continued

```
cctcggtgtg tcccactctc actctccctc ttcctggcct gcctctccat cagtctctct    20040
gtctctccag gacccacgag gaggaaccag gctactttcc ccagtactga ggtggtggac    20100
atcgtctctg ccactcctga cccagccctg aacaaagcac ctcaagtgca aggaccaaag    20160
ggggccctgg cttggagtgg gttggcttgc tgatggctgc tggaggggac gctggctaaa    20220
gtgggtaggc cttggcccac ctgaggcccc aggtgggaac atggtcaccc ccactctgca    20280
taccctcatc aaaaacactc tcactatgct gctatggacg acctccagct ctcagttaca    20340
agtgcaggcg actggaggca ggactcctgg gtccctggga agagggtac taggggcccg     20400
gatccaggat tctgggaggc ttcagttacc gctggccgag ctgaagaact gggtatgagg    20460
ctggggcggg gctggaggtg gcgccccctg gtgggacaac aaagaggaca ccatttttcc    20520
agagctgcag agagcacctg gtggggagga agaagtgtaa ctcaccagcc tctgctctta    20580
tctttgtaat aaatgttaaa gccagaagtt gccatttctc tctaaacata tctacactcc    20640
taactggcag accgtccagt ggaagactgt tgccttgtct gaacctgtct cagaggcctt    20700
ctcctgtaag tgccctccca actctgtagg ctgggcagtc ctcagcaaca gtccctgcc     20760
cagatctgag gcaaagagca acagctttga actcagacag atcagggtcc aaatcctggt    20820
tctaccatcc actggtggtg tgatcttggg taagtggctt cacctctgaa cagtttacct    20880
cacctgtgaa atgggactgc ctccccatgg aactgctgtg aagattaaaa catggagtag    20940
cccagaggca tttagtagga accaaatatg tgagagagaa tcttttttt tttttttga     21000
gatggagtct tgctctgtca cccaggctgg agtacagtgg cgcgatttcg gctcactgca    21060
acctccgcct ccagagttca gcgattctc ctgccttagt ccccaagtag ctgggattac     21120
aggcacctgc caccacgcct ggctaatttt tgtatttta gtagagatgg ggtttcacta    21180
tgttgcagat gctggtcttg aactcctggg ctcaagcaat ctgcccgcct cagcctccca    21240
aagtgctggg attacaagcg tgagccactg tccctggcca agaatcattt ttattattgt    21300
ttttgatttt cacacacaat gcgtggctgc cctttttctg attttttgtt gcttttctcc    21360
ctctattcat gccttaccag aatctagatg acaactcact catcaagaga ctaacagagg    21420
ccccaaacct cccaaacca cccacatacc cgtttcacat ccgctcaaga gaggatgtga    21480
aagggaaggg ggcaaaggag gggggctggc acttccagag gccctactgt gtgcccagct    21540
ctgtttataa gtcaccataa ccactctcct gaccctcgtt accccactgc acagatgtag    21600
aaaccgaggt ttcaagagga gccaggcctc ccctcaggcc cccagccgga agctaggaat    21660
acgggctgga gagcccagat tcacacccat ccgccccac tgcaaggtga gtcagaggca     21720
gagtggcctt gggccacaaa ccgaggactg acttcccgcc gcaacttcat tccagcttga    21780
gaggctgatt cattcttgct tccctcctct tgagggaag atcaggctgc gagtcatcct     21840
tttctgttga gctatctttg gatttccctt aaagtccaca gccagcctcg cccttcatc    21900
cctgagagct aaattggagc ctccgccacc cactgccacg aactgcccctt cctctggagg    21960
ccagcccacc tgggagtaa aggcggggac tcaagaaagg aactggatga gacctccaga    22020
tattgctgac accctttcccc tgcaagaagc tctcctggca gtgttgccaa agccctgcc    22080
aaactcattc ttctgggacc tctctttcct tgcctccact cccttttagc tggcaaacac    22140
tccttcctac gcctcctgta ggcctcggct aatatgtccc ctcctccagg aggccctgtc    22200
tgatactcct atagcctcat aaacctatcc ctatcacgat aataatattg ggtctggcca    22260
ggcatggtgg ctcacgcctg taattccagc actttgggag gccgaggcag gcagatcacc    22320
tgaggccagg agttcgagac cagcctggcc aaaatggtga aaccctgtct atactgaaaa    22380
```

```
tacaaaaatt agccaggcgt ggtggtgtgt gcctgtaatc ccagctactc gggagtctga   22440
ggcaggagat cacttgaacc caggaggcgg agtttgccgt gagccgagat cgtgccactg   22500
cactccagcc tgggtgacag agcaagactc catctcaaac aacaacaaca acgacaacga   22560
caacaaatta gccaggtgtg ggggcacaca cctgtggtcc cagctac                22607
```

<210> SEQ ID NO 2
<211> LENGTH: 1870
<212> TYPE: DNA
<213> ORGANISM: Homo sapiens

<400> SEQUENCE: 2

```
ccgggggcca tgggcgggga tctggtgctt ggcctggggg ccttgagacg ccgaaagcgc     60
ttgctggagc aggagaagtc tctgccggc tgggcactgg tgctggcagg aactggcatt    120
ggactcatgg tgctgcatgc agagatgctg tggttcgggg ggtgctcgtg ggcgctctac    180
ctgttcctgg ttaaatgcac gatcagcatt tccaccttct tactcctctg cctcatcgtg    240
gcctttcatg ccaaagaggt ccagctgttc atgaccgaca cgggctgcg ggactggcgc    300 gtggcgctga ccgggcggca ggcggcgcag atcgtgctgg agctggtggt gtgtgggctg    360
cacccggcgc ccgtgcgggg cccgccgtgc gtgcaggatt taggggcgcc gctgacctcc    420
ccgcagccct ggccgggatt cctgggccaa ggggaagcgc tgctgtccct ggccatgctg    480
ctgcgtctct acctggtgcc ccgcgccgtg ctcctgcgca gcggcgtcct gctcaacgct    540
tcctaccgca gcatcggcgc tctcaatcaa gtccgcttcc gccactggtt cgtggccaag    600
ctttacatga cacgcaccc tggccgcctg ctgctcggcc tcacgcttgg cctctggctg    660
accaccgcct gggtgctgtc cgtggccgag aggcaggctg ttaatgccac tgggcacctt    720
tcagacacac tttggctgat ccccatcaca ttcctgacca tcggctatgg tgacgtggtg    780
ccgggcacca tgtggggcaa gatcgtctgc ctgtgcactg gagtcatggg tgtctgctgc    840
acagccctgc tggtggccgt ggtggcccgg aagctggagt ttaacaaggc agagaagcac    900
gtgcacaact tcatgatgga tatccagtat accaaagaga tgaaggagtc cgctgcccga    960
gtgctacaag aagcctggat gttctacaaa catactcgca ggaaggagtc tcatgctgcc   1020
cgcaggcatc agcgcaagct gctggccgcc atcaacgcgt tccgccaggt gcggctgaaa   1080
caccggaagc tccgggaaca agtgaactcc atggtggaca tctccaagat gcacatgatc   1140
ctgtatgacc tgcagcagaa tctgagcagc tcacaccggg ccctggagaa acagattgac   1200
acgctggcgg ggaagctgga tgccctgact gagctgctta gcactgccct ggggccgagg   1260
cagcttccag aacccagcca gcagtccaag tagctggacc cacgaggagg aaccaggcta   1320 cttttccccag tactgaggtg gtggacatcg tctctgccac tcctgaccca gccctgaaca   1380
aagcacctca agtgcaagga ccaaaggggg cctggcttg gagtgggttg gcttgctgat   1440
ggctgctgga ggggacgctg gctaaagtgg gtaggccttg gcccacctga gccccaggt   1500 gggaacatgg tcacccccac tctgcatacc ctcatcaaaa acactctcac tatgctgcta   1560
tggacgacct ccagctctca gttacaagtg caggcgactg gaggcaggac tcctgggtcc   1620
ctgggaaaga gggtactagg ggcccggatc caggattctg ggaggcttca gttaccgctg   1680
gccgagctga agaactgggt atgaggctgg ggcggggctg gaggtggcgc ccctggtgg    1740 gacaacaaag aggacaccat ttttccagag ctgcagagag cacctggtgg ggaggaagaa   1800
gtgtaactca ccagcctctg ctcttatctt tgtaataaat gttaaagcca aaaaaaaaa    1860 aaaaaaaaa                                                           1870
```

```
<210> SEQ ID NO 3
<211> LENGTH: 427
<212> TYPE: PRT
<213> ORGANISM: Homo sapiens

<400> SEQUENCE: 3

Met Gly Gly Asp Leu Val Leu Gly Leu Ala Leu Arg Arg Arg Lys
1               5                   10                  15

Arg Leu Leu Glu Gln Glu Lys Ser Leu Ala Gly Trp Ala Leu Val Leu
                20                  25                  30

Ala Gly Thr Gly Ile Gly Leu Met Val Leu His Ala Glu Met Leu Trp
            35                  40                  45

Phe Gly Gly Cys Ser Trp Ala Leu Tyr Leu Phe Leu Val Lys Cys Thr
    50                  55                  60

Ile Ser Ile Ser Thr Phe Leu Leu Leu Cys Leu Ile Val Ala Phe His
65                  70                  75                  80

Ala Lys Glu Val Gln Leu Phe Met Thr Asp Asn Gly Leu Arg Asp Trp
                85                  90                  95

Arg Val Ala Leu Thr Gly Arg Gln Ala Ala Gln Ile Val Leu Glu Leu
            100                 105                 110

Val Val Cys Gly Leu His Pro Ala Pro Val Arg Gly Pro Pro Cys Val
    115                 120                 125

Gln Asp Leu Gly Ala Pro Leu Thr Ser Pro Gln Pro Trp Pro Gly Phe
130                 135                 140

Leu Gly Gln Gly Glu Ala Leu Leu Ser Leu Ala Met Leu Leu Arg Leu
145                 150                 155                 160

Tyr Leu Val Pro Arg Ala Val Leu Leu Arg Ser Gly Val Leu Leu Asn
                165                 170                 175

Ala Ser Tyr Arg Ser Ile Gly Ala Leu Asn Gln Val Arg Phe Arg His
            180                 185                 190

Trp Phe Val Ala Lys Leu Tyr Met Asn Thr His Pro Gly Arg Leu Leu
    195                 200                 205

Leu Gly Leu Thr Leu Gly Leu Trp Leu Thr Thr Ala Trp Val Leu Ser
210                 215                 220

Val Ala Glu Arg Gln Ala Val Asn Ala Thr Gly His Leu Ser Asp Thr
225                 230                 235                 240

Leu Trp Leu Ile Pro Ile Thr Phe Leu Thr Ile Gly Tyr Gly Asp Val
                245                 250                 255

Val Pro Gly Thr Met Trp Gly Lys Ile Val Cys Leu Cys Thr Gly Val
            260                 265                 270

Met Gly Val Cys Cys Thr Ala Leu Leu Val Ala Val Ala Arg Lys
    275                 280                 285

Leu Glu Phe Asn Lys Ala Glu Lys His Val His Asn Phe Met Met Asp
290                 295                 300

Ile Gln Tyr Thr Lys Glu Met Lys Glu Ser Ala Ala Arg Val Leu Gln
305                 310                 315                 320

Glu Ala Trp Met Phe Tyr Lys His Thr Arg Arg Lys Glu Ser His Ala
                325                 330                 335

Ala Arg Arg His Gln Arg Lys Leu Leu Ala Ala Ile Asn Ala Phe Arg
            340                 345                 350

Gln Val Arg Leu Lys His Arg Lys Leu Arg Glu Gln Val Asn Ser Met
    355                 360                 365

Val Asp Ile Ser Lys Met His Met Ile Leu Tyr Asp Leu Gln Gln Asn
370                 375                 380
```

-continued

```
Leu Ser Ser Ser His Arg Ala Leu Glu Lys Gln Ile Asp Thr Leu Ala
385                 390                 395                 400

Gly Lys Leu Asp Ala Leu Thr Glu Leu Leu Ser Thr Ala Leu Gly Pro
                405                 410                 415

Arg Gln Leu Pro Glu Pro Ser Gln Gln Ser Lys
                420                 425
```

ENGINEERED STEM CELLS AND CELLULAR PRODUCTS PRODUCED AND SECRETED BY SUCH CELLS, METHODS OF PREPARING, AND USES THEREOF

RELATED APPLICATIONS

This application claims priority to U.S. provisional application No. 62/758,160 filed Nov. 9, 2018, which is herein incorporated by reference in its entirety.

TECHNICAL FIELD

Example embodiments relate to engineered stem cells and cellular products for therapeutic use.

BACKGROUND

Despite significant advances in the management of cardiac diseases over the past decades, heart failure (HF) remains one of the top killers worldwide (1). Stem-cell therapy has emerged as a promising approach to prevent the progression of HF (2).

Although the potential of adult stem cell therapy is widely recognized, initial trials reported modest and inconsistent improvement in cardiac function (2). Some ex vivo preconditioning strategies have been proposed to enhance the reparative potential of the transplanted cells in order to observe clinically relevant benefits (57).

There is a need to develop improved methods and compositions for enhancing repair and improve function of the damaged heart.

SUMMARY

The present disclosure relates to methods for altering the endogenous ionic flows of a cell or tissue to prevent and/or treat a broad range of diseases, including cardiac disease.

In an example embodiment, there is provided a method for modulating the bioelectric property of a stem cell. In one embodiment, the modulated bioelectric property is a hyperpolarized transmembrane potential. In a further embodiment, the hyperpolarized transmembrane potential is a result of an increased expression of the intermediate-conductance $Ca^{2+}$-activated $K^+$ channel or functional fragment thereof. In one aspect, the increased expression of the intermediate-conductance $Ca^{2+}$-activated $K^+$ channel or functional fragment thereof overcomes for an otherwise decreased expression of the intermediate-conductance $Ca^{2+}$-activated $K^+$ channel in the stem cell. In one aspect, the stem cells are stems cells that functionally express the intermediate-conductance $Ca^{2+}$-activated $K^+$ channel or functional fragment thereof. In further aspects, the stem cells that functionally express the intermediate-conductance $Ca^{2+}$-activated $K^+$ channel or functional fragment thereof include cardiac-derived stem cells, bone marrow-derived mesenchymal stem cells, blood-derived endothelial progenitor cells, or adipose-derived progenitor cells.

In a further embodiment, the cardiac-derived stem cells are cardiac explant-derived stem cells (EDCs). In a further embodiment, the increased activity of the intermediate-conductance $Ca^{2+}$-activated $K^+$ channel or functional fragment thereof directs cardiac explant-derived stem cell functions, including, but not limited to, proliferation, differentiation, cytokine secretion, or extracellular vesicle production, or any combination thereof.

In an example embodiment, there is provided a composition comprising EDCs having an increased expression of intermediate-conductance $Ca^{2+}$-activated $K^+$ channel or functional fragment thereof, extracellular vesicles secreted therefrom, or contents of the extracellular vesicles, for improving cardiac function through angiogenesis, cardiomyogenesis, or myocardial salvage, or any combination thereof. In an example embodiment, there is provided a method for making the composition comprising EDCs having an increased expression of intermediate-conductance $Ca^{2+}$-activated $K^+$ channel or functional fragment thereof, extracellular vesicles secreted therefrom, or contents of the extracellular vesicles, for improving cardiac function through angiogenesis, cardiomyogenesis, or myocardial salvage, or any combination thereof. In an example embodiment, there is provided a method of treating or ameliorating a damaged myocardium in a subject, the method comprising: administering a composition comprising EDCs having an increased expression of intermediate-conductance $Ca^{2+}$-activated $K^+$ channel or functional fragment thereof, extracellular vesicles secreted therefrom, or contents of the extracellular vesicles, wherein the administration improves cardiac function through angiogenesis, cardiomyogenesis, or myocardial salvage, or any combination thereof.

In an example embodiment, there is provided methods and compositions to enhance KCa3.1-channel expression to increase the proliferation and/or enhance the paracrine profile of EDCs in vitro.

In an example embodiment, the over-expression KCa3.1-channel increases both proliferation and the paracrine spectrum of EDCs. In another example embodiment, the changes enhanced cardiac function by promoting the growth of new blood vessels and/or cardiomyocytes. In another example embodiment, the changes reduced myocardial scar burden without increasing the risk of malignant cardiac rhythms.

According to one aspect, there is provided a cardiac explant-derived stem cell (EDC), the cell comprising a gene encoding an intermediate-conductance $Ca^{2+}$-activated $K^+$ channel or functional fragment thereof, and wherein the gene causes an overexpression of the intermediate-conductance $Ca^{2+}$-activated K+ channel or functional fragment thereof. In one aspect, the gene comprises KCNN4 gene or functional fragment thereof and the intermediate-conductance $Ca^{2+}$-activated $K^+$ channel is KCa3.1 channel or functional fragment thereof.

In one aspect, the gene is configured to drive expression of the KCa3.1 channel to hyperpolarize the EDC membrane and enhance $Ca^{2+}$ signalling of the EDC. In one aspect, the gene is configured to drive expression of the KCa3.1 channel to hyperpolarize the EDC membrane and increase intracellular $Ca^{2+}$ concentration ($[Ca^{2+}]_i$) in the EDC. In one aspect, the gene is configured to drive expression of the KCa3.1 channel to increase the paracrine repertoire of the EDC relative to control EDC which do not contain the gene or contain only an empty backbone. In one aspect, the gene is configured to drive expression of the KCa3.1 channel to decrease the resting membrane potential of the EDC and maintain the electrical gradient for $Ca^{2+}$influx in the EDC relative to control EDC which do not contain the gene or contain only an empty backbone. In one aspect, the gene is configured to drive expression of the KCa3.1 channel to increase the production of cytokines relative to control EDC which do not contain the gene or contain only an empty backbone. In a further aspect, the cytokines are VEGF, angiogenin, IGFBP3, SDF-1α, ICAM-1, or combinations thereof.

In one aspect, the gene is expressed from a vector comprising a promoter operably linked to the gene. In a further aspect, the promoter is a constitutive active promoter. In a further aspect, the vector is a lentiviral vector. In one aspect, the EDC is CD90⁻. In one aspect, the EDC was isolated from cultured cardiac explant tissue and then transduced with the gene.

Further disclosed herein is the use of the cardiac explant-derived stem cell for treating or ameliorating a damaged myocardium in a subject. In one aspect, the cardiac explant-derived stem cell (EDC) increases angiogenesis; increases cytokine production; increases post-infarct healing; promotes immunomodulation; increases cardiomyocyte proliferation and/or salvage; protects against oxidative stress; reduces cardiac fibrosis; increases transplanted-cell engraftment; or any combination thereof. In one aspect, the cardiac explant-derived stem cell is formulated for injection. In one aspect, the EDC is formulated for intra-myocardial injection.

Further disclosed herein is a method for treating or ameliorating a damaged myocardium in a subject, the method comprising: administering a cardiac explant-derived stem cell (EDC) to the damaged myocardium of the subject. In one aspect, before the step of administering, obtaining the EDC by extracting a cardiac explant tissue from the subject, isolating the EDC from the extracted cardiac explant tissue, and introducing the KCNN4 gene to increase the expression of KCa3.1 channels in the EDC. In one aspect, the EDC increases angiogenesis; increases cytokine production; increases post-infarct healing; promotes immunomodulation; increases cardiomyocyte proliferation and/or salvage; protects against oxidative stress; reduces cardiac fibrosis, increases transplanted-cell engraftment; or any combination thereof. In one aspect, the administering is by injection, and preferably, by intra-myocardial injection.

Further disclosed herein is a method for producing engineered cardiac explant-derived stem cells (EDCs) having a modulated bioelectric property, the method comprising: obtaining cardiac explant-derived stem cells (EDCs); introducing a gene encoding an intermediate-conductance $Ca^{2+}$-activated $K^+$ channel or functional fragment thereof into the EDCs to increase the expression of the intermediate-conductance $Ca^{2+}$-activated $K^+$ channel or functional fragment thereof, to produce engineered EDCs. In one aspect, the modulated bioelectric property is a hyperpolarized cell membrane and an increased driving force for $Ca^{2+}$-entry. In one aspect, the gene comprises KCNN4 gene and the intermediate-conductance $Ca^{2+}$-activated $K^+$ channel is KCa3.1 channel. In one aspect, the step of obtaining comprises extracting cardiac explant tissue from a subject and isolating the cardiac explant-derived stem cells (EDCs) from the extracted cardiac explant tissue. In one aspect, the step of isolating comprises digesting the extracted cardiac explant tissue with collagenase, growing the EDCs in cell culture containing cell culture media and oxygen, and harvesting the EDCs from the cell culture. In one aspect, the EDCs are maintained under ischemic conditions, the EDCs demonstrate one or more of: an increase in proliferation; an increase expression of cytokines implicated in angiogenesis, post-infarct healing, immune modulation, or combinations thereof; an increase number of extracellular vesicles; and an increase in miRNA associated with cardiomyocyte proliferation, cardiomyocyte salvage, protection against oxidative stress, reducing cardiac fibrosis, increase transplanted-cell engraftment, or combinations thereof. In one aspect, the extracellular vesicles comprise VEGF, angiogenin, IGFBP3, SDF-1α, ICAM-1, or combinations thereof. In one aspect, the extracellular vesicles comprise miR-199a-5p, miR-125b-5p, miR-21-5p, miR-22-3p, or combinations thereof.

Further disclosed herein is a method for treating or ameliorating a damaged myocardium in a subject, the method comprising: introducing a gene encoding an intermediate-conductance $Ca^{2+}$-activated $K^+$ channel or functional fragment thereof into cardiac explant-derived stem cells (EDCs) to increase the expression of the intermediate-conductance $Ca^{2+}$-activated $K^+$ channel or functional fragment thereof, to produce engineered EDCs; culturing the engineered EDCs in conditions sufficient for the engineered EDCs to produce extracellular vesicles; isolating the extracellular vesicles; and administering the extracellular vesicles to the subject to treat or ameliorate the damaged myocardium. Further disclosed herein is a method for producing extracellular vesicles to treat or ameliorate a damaged myocardium in a subject, the method comprising: introducing a gene encoding an intermediate-conductance $Ca^{2+}$-activated channel or functional fragment thereof into cardiac explant-derived stem cells (EDCs) to increase the expression of the intermediate-conductance $Ca^{2+}$-activated $K^+$ channel or functional fragment thereof, to produce engineered EDCs; culturing the engineered EDCs in conditions sufficient for the engineered EDCs to produce extracellular vesicles; and isolating the extracellular vesicles.

In one aspect, the gene comprises KCNN4 gene and the intermediate-conductance $Ca^{2+}$-activated $K^+$ channel is KCa3.1 channel. In one aspect, the step of isolating comprises collecting the cell culture media containing extracellular vesicles secreted into the cell culture media and then separating the extracellular vesicles from the cell culture media. In one aspect, the step of culturing comprises maintaining the EDCs in conditions mimicking the environment of the ischemic heart. In one aspect, the conditions are one or more of low oxygen and the absence of growth factor supplementation in the cell culture media. In one aspect, the low oxygen is about 1% oxygen. In one aspect, the step of maintaining is around 48 hours. In one aspect, the extracellular vesicles comprise cytokines, preferably, the cytokines are those implicated in angiogenesis, post-infarct healing, immune modulation, or combinations thereof and miRNA, preferably the miRNA are those associated with cardiomyocyte proliferation, cardiomyocyte salvage, protection against oxidative stress, reduction of cardiac fibrosis, increased transplanted-cell engraftment, or combinations thereof. In one aspect, the extracellular vesicles comprise VEGF, angiogenin, IGFBP3, SDF-1α, ICAM-1, or combinations thereof. In one aspect, the extracellular vesicles comprise miR-199a-5p, miR-125b-5p, miR-21-5p, miR-22-3p, or combinations thereof.

Further disclosed herein is a composition for treating or ameliorating a damaged myocardium in a subject, the composition comprising the extracellular vesicles produced according to the method as disclosed herein.

Further disclosed herein is a composition for treating or ameliorating a damaged myocardium in a subject, the composition comprising the engineered EDCs produced according to the method as disclosed herein.

Further disclosed herein is a composition for treating or ameliorating a damaged myocardium in a subject, the composition comprising the cell culture media obtained after the culturing of the engineered EDCs produced according to the method as disclosed herein.

Further disclosed herein is a composition for treating or ameliorating a damaged myocardium in a subject, wherein the composition further comprises a pharmaceutically acceptable carrier.

Further disclosed herein is a use of a composition as disclosed herein for treating or ameliorating a damaged myocardium in a subject. Further disclosed herein is a method for treating or ameliorating a damaged myocardium in a subject comprising administering a composition as disclosed herein to a subject in need thereof.

Further disclosed herein is a kit comprising a composition as disclosed herein and instructions for using the kit.

Further disclosed herein is a method for manufacturing a medicament for treating or ameliorating a damaged myocardium in a subject, the method comprising: obtaining cardiac explant-derived stem cells (EDCs); introducing a gene encoding an intermediate-conductance $Ca^{2+}$-activated $K^+$ channel or functional fragment thereof into the EDCs to increase the expression of the intermediate-conductance $Ca^{2+}$-activated $K^+$ channel or functional fragment thereof, to produce engineered EDCs, wherein when the engineered EDCs are administered to the damaged myocardium, the engineered EDCs increase angiogenesis; increase cytokine production; increase post-infarct healing; promote immunomodulation; increase cardiomyocyte proliferation and/or salvage; protect against oxidative stress; reduce cardiac fibrosis, increase transplanted-cell engraftment; or any combination thereof. In one aspect, the gene comprises KCNN4 gene and the intermediate-conductance $Ca^{2+}$-activated $K^+$ channel is KCa3.1 channel. In one aspect, the step of obtaining comprises extracting cardiac explant tissue from a subject and isolating the EDCs from the extracted cardiac explant tissue. In one aspect, the step of isolating comprises digesting the extracted cardiac explant tissue with collagenase, growing the EDCs in cell culture containing cell culture media and oxygen, and harvesting the EDCs from the cell culture. In one aspect, the step of harvesting comprises trypsin, preferably TrypLE.

Further disclosed herein is a composition for treating or ameliorating a damaged myocardium in a subject, the composition comprising extracellular vesicles isolated from cultures of engineered cardiac explant-derived stem cells (EDCs), the engineered cardiac explant-derived stem cells (EDCs) comprising a gene encoding an intermediate-conductance $Ca^{2+}$-activated $K^+$ channel, and wherein the gene causes an overexpression of the intermediate-conductance $Ca^{2+}$-activated $K^+$ channel.

Further disclosed herein is a method for treating or ameliorating a damaged myocardium in a subject, the method comprising: administering the composition comprising extracellular vesicles isolated from cultures of engineered cardiac explant-derived stem cells (EDCs), the engineered cardiac explant-derived stem cells (EDCs) comprising a gene encoding an intermediate-conductance $Ca^{2+}$-activated $K^+$ channel, and wherein the gene causes an overexpression of the intermediate-conductance Ca2+-activated K+ channel, wherein the composition increases angiogenesis; increases cytokine production; increases post-infarct healing; promotes immunomodulation; increases cardiomyocyte proliferation and/or salvage; protects against oxidative stress; reduces cardiac fibrosis; increases transplanted-cell engraftment; or any combination thereof. In one aspect, the administering comprises myocardial injection or myocardial infusion. In one aspect, the injection is intramyocardial injection and the myocardial infusion is intra-arterial or intra-venous.

Further disclosed herein is a method to treat or ameliorate conditions for which increase in expression of intermediate-conductance $Ca^{2+}$ activated $K^+$ channel is to be effective to treat or ameliorate the conditions in a subject.

Further disclosed herein is a medicament to treat or ameliorate conditions for which increase in expression of intermediate-conductance $Ca2^+$-activated $K^+$ channel is to be effective treat or ameliorate the conditions in a subject, wherein the medicament comprises engineered stem cells overexpressing intermediate-conductance $Ca2^+$-activated $K^+$ channel or cellular products produced and/or secreted by the engineered stem cells overexpressing intermediate-conductance $Ca2^+$-activated $K^+$ channel, or a combination thereof.

Further disclosed herein is a method to treat or ameliorate conditions for which the administration of engineered stem cells having increase in expression of intermediate-conductance Ca2+-activated K+ channel is indicated.

BRIEF DESCRIPTION OF THE DRAWINGS

FIGS. 1A-B show original whole cell currents from CD90$^+$ and CD90$^-$ EDCs recorded in the presence of 300-nmol/L free-$[Ca^{2+}]_i$ with 300-ms voltage step protocol from −120 mV to +60 mV (20 mV increment) with a holding potential of −40 mV. FIG. 1C shows the I-V relationship of whole-cell ion currents in CD90$^+$ and CD90$^-$ EDCs recorded in the presence of 300-nmol/L free-$[Ca^{2+}]_i$ with 1000-ms voltage ramps from −120 mV to +60 mV with a holding potential of −40 mV. FIG. 1D shows reversal potential of whole-cell ion currents recorded in CD90$^+$ and CD90$^-$ EDCs. Non-paired student t-test; n/N=cells/cell lines per group;

FIGS. 2A-D show the functional KCa current expressed in EDCs. FIG. 2A shows original whole cell currents from CD90$^+$ (upper panel) and CD90$^-$ EDCs (lower panel) after addition of 1 μmol/L paxilline with 300-ms voltage step protocol from −120 mV to +60 mV (20 mV increment). FIG. 2B shows the I-V relationship of whole-cell ion currents in CD90$^+$ and CD90$^-$ EDCs after addition of 1 μmol/L paxilline with 1000-ms voltage ramps from −120 mV to +60 mV with a holding potential of −40 mV. FIG. 2C shows the original whole cell currents from CD90$^+$ (upper panel) and CD90$^-$ EDCs (lower panel) after addition of both 1 μmol/L paxilline and 1 μmol/L TRAM-34 with 300-ms voltage step protocol from −120 mV to +60 mV (20 mV increment). FIG. 2D shows the I-V relationship of whole-cell ion currents in CD90$^+$ and CD90$^-$ EDCs after addition of both 1 μmol/L paxilline and 1 μmol/L TRAM-34 with 1000-ms voltage ramps from −120 mV to +60 mV with a holding potential of −40 mV. Two-way repeated-measures ANOVA with individual-mean comparisons by Bonferroni-corrected t-tests; n/N=cells/cell lines per group;

FIGS. 3A-D show the functional endogenous KCa3.1 current and membrane-potential changes during SOCE in EDCs. FIG. 3A shows the I-V relationship of $I_{KCa3.1}$ (TRAM-34-sensitive current) in CD90$^+$ and CD90$^-$ EDCs. FIGS. 3B show the resting potential of EDCs before and after exposure to 1 μmol/L TRAM-34. Two-way repeated-measures ANOVA with individual-mean comparisons by Bonferroni-corrected t-tests; n/N=cells/cell lines per group. FIG. 3C shows the original current-clamp recording from one CD90$^+$ cell (left panel) and mean±SEM data for $V_{mem}$ changes induced by SOCE and subsequent exposure to 1 μmol/L TRAM-34 (right panel). FIG. 3D shows the original current-clamp recording from one CD90$^-$ cell (left panel) and mean±SEM data for $V_{mem}$ changes induced by SOCE and subsequent exposure to 1 μmol/L TRAM-34 (right panel). One-way ANOVA with individual-mean comparisons by Bonferroni-corrected t-tests; numbers shown on bars are numbers of cells studied; n/N=cells/cell lines per group;

FIG. 4A shows the mean±SEM KCNN4-gene expression in EDCs following lentivirus-mediated KCNN4-gene transfer or empty vector (EV) (MOI=20). FIG. 4B shows the I-V relationship of $I_{kca3.1}$ currents recorded under various experimental conditions. FIG. 4C shows the resting potential of EDCs under various experimental conditions, before and after exposure to 1 μmol/L TRAM-34. FIG. 4D shows the representative Fluo-4 images in EV- and KCNN4-transduced EDCs over-expression on basal intracellular $Ca^{2+}$ level. Paired student t-test; N=biological samples (panel A); two-way repeated-measures ANOVA with individual-mean comparisons by Bonferroni-corrected t-tests; n/N=cells/cell lines per group (panel C);

FIGS. 5A-C show the effects of KCNN4 over-expression on EDC phenotype after 24 hours exposure to 1% oxygen in basal media culture conditions. FIG. 5A shows that the increasing $I_{KCa3.1}$ boosts EDC cell numbers from baseline (n=5). *p<0.05 vs. EV and NT EDCs. FIG. 5B shows that the KCNN4 over-expression increases the proportion of EDCs actively proliferating (n=5). *p<0.05 vs. EV and NT EDCs. Arrows indicate Ki67$^+$cells. Scale bar, 100 μm. DAPI, 4',6-diamidino-2-phenylindole. FIG. 5C shows that the increasing $I_{KCa3.1}$ had no effect on the ability of EDCs to withstand apoptosis as indicated by expression of apoptotic (Annexin V+/7AAD-) and necrotic (Annexin V+/7AAD+) markers (n=5). 7AAD, 7-aminoactinomycin D;

FIG. 6A shows the I-V relationship of $I_{BKCa}$ (paxilline-sensitive current) in CD90$^+$ and CD90$^-$ EDCs. FIG. 6B shows the resting potential of EDCs before and after exposure to 1 μmol/L paxilline. Two-way repeated-measures ANOVA with individual-mean comparisons by Bonferroni-corrected t-tests; n/N=cells/cell lines per group;

FIG. 7A shows representative images of flow cytometry plots for von Willebrand factor (vWF), alpha smooth muscle actin (aSMA) and cardiac troponin T (cTNT) before and after 1 week of culture within cardiogenic differentiation media (CDM). FIG. 7B shows grouped data demonstrating the effect of KCNN4 over-expression on the cardiogenic potential of EDCs. *p<0.05 vs. baseline. † p<0.05 vs. EV-EDCs or NT-EDCs after 1 week of culture within CDM;

FIGS. 8A-B show the effects of KCNN4 over-expression on myocardial function. FIG. 8A is a schematic of in vivo experiments comparing the effect of KCNN4 engineered human EDCs (KCNN4 EDCs) to empty vector human EDCs (EV EDCs), non-transduced human EDCs (NT EDCs) and vehicle using a NOD/SCID IL2Rγ model of ischemic injury. LCA, left coronary ligation. FIG. 8B shows the effects of KCNN4 EDCs (n=12), EV EDCs (n=12), NT EDCs (n=13) or vehicle (n=14) injection on echocardiographic ejection fraction 4 weeks after LCA ligation. (C) Invasive hemodynamic measures of myocardial function 4 weeks after LCA ligation;

FIGS. 10A-E show the effects of KCNN4 over-expression on fibrosis, neo-angiogenesis, cardio-myogenesis and long-term engraftment. FIG. 10A shows scar size analysis 4 weeks after LCA ligation (n=5). FIG. 10B shows quantification of infarct wall thickness and viable tissue within the risk area (n=5). FIG. 10C shows quantitative PCR analysis for human ALU sequences 21 days after EDC injection (n=9) FIG. 10D shows vessel density within the peri-infarct area as indicated (white arrows) using isolectin B4 (red) and DAPI (blue) immunohistochemistry (n=5). Scale bar, 100 μm. FIG. 10E shows the total number of BrdU positive cells (white stars), proliferating cardiomyocytes (BrdU$^+$/cTNT$^+$) and non-cardiomyocyte cells (BrdU$^+$/cTNT$^-$) quantified using random field analysis of immunohistochemistry staining with BrdU (red), cTNT (green) and DAPI (blue; n=5). Scale bar, 100 μm. *p<0.05 vs. vehicle treated mice, † p<0.05 vs. EV and NT treated mice;

FIG. 12A shows BrdU$^+$ cells denoted with a white star. Scale Bar 50 μm. FIG. 12B shows representative z-stacks images of BrdU$^+$ cells demonstrating nuclear localization within BrdU$^+$ cells;

FIGS. 13A-B show the electrophysiological effects of EDC or vehicle treatment on mice. FIG. 13A shows telemetry demonstrating induction of ventricular tachycardia in mice treated with vehicle. FIG. 13 B shows the effect of EDC or vehicle treatment on ventricular refractoriness;

FIGS. 14A-E show the effects of KCNN4 over-expression on the paracrine profile of EDCs. FIG. 14A shows a direct comparison of cytokine proteomic expression within 39 cytokines found to be elevated within media conditioned by EV or KCNN4 EDCs. *p<0.05 vs EV or KCNN4 EDCs. BAFF, B-cell activating factor; BDNF, Brain-derived neurotrophic factor, CC C5/C5a, Complement Component C5a; Dkk-1, Dickkopf-related protein 1; DPPIV, Dipeptidyl peptidase-4; ENA-78, Epithelial-neutrophil activating peptide; FGF-' 9, Fibroblast growth factor 19; GDF-15, Growth/differentiation factor 15; GROα, Growth-regulated oncogene alpha; HGF, hepatocyte growth factor; ICAM-1, Intercellular Adhesion Molecule 1; IGBP-2, Insulin-like growth factor-binding protein; IGBP-3, Insulin-like growth factor-binding protein; IL-6, Interleukin-6; IL-8, Interleukin-8; IL-11, Interleukin-11; IL-17A, Interleukin-17A; IL-19, Interleukin-19; IL-22, Interleukin-22; MCP-1, Monocyte chemoattractant protein-1; MIF, Macrophage migration inhibitory factor; RBP-4, Retinol binding protein 4; TFF3, Trefoil factor 3; uPAR, Urokinase-type plasminogen activator receptor; VEGF, Vascular endothelial growth factor; Vitamin D BP, Vitamin D binding protein. FIG. 14B shows the relative abundance of the top 10 cytokines produced by KCNN4 and EV EDCs. FIG. 14C shows a comparison of the size distribution of extracellular vesicles within EDC conditioned media. FIGS. 14D-E each show the effects of KCNN4 over-expression on the miRNA expression profile of NT EDCs. (FIG. 14D) or EV EDCs (FIG. 14E). *p<0.05 vs EV or KCNN4; FIG. 15A shows pathways associated with downregulated miRNAs in EVs isolated from KCNN4 EDCs compared to NT EDCs. FIG. 15B shows pathways associated with downregulated miRNAs in EVs isolated from KCNN4 EDCs compared to EV EDCs. FIG. 15C shows pathways associated with upregulated miRNAs in EVs isolated from KCNN4 EDCs compared to EV EDCs (mirPath v.3 using DIANA Tools).

DETAILED DESCRIPTION OF EXAMPLE EMBODIMENTS

Figure 1A:
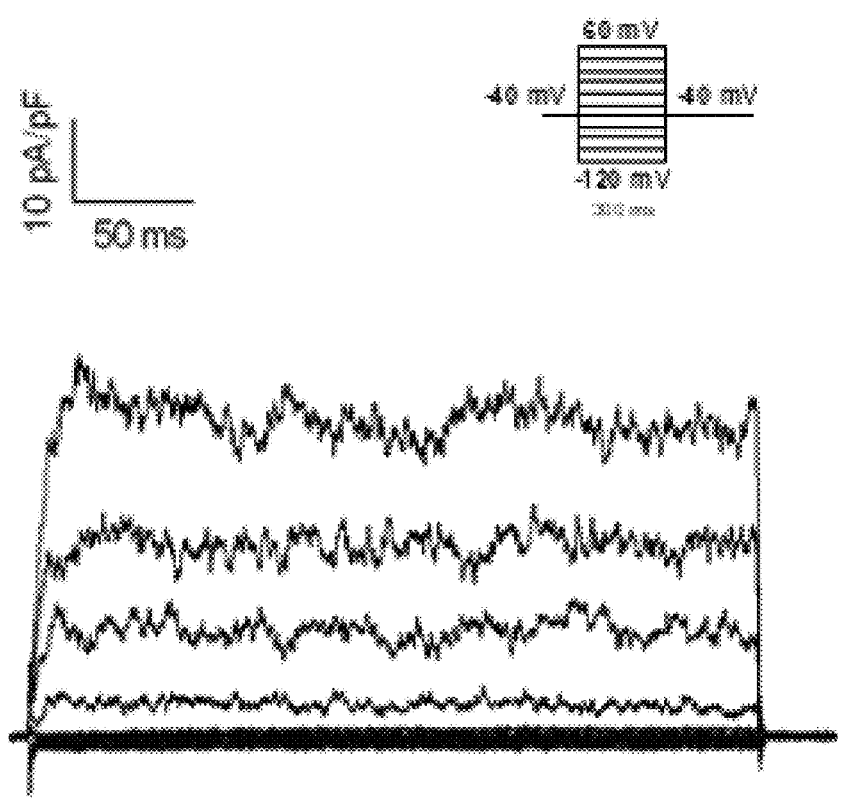
FIGS. 1A-D show the endogenous ionic currents expressed in EDCs.

Reference will be made below in detail to exemplary embodiments of the invention, examples of which are illustrated in the accompanying drawings. Wherever possible, the same reference numerals used throughout the drawings refer to the same or like parts.

As used herein, the following terms and phrases shall have the meanings set forth below. Unless defined otherwise, all technical and scientific terms used herein have the same meaning as commonly understood to one of ordinary skill in the art to which this invention belongs. Although any methods and materials similar or equivalent to those described herein can be used in the practice or testing of the invention, non-limiting methods and materials are now described.

The singular forms "a," "an," and "the" include plural reference unless the context clearly dictates otherwise. By way of example, "an element" means one element or more than one element.

As used herein, the term "allogeneic" refers to cells being genetically different, but deriving from the same species.

As used herein, the term "autologous" refers to tissue, cells or stem cells that are derived from the same subject's body.

As used herein, the term "cytokine" is used interchangeably with "growth factor" and refers to peptides or proteins that bind receptors on cell surfaces and initiate signaling cascades thus influencing cellular processes.

A "damaged myocardium" refers to myocardial cells which have been exposed to ischemic conditions. These ischemic conditions may be caused by a myocardial infarction, or other cardiovascular disease or related complaint. The lack of oxygen causes the death of the cells in the surrounding area, leaving an infarct, which will eventually scar.

As used herein, "extracellular vesicle" or "exosome" refers to lipid bilayer vesicles that are enriched in a variety of biological factors, including cytokines, growth factors, transcription factors, lipids, and coding and non-coding nucleic acids that are secreted by a wide range of cell types. The extracellular vesicles also contain mRNA and/or microRNA associated with signaling processes. In some embodiments, the bilayer membrane provides a protected and controlled internal microenvironment that allows contents to persist or migrate in the bloodstream or within tissues without degradation. The release of the contents into the extracellular environment allows for interaction with recipient cells via adhesion to the cell surface mediated by lipid-ligand receptor interactions, internalization via endocytic uptake, or by direct fusion of the vesicles and cell membrane, which lead to the release of extracellular vesicle content into the target cell(s).

As used herein, the term "gene" or "recombinant gene" refers to a nucleic acid comprising an open reading frame encoding a polypeptide, including both exon and (optionally) intron sequences.

As used herein, the term "heart failure" refers to the loss of cardiomyocytes such that progressive cardiomyocyte loss over time leads to the development of a pathophysiological state whereby the heart is unable to pump blood at a rate commensurate with the requirements of the metabolizing tissues.

As used herein, the term "heterologous" refers to tissue, cells or stem cells that are derived from the different species.

As used herein, the term "homologous" refers to tissue, cells or stem cells that are derived from the same species.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides. Preferred polynucleotides include those encoding an intermediate-conductance $Ca^{2+}$-activated $K^+$ channel (SEQ ID No: 3), or functional fragment thereof. Wherein the functional fragment is meant a portion of an amino acid sequence (or polynucleotide encoding that sequence) that has at least about 80%, preferably at least about 95% of the function of the corresponding full-length amino acid sequence (or polynucleotide encoding that sequence). Methods of detecting and quantifying functionality in such functional fragments are known and include the standard electrophysiological assays disclosed herein. In some embodiments, the polymeric molecules (e.g., a nucleic acid sequence or a polypeptide sequence) of the present disclosure are considered "homologous" if their sequences are at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% identical. The term "percent sequence identity" or "identical" in the context of nucleic acid sequences, for example, refers to the residues in the two sequences which are the same when aligned for maximum correspondence. Polynucleotide sequences can be compared using the computer program, BLAST (Altschul et al., *J. Mol. Biol.* 215:403-410 (1990); Gish and States, *Nature Genet.* 3:266-272 (1993), or similar programs. The term "substantial homology" or "substantial similarity," when referring to a nucleic acid or functional fragment thereof, indicates that, when optimally aligned with appropriate nucleotide insertions or deletions with another nucleic acid (or its complementary strand), there is nucleotide sequence identity in at least about 70%, 80%, 85%, or at least about 90%, or at least about 95%, 96%, 97%, 98% or 99% of the nucleotide bases, as measured by any well-known algorithm of sequence identity, such as BLAST, as discussed above.

The phrase "operably linked" as used herein means that the promoter is in the correct location and orientation in relation to a polynucleotide to control the initiation of transcription by RNA polymerase and expression of the polynucleotide.

As used herein, "patient" or "subject" may encompass any vertebrate including mammals, but not limited to humans, non-human primates, rats, and mice. In a preferred embodiment, the mammal is a human.

As used herein, the term "pharmaceutically acceptable carrier" is meant herein a material that is not biologically or otherwise undesirable, i.e., the material may be incorporated into a pharmaceutical composition administered to a patient without causing any undesirable biological effects or interacting in a deleterious manner with any of the other components of the composition in which it is contained. The choice of pharmaceutically acceptable carrier can be selected with regard to the intended route of administration and standard pharmaceutical practice.

Reference herein to a "promoter" or "promoter sequence" is to be taken in its broadest context and includes a DNA regulatory region capable of binding RNA polymerase in a cell and initiating transcription of a polynucleotide or polypeptide coding sequence such as messenger RNA, ribosomal RNAs, small nuclear of nucleolar RNAs or any kind of RNA transcribed by any class of any RNA polymerase. In one embodiment, the term "promoter" is also used to describe a synthetic or fusion molecule or derivative which confers, activates or enhances expression of an isolated nucleic acid molecule in a mammalian cell. Placing a sequence under the regulatory control of a promoter sequence means positioning said molecule such that expression is controlled by the promoter sequence. Promoters are generally positioned 5' (upstream) to the genes that they control. The promoter may regulate the expression of a sequence constitutively or in response to stimuli. The term "constitutive" when made in reference to a promoter means that the promoter is capable of directing transcription of an operably linked nucleic acid sequence in the absence of a specific stimulus. In the present context, the terms "in operable connection with" or "operably under the control" or similar such as "operably linked to" shall be taken to indicate that expression of the structural gene is under the control of the promoter sequence with which it is spatially connected in a cell.

As used herein, "protein" is a polymer consisting essentially of any of the 20 amino acids. Although "polypeptide" is often used in reference to relatively large polypeptides, and "peptide" is often used in reference to small polypeptides, usage of these terms in the art overlaps and is varied.

The term "therapeutically effective amount" as used herein refers to an amount that results in an improvement or remediation of the symptoms of the disease or condition.

"Transfection" is used to refer to the uptake of nucleic acid compositions by a cell. A cell has been "transfected" when an exogenous nucleic acid composition has crossed the cell membrane. A number of transfection techniques are generally known in the art. Such techniques can be used to introduce one or more nucleic acid compositions, such as a plasmid vector and other nucleic acid molecules, into suitable host cells. For purposes of this disclosure, "transduction" is a special form of "transfection" via a viral vector.

The term "treating" and "treatment" as used herein refers to administering to a subject a therapeutically effective amount of a composition so that the subject has an improvement in the disease. In some embodiments, "treating" and "treatment" refers to the reduction in severity and/or frequency of symptoms, elimination of symptoms and/or underlying cause, prevention of the occurrence of symptoms and/or their underlying cause, and improvement or remediation of damage. The pharmaceutical compositions of the present invention may be used as therapeutic agents—i.e. in therapy applications. As herein, the terms "treatment" and "therapy" include curative effects, alleviation effects, and prophylactic effects.

As used herein, the term "vector" refers to a nucleic acid molecule capable of transporting another nucleic acid to which it has been linked. Preferred vectors are those capable of autonomous replication and/or expression of nucleic acids to which they are linked. Vectors capable of directing the expression of genes to which they are operatively linked are referred to herein as "expression vectors".

Cardiac explant-derived cells (EDCs) have cardiogenic potential and a paracrine profile with cardioprotective capacity (3). EDCs are obtained as a heterogeneous mixture of complementary subpopulations expressing stem cell-related markers (e.g. c-Kit, ABCG2, SSEA-1), endothelial markers (e.g. CD31, CD34) and mesenchymal markers (e.g. CD90, CD105) (3). EDCs reduce pathological cardiac remodeling and promote myocardial repair (3-9). Recent evidence suggests that CD90⁻ cells are responsible for most of the functional benefits associated with EDC-therapy (3, 10).

Changes in membrane potential ($V_{mem}$) and intracellular $Ca^{2+}$($Ca^{2+}$i) can exert significant influence over stem cell properties (11). It has recently been shown that the function of resident cardiac c-Kit⁺ cells and bone marrow-derived mesenchymal stem cells (BM-MSCs) is governed by intermediate-conductance (KCa3.1) channels encoded by the KCNN4 gene (12) (SEQ ID No: 1). It has been found that KCa3.1 channels open in response to store-operated $Ca^{2+}$-entry (SOCE), a major signal for stem-cell activation, and hyperpolarize the cell membrane, thereby increasing the driving force for $Ca^{2+}$-entry, enhancing transmembrane $Ca^{2+}$-flux and optimizing the signal. KCa3.1-channel inhibition decreases cell-proliferation in association with reduced SOCE in both c-Kit+ cells and BM-MSCs (12).

Recent evidence shows endogenous ionic flows regulate much more than cell excitability and play a crucial role in cell proliferation, migration, growth and differentiation (58).

According to one embodiment, the modulation of bioelectric properties in a stem cell directs the stem cell phenotype toward therapeutic application. According to another embodiment, the therapeutic capacity of ex vivo expanded cells is influenced by plasma-membrane ion-channel function.

According to another embodiment, ex vivo preconditioning increases the therapeutic potential of ex vivo expanded stem cells. According to one embodiment, enhancing KCNN4 expression improves the therapeutic potential of stem cells by hyperpolarizing transmembrane potential to modulate Ca2+-dependent cell functions, including, but not limited to, proliferation, differentiation, cytokine secretion, and exosome production. In some embodiments, the ex vivo expanded stem cells are EDCs. In some embodiments, EDC function and therapeutic capacity is increased by over-expressing the KCa3.1 channel in the EDCs.

EXAMPLES

The following examples are intended to illustrate but not to limit the invention in any manner, shape, or form, either explicitly or implicitly. While they are typical of those that might be used, other procedures, methodologies, or techniques known to those skilled in the art may alternatively be used.

Cell Culture and Lentiviral Transduction

Human EDCs were cultured from left atrial appendages donated by patients undergoing clinically indicated heart surgery after informed consent under a protocol approved by the University of Ottawa Heart Institute Research Ethics Board. Explant-derived cardiac stem cells (EDCs) were cultured as previously described (3).

Briefly, cardiac biopsies were minced, digested (Collagenase IV, Thermo Fischer Scientific) and plated within Nutristem media (Biological industries) exposed to physiologic (5%) oxygen (13). Once a week for 4 weeks, EDCs that spontaneously emerged from the plated biopsy were collected using TrypLE Select (Thermo Fischer Scientific). Cells were transduced with lentivirus to over-express KCNN4 (OHS6085-213573573, GE Healthcare Dharmacon) (SEQ ID No: 2), empty backbone (25890, Addgene) or tagged with a fluorescent CD90 antibody (561969, BD Bioscience). Two days later, cells were harvested using TrypLE Select for direct experimentation.

As shown in Table S1, there were no significant differences in the characteristics of patient cell lines used for in vitro or in vivo experiments.

TABLE S1

Clinical characteristics.

| | Atrial Appendage donors in vitro study (n = 8) | Atrial Appendage donors in vivo study (n = 4) | P value |
|---|---|---|---|
| Age (yrs) | 65 ± 3 | 68 ± 4 | 0.73 |
| BMI (kg/m$^2$) | 30 ± 3 | 33 ± 3 | 0.58 |
| Gender (% male) | 75% | 50% | 0.54 |
| Diabetes | 25% | 0% | 0.51 |
| Hypertension | 100% | 50% | 0.09 |
| Dyslipidemia | 63% | 50% | 1.00 |
| Ongoing smoking | 25% | 50% | 0.54 |
| Thyroid disease | 25% | 25% | 1.00 |
| Peripheral vascular disease | 13% | 25% | 1.00 |
| Coronary artery disease | 100% | 75% | 0.33 |
| History of MI | 38% | 25% | 1.00 |
| Valvular heart disease | 50% | 50% | 1.00 |
| Congestive heart failure | 0% | 25% | 0.33 |
| NYHA class | 1.25 ± 0.3 | 2.7 ± 0.9 | 0.13 |
| LV Ejection Fraction (%) | 53 ± 7 | 47 ± 3 | 0.52 |
| CCS class | 1.8 ± 0.7 | 3 ± 0.1 | 0.37 |
| Creatinine (µmol/L) | 82 ± 8 | 76 ± 8 | 0.65 |
| Hemoglobin A1c | 5.8 ± 0.2 | 5.8 ± 0.3 | 1.00 |
| Medications: | | | |
| Anti-platelet therapy | 100% | 100% | 1.00 |
| Beta-blocker | 88% | 50% | 0.23 |
| Statins | 88% | 25% | 0.07 |
| ACEI or ARB | 88% | 50% | 0.23 |

BMI = Body Mass Index;
MI = Myocardial infarction;
NYHA = New York Heart Association;
LV = Left ventricle;
CCS = Canadian Cardiovascular Society;
ACEI = Angiotensin-converting enzyme inhibitor;
ARB = Angiotensin receptor blocker.

Ion-Current and $V_{mem}$ Recording

All in vitro recordings were obtained at 37° C. Whole-cell perforated-patch and tight-seal techniques were used to record membrane potential ($V_{mem}$, current-clamp mode) and ion-currents (voltage-clamp mode). Borosilicate glass electrodes (tip resistances 2-3 MΩ when filled with pipette-solution) were connected to a patch-clamp amplifier (Axopatch 200B; Axon Instruments). $I_{KCa3.1}$ was recorded as 1-µmol/L TRAM-34-sensitive current, and $I_{BKCa}$ as 1-µmol/L paxilline-sensitive current. Tyrode solution contained (mmol/L) NaCl 136, CaCl$_2$ 1.8, KCl 5.4, MgCl$_2$ 1, NaH$_2$PO$_4$ 0.33, dextrose 10, and HEPES 5, titrated to pH 7.4 with NaOH. For nominally Ca$^{2+}$-free Tyrode solution experiments, CaCl$_2$ was omitted and 1 mM EGTA was added. The pipette solution used to define global ion-current profiles contained (mmol/L) GTP 0.1, potassium-aspartate 110, KCl 20, MgCl$_2$ 1, MgATP 5, HEPES 10, sodium-phosphocreatine 5, and EGTA 5 (pH 7.4, KOH). For $I_{KCa3.1}$ recording, the pipette solution contained (mmol/L) KCl 130, NaCl 5, MgCl$_2$ 1, K$_2$ATP 5, HEPES 10 and EGTA 5 (pH 7.2, KOH). The amount of CaCl$_2$ required to achieve 300-nmol/L free-[Ca$^{2+}$]$_i$ was determined with WebMaxC standard software (http://www.stanford.edu/~cpatton/webmaxc/webmaxcS.htm). Junction potentials between bath and pipette solution averaged 10 mV and were corrected before recording, for both $V_{mem}$ and ion-current measurements.

Currents are expressed as densities (pA/pF) to control for cell size/capacitance differences. To study the effect of store-operated Ca$^{2+}$-entry (SOCE) on $V_{mem}$, Ca$^{2+}$i was depleted passively by bathing cells in Ca$^{2+}$-free Tyrode solution for at least 30 minutes, and then cell-contents were dialyzed by tight-seal attachment with pipette solutions containing (mmol/L) KCl 140, NaCl 5, MgCl$_2$ 1.2 and HEPES 10 (pH 7.2, KOH). After whole-cell configuration and cell-dialysis were established, extracellular [Ca$^{2+}$] was restored and $V_{mem}$ changes were recorded.

Ca$^{2+}$-Imaging

EDCs genetically engineered to over-express KCNN4 (KCNN4 EDCs) and empty backbone-transduced EDCs (EV EDCs) were loaded with Fluo-4-acetoxymethyl ester (10-µmol/L; Invitrogen) in complete growth medium in the presence of Pluronic F-127 (20% solution in dimethyl-sulfoxide, 2.5-µg/mL) for 30 minutes at 37° C. in a humidified incubator under standard cell culture conditions. Chamber slides were positioned on the stage of a confocal microscope; cells were incubated with Tyrode solution and maintained for 15 minutes at room temperature before experimental protocols to allow deesterification of Fluo-4-acetoxymethyl ester. Fluo-4 was excited at 488 nm; emitted fluorescence was collected at 495 nm. High power field images were acquired with a confocal microscope (Olympus IX81). Basal intracellular Ca$^{2+}$ level was assessed in both groups. Images were analyzed with ImageJ software. Data are presented as mean fluorescence intensity relative to EV-EDCs.

Colorimetric, Flow Cytometric, Immunohistochemical, Proteomic and Extracellular Vesicle Evaluation EDC proliferation was measured in conditions designed to mimic the ischemic environment of the heart (1% oxygen, basal media without growth factors). Relative cell counts were evaluated using a colorimetric WST-8 assay (Cell Counting Kit-8, Dojindo) with confirmatory manual cell counts and random field analysis for Ki67/DAPI expression (12 visual field per cell line; ab156956, AbCam).

After 18 hours of culture in 1%-oxygen and in basal media conditions, EDCs and the culture medium were collected for analysis. Flow cytometry (Guava easyCyte, EMD Milipore) was used to evaluate cell viability with phycoerythrin-AnnexinA5 (PE-Annexin V) and 7-Amino-actinomycin D (7-AAD) (559763, BD Biosciences). The relative abundance of select cytokines within conditioned media was evaluated with Proteome Profiler Human XL Cytokine Array Kit (R&D Systems). Nanoparticle Tracking Analysis (Nanosight V2.3) was used to quantify extracellular vesicle content within conditioned media followed by multiplex fluorescent oligonucleotide-based miRNA detection (Human v3, Nanostring) to miRNA content within extracellular vesicles. Briefly, miRNeasy Micro Kit (QIAGEN) was used to extract total RNA with RNA quality/quantity measured with the Agilent 2100 Bioanalyzer (Agilent). Twenty-five nanograms of RNA were used for each reaction (Counter Human V3 miRNA Expression Assay, Nanostring). Image-quality control metrics were evaluated with nSolver (Nanostring); background subtraction was performed with the mean of negative controls plus two standard deviations. Normalized counts were obtained with trimmed-mean of M values (TMM) and differentially expressed miRNA identified with the generalized linear model (GLM) likelihood-ratio using EdgeR in the online DEBrowser tool (https://debrowser.umassmededu/). Heat maps were created in DEBrowser tool using the "complete" clustering method.

In Vivo Protocol

This protocol was reviewed and approved by the University of Ottawa Animal Care Committee. The detailed protocol was registered a priori within the Open Science Framework (https://osfio/nx2ck/). Male NOD/SCID IL2Rγ mice (8-9 weeks old; Charles River) were pre-treated with buprenorphine and anaesthetized with isoflurane under normothermic temperature control, for surgical left coronary artery (LCA) ligation. Seven days after LCA ligation, animals were randomized to echocardiographic guided intramyocardial injection of 100,000 KCNN4 EDCs, 100,000 EV EDCs, 100,000 unmodified EDCs (NT EDCs), or saline (i.e., vehicle-treated group) divided into two injections at the apex and ischemic border zone (5, 8, 9, 14). During the surgery and functional evaluation, mice were intubated, anesthetized with 2-3% isoflurane and maintained under physiologic temperature control. All animals were injected with buprenorphine (0.05 mg/kg subcutaneous) 1 hour prior to surgery and twice daily thereafter for 3 days. All mice were injected with bromodeoxyuridine (BrdU, 100 mg/kg IP daily) for 1 week after cell/vehicle injection.

All mice underwent echocardiographic imaging to confirm the effects of LCA ligation (1-week post LCA ligation) and cell therapy (21 days post-cell/vehicle injection). Twenty-eight days after cell/vehicle injection, mice underwent invasive hemodynamics or invasive electrophysiological study prior to sacrifice. Mice randomized to invasive hemodynamics underwent insertion of a 1.2F Millar catheter into the left ventricle via the right carotid artery. Transient vena caval occlusion to reduce preload was used to change the loading conditions and generate pressure-volume loops (15). Mice randomized to invasive electrophysiological testing underwent a thoracotomy to expose the apex of the heart prior to programmed electrical stimulation (MyoPacer EP, Ion Optix) via a platinum electrode placed on the apex of the left ventricle (16). A standard programmed electrical stimulation protocol was performed, consisting of 10 stimuli delivered at 100 ms intervals (S1, twice threshold, 2 ms) followed by a single extrastimulus (S2) starting at a coupling interval of 80 ms which then decremented by 2 ms until failure to capture defined the effective refractory period (ERP). If ventricular tachycardia or fibrillation were not induced, a second extrastimulus (S3) was introduced 80 ms after the shortest S2 that captured the ventricle. The S3 was then progressively decremented by 2-ms intervals until the ERP was reached. Finally, a third extrastimulus (S4) was introduced 80 ms after the last S3 that captured the ventricle and was then decremented by 2 ms intervals until the ERP was reached. If the mouse failed to develop ventricular arrhythmias with extrastimuli, the animal was deemed non-inducible. Infarct size was quantified using histological sections stained with Mason-Trichrome (ThermoFisher) in which sections at equivalent distances from the LCA surgical stitch were directly compared. Infarcted wall thickness was defined as the average of 5 left ventricular wall thickness measurements distributed equally within the infarcted left ventricular scar, while the ischemic risk region was defined as the area between the two edges of the infarct scar (17). Adjacent sections were used for immunohistochemical detection of capillary density (isolectin B4, B-1205, Vector Laboratories) or endogenous proliferation (BrdU, ab6326, Abcam) in conjunction with DAPI (Sigma-Aldrich) or troponin T (ab125266; Abcam) labelling. Human-cell engraftment was quantified using qPCR for retained human alu sequences (18, 19).

Statistical Analysis

All data are expressed as mean±SEM. Clampfit 10.4 (Axon Instruments) and GraphPad Prism 6.0 were used for data analysis. Multiple group comparisons were obtained with one-way ANOVA for non-repeated analyses in experiments involving more than 2 groups and two-way repeated-measures ANOVA for all multigroup analyses involving repeated measures. Individual-mean comparisons by Bonferroni-corrected t-tests were obtained to identify the statistical significance of individual-mean differences when overall group effects were noted. A 2-tailed $p<0.05$ was considered statistically significant. In all cases, variances were assumed to be equal and normality was confirmed prior to further post-hoc testing. If differences existed, Sidak's or Tukey's corrected t-test was used to determine the group(s) with the difference(s) (Prism v6). Differences in categorical measures were analyzed using Fischer's exact test. A final value of $p \leq 0.05$ was considered significant for all analyses.

Results

Endogenous Currents in Human EDCs

Figure 1B:
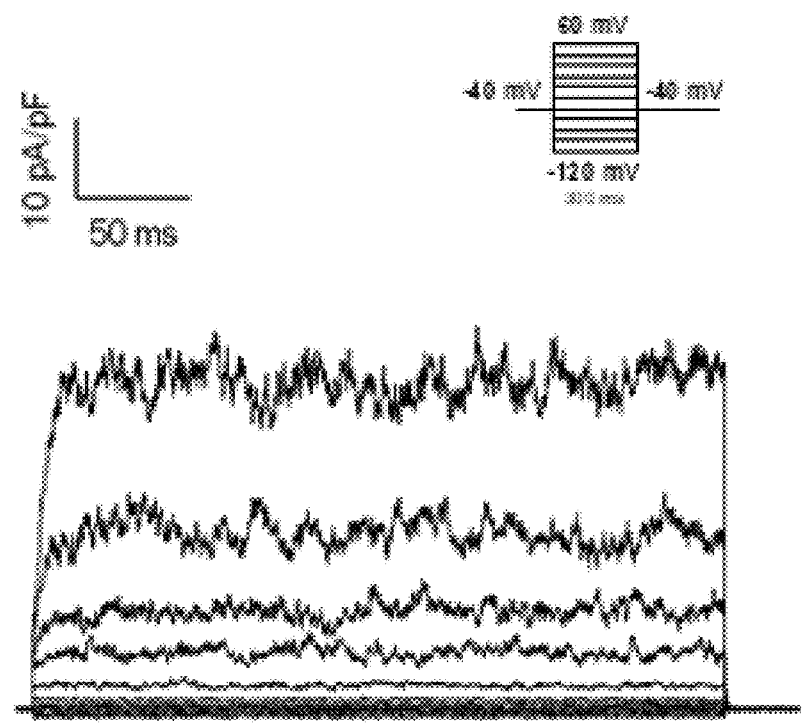
Figure 1C:
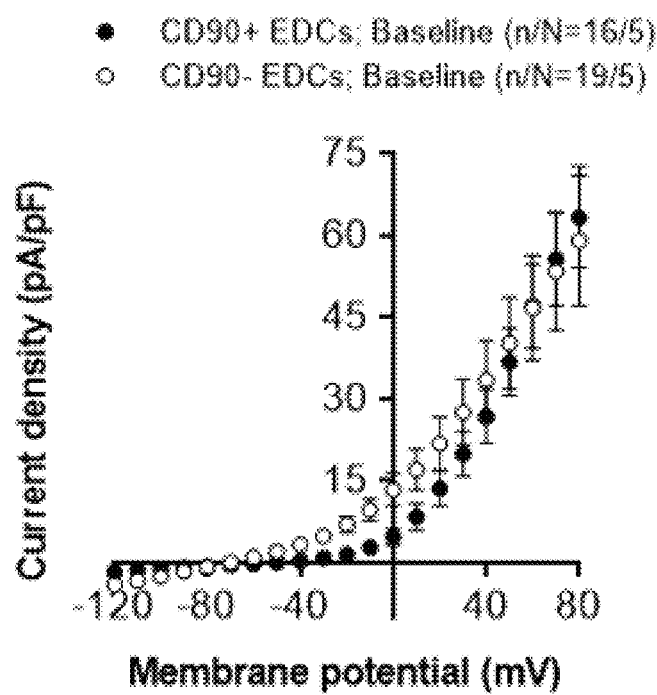
Figure 1D:
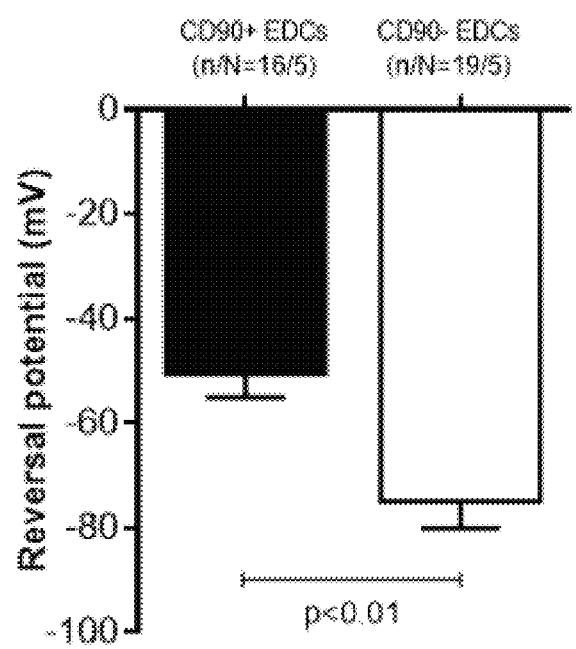

To characterize endogenous $Ca^{2+}$-activated $K^+$ channels ($K_{Ca}$) in EDC subpopulations, the $CD90^+$ subpopulation was fluorescently labeled before starting patch-clamp experiments. Under conditions that allow the activation of $Ca^{2+}$-dependent current, we recorded outwardly-rectifying voltage-dependent currents in both $CD90^+$ and $CD90^-$ cells (FIG. 1A). The reversal potential (Erev) of these currents averaged $-51\pm5$ mV and $-75\pm5$ mV ($p<0.01$) for $CD90^+$ and $CD90^-$ cells respectively (FIG. 1B). The differences in $E_{rev}$ hinted that the two subpopulations possess distinct bioelectrical properties, and thus different profiles of plasma-membrane ion-channels.

Types of $Ca^{2+}$-Dependent $K^+$ Currents and Contribution to $V_{mem}$

Figure 2B:
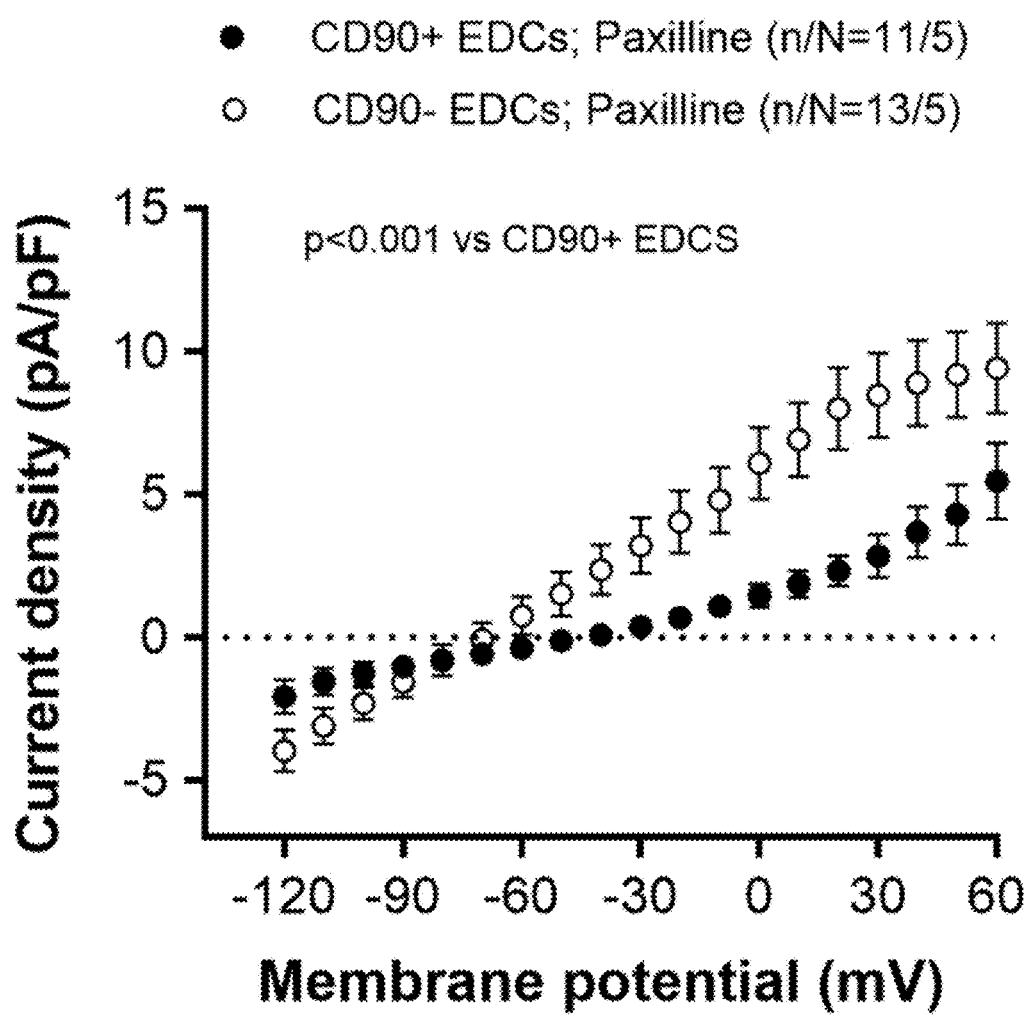
Figure 2D:
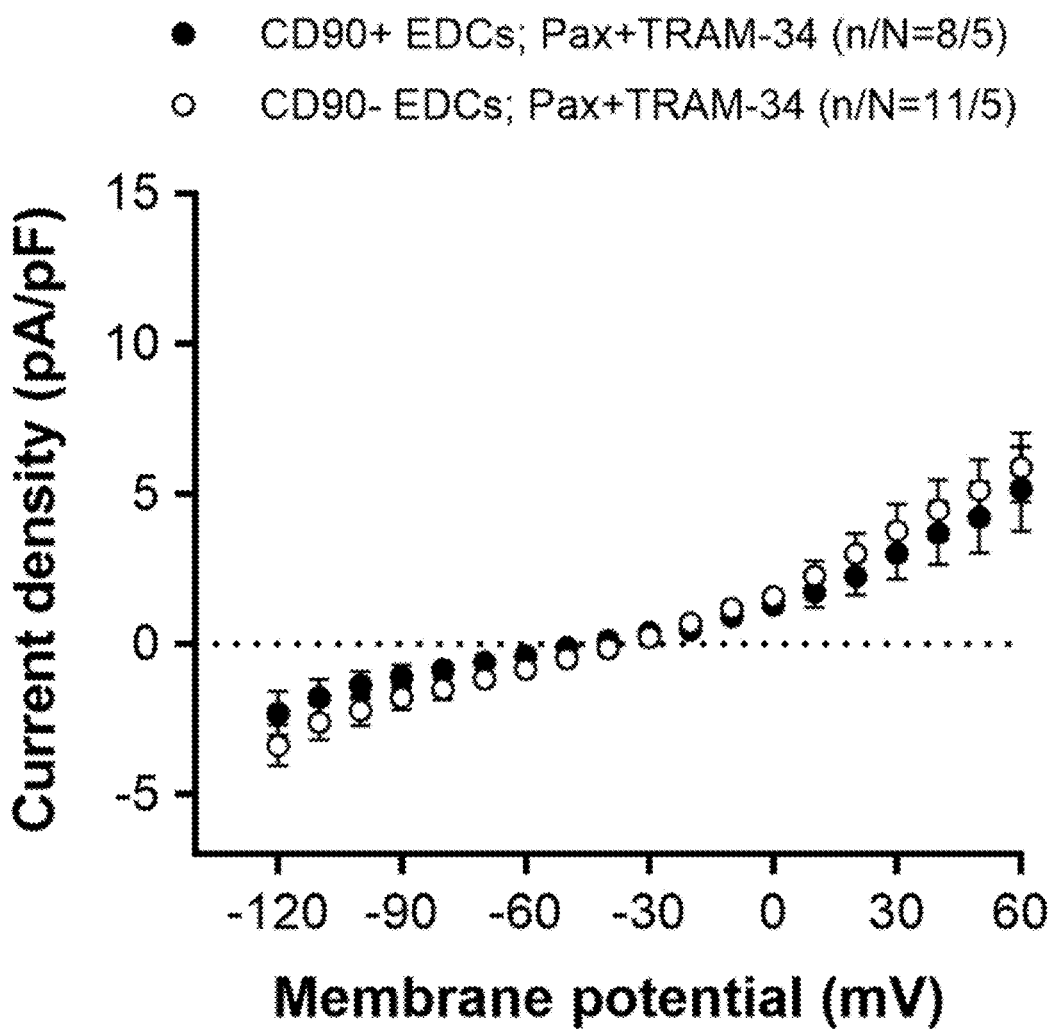
Figure 3A:
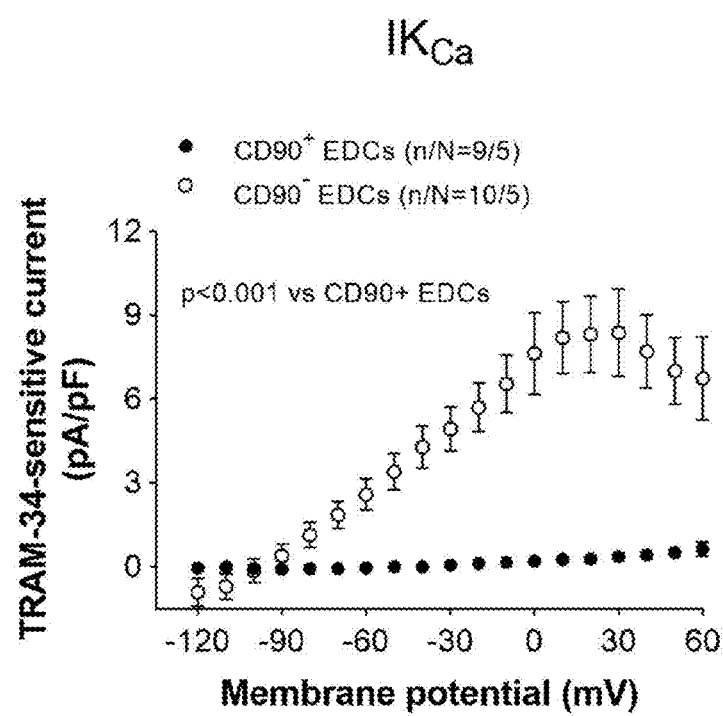
Figure 3B:
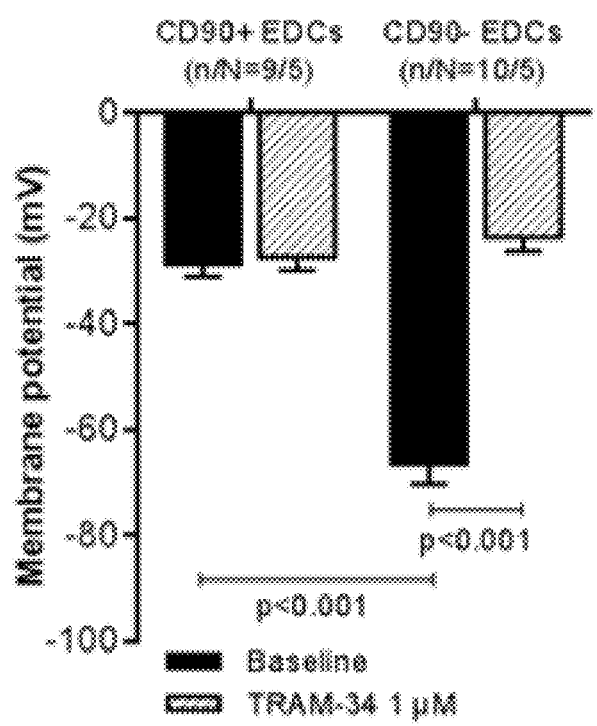
Figure 6A:
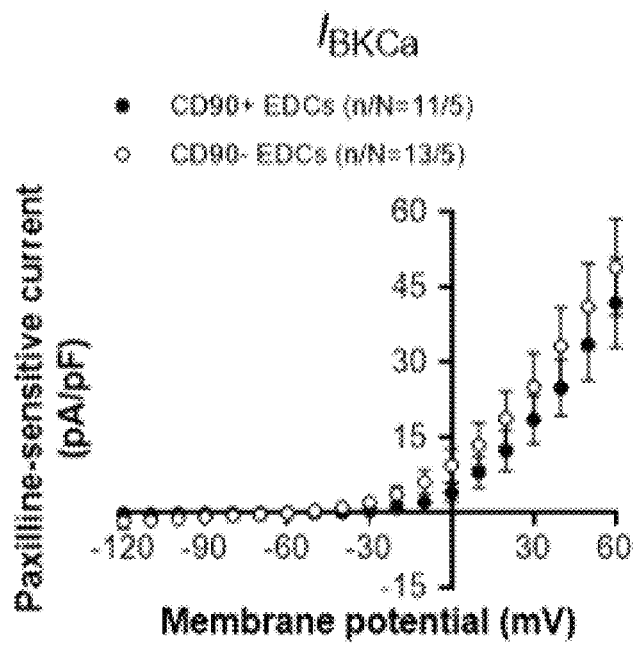
FIGS. 6A-B show the functional BKCa current expressed EDCs.
Figure 6B:
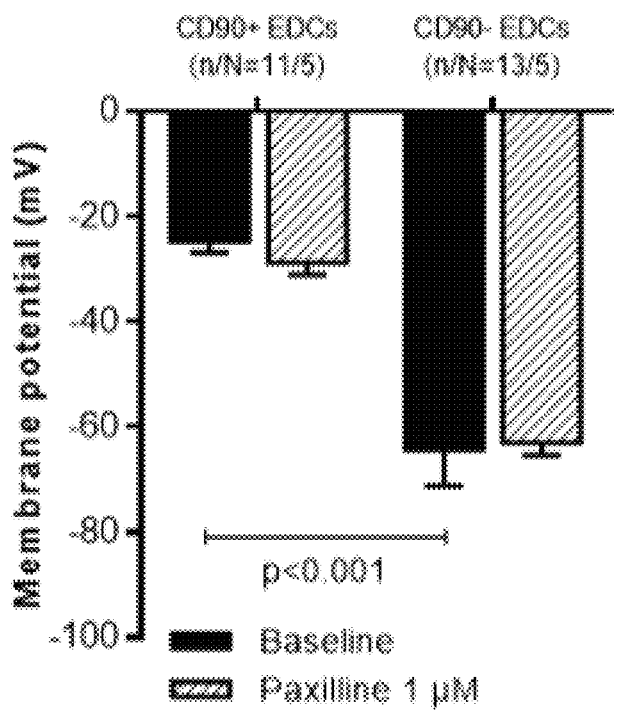

Since currents recorded in EDCs displayed some biophysical characteristics of the large-conductance $Ca^{2+}$-dependent $K^+$ current ($I_{BKCa}$), we tested the response to the selective $BK_{Ca}$-blocker paxilline. The outwardly-rectifying current-voltage (I-V) relationship of EDCs was strongly affected by paxilline, leaving a substantial inwardly-rectifying current in $CD90^-$ cells and a very small residual outwardly-rectifying current in $CD90^+$ cells (FIG. 2A-B). The paxilline-resitsant current in $CD90^-$ cells was time-independent and completely blocked by the selective $K_{Ca}3.1$-blocker TRAM-34 (FIG. 2C-D). The paxilline-sensitive current representing $I_{BKCa}$ was large and similar in both cell-types (FIG. 6A). $V_{mem}$ was significantly less negative in $CD90^+$ cells ($-25\pm2$ mV vs $-64\pm7$ mV; $p<0.001$) and was unaffected by paxilline (FIG. 6B), suggested that it is governed by another charge-carrier(s). In contrast to the $CD90^-$ subpopulation, KCa3.1 currents (TRAM-34-sensitive; $I_{KCa3.1}$) were undetectable in $CD90^+$ cells (FIG. 3A). Importantly, blocking KCa3.1 current substantially depolarized $V_{mem}$ of $CD90^-$ EDCs without altering $V_{mem}$ of $CD90^+$ cells (FIG. 3B). In the presence of TRAM-34, the $V_{mem}$ of $CD90^-$ EDCs became the same as that of $CD90^+$ cells. These results indicate that the $V_{mem}$ of EDCs is largely controlled by their $K_{Ca}3.1$ conductance, which is large in $CD90^-$ cells and undetectable in $CD90^+$ cells.

$V_{mem}$-Control by $Ca^{2+}$-Dependent $K^+$ Currents During $Ca^{2+}$-Entry

Figure 3D:
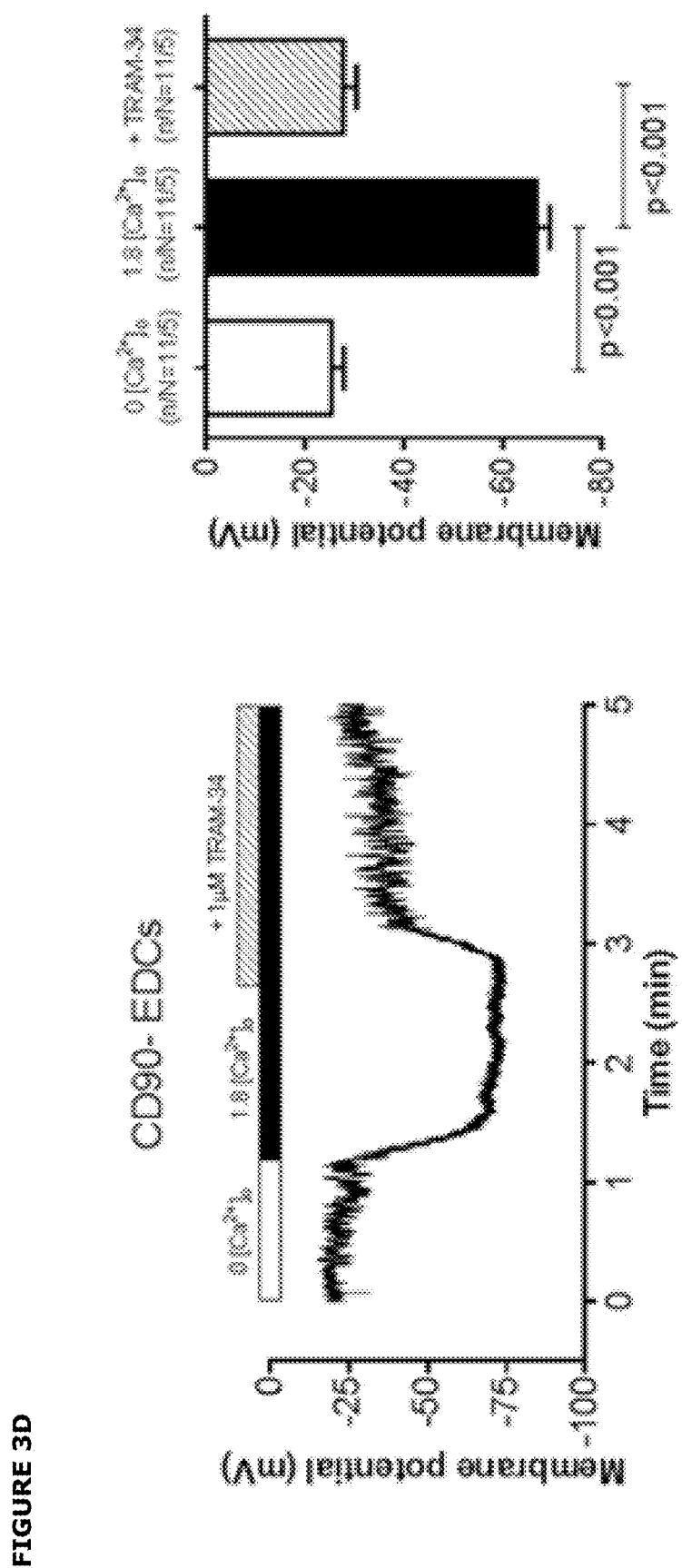

One potential role for KCa3.1 in EDCs would be hyperpolarization of $V_{mem}$ during store-operated $Ca^{2+}$-entry (SOCE), as previously demonstrated for $cKit^+$ and BM-MSCs (12). To address this possibility, we induced SOCE in EDCs and monitored $V_{mem}$ changes (FIG. 3C-D). In the presence of very low intracellular $[Ca^{2+}]$ ($[Ca^{2+}]_i$) resulting from perfusion with nominally $Ca^{2+}$-free extracellular solution, $V_{mem}$ was approximately −25 mV in both $CD90^+$ and $CD90^-$. Following store-depletion, the addition of 1.8-mmol/L extracellular $Ca^{2+}$ induced a strong hyperpolarization in $CD90^-$ cells (from −25±3 mV to −67±3 mV, p<0.001), but had no effect on $V_{mem}$ in $CD90^+$ cells. The addition of TRAM-34 during SOCE strongly inhibited the SOCE-associated hyperpolarization (FIG. 3D), indicating a key role for $I_{KCa3.1}$.

These observations are consistent with the notion that the differential expression of KCNN4 contributes to the reduced regenerative performance of $CD90^+$ cells (20, 21), while providing a potential target to enhance the effectiveness of EDC therapy.

Effect of KCNN4-Transfer on $V_{mem}$ and Intracellular $Ca^{2+}$ Level

Figure 4A:
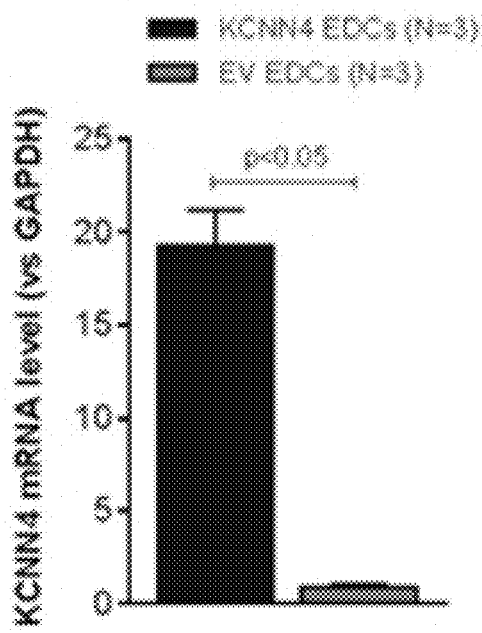
FIGS. 4A-D show the effects of KCNN4-gene transfer on KCa3.1 current and membrane-potential of EDCs.
Figure 4B:
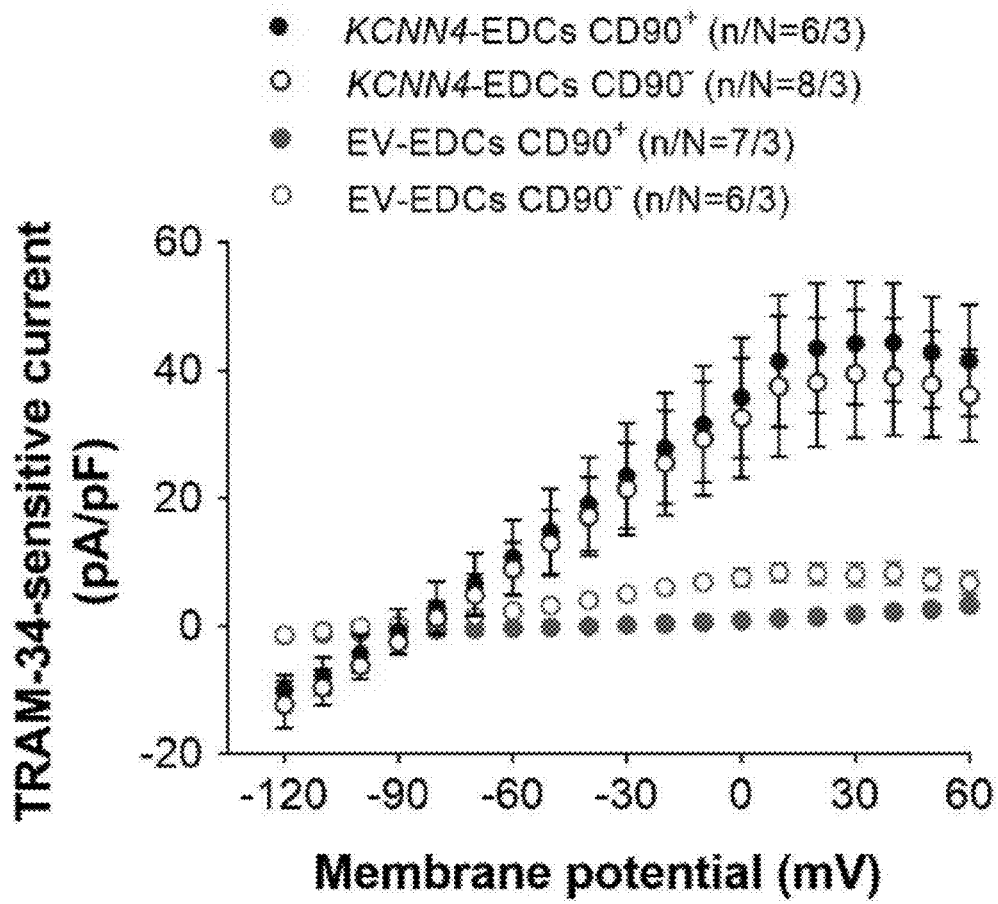
Figure 4C:
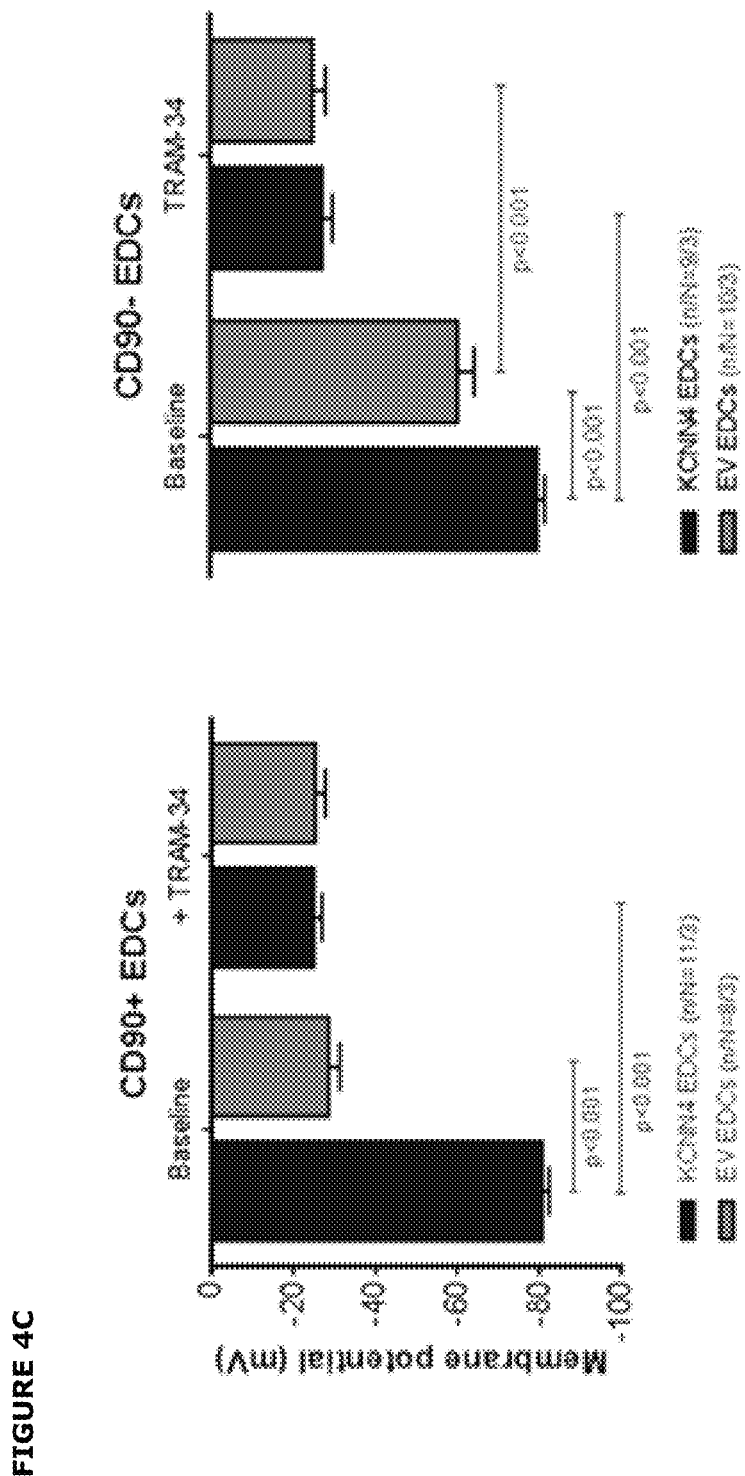
Figure 4D:
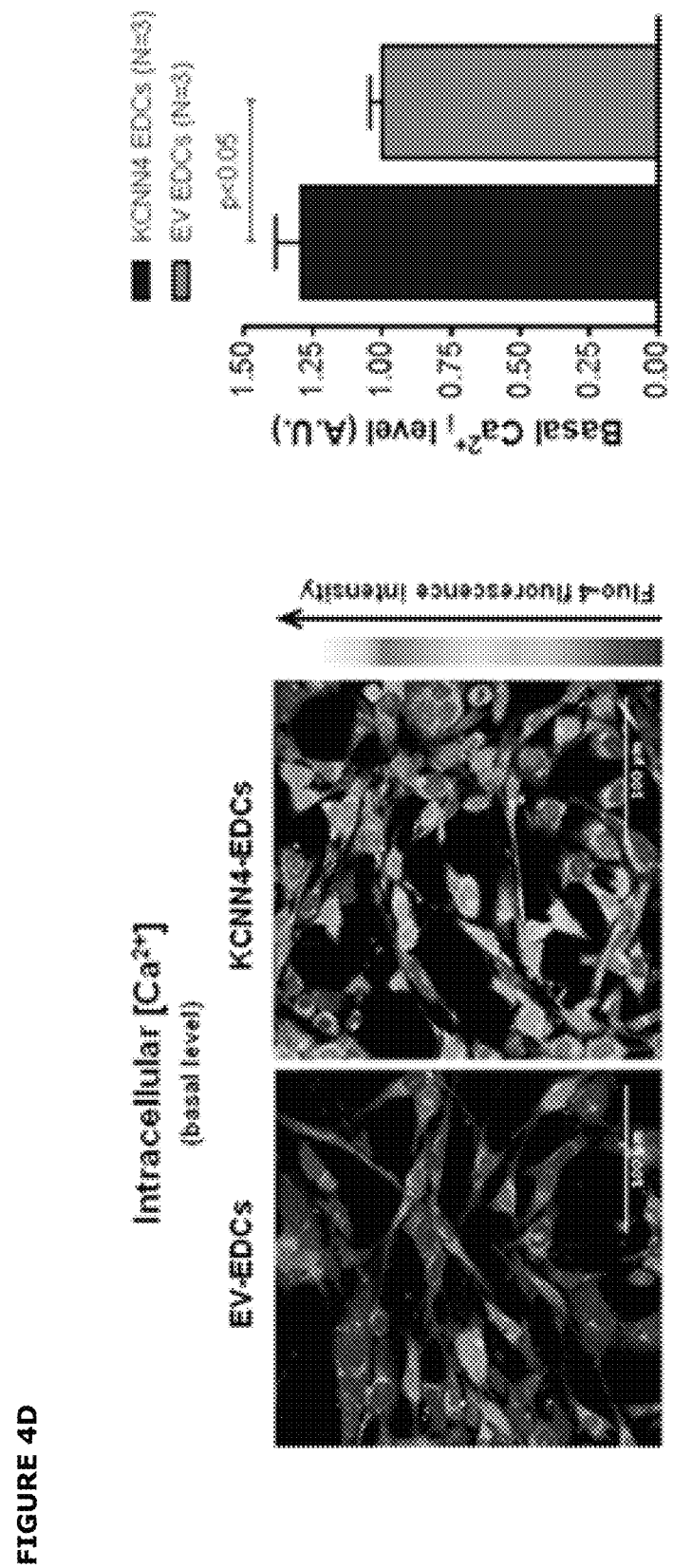

We engineered EDCs to overexpress KCa3.1 activity in EDCs prior to in vivo cell delivery. Lentivirus-mediated KCNN4-gene transfer increased KCNN4-gene expression about 20-fold compared to the empty vector (EV) (FIG. 4A). Importantly, KCNN4 overexpression confers a much more homogenous electrophysiological phenotype to EDCs. Indeed, KCNN4-transfer increased $I_{KCa3.1}$ density and hyperpolarized $V_{mem}$ to a similar level in both $CD90^+$ and $CD90^-$ cells (−77±2 mV vs −81±2 mV; FIG. 4B-C). Because $V_{mem}$ hyperpolarization is known to facilitate $Ca^{2+}$-entry through voltage-independent channels (22), we investigated whether KCNN4-transfer would affect $Ca^{2+}{}_i$. As shown, $Ca^{2+}{}_i$ was significantly higher under resting conditions in KCNN4-EDCs compared to control (FIG. 4D). Taken together, these results indicate that KCa3.1 over-expression enhances $Ca^{2+}$ signalling in EDCs.

Over-Expression of KCNN4 Increases Proliferation

Figure 7A:
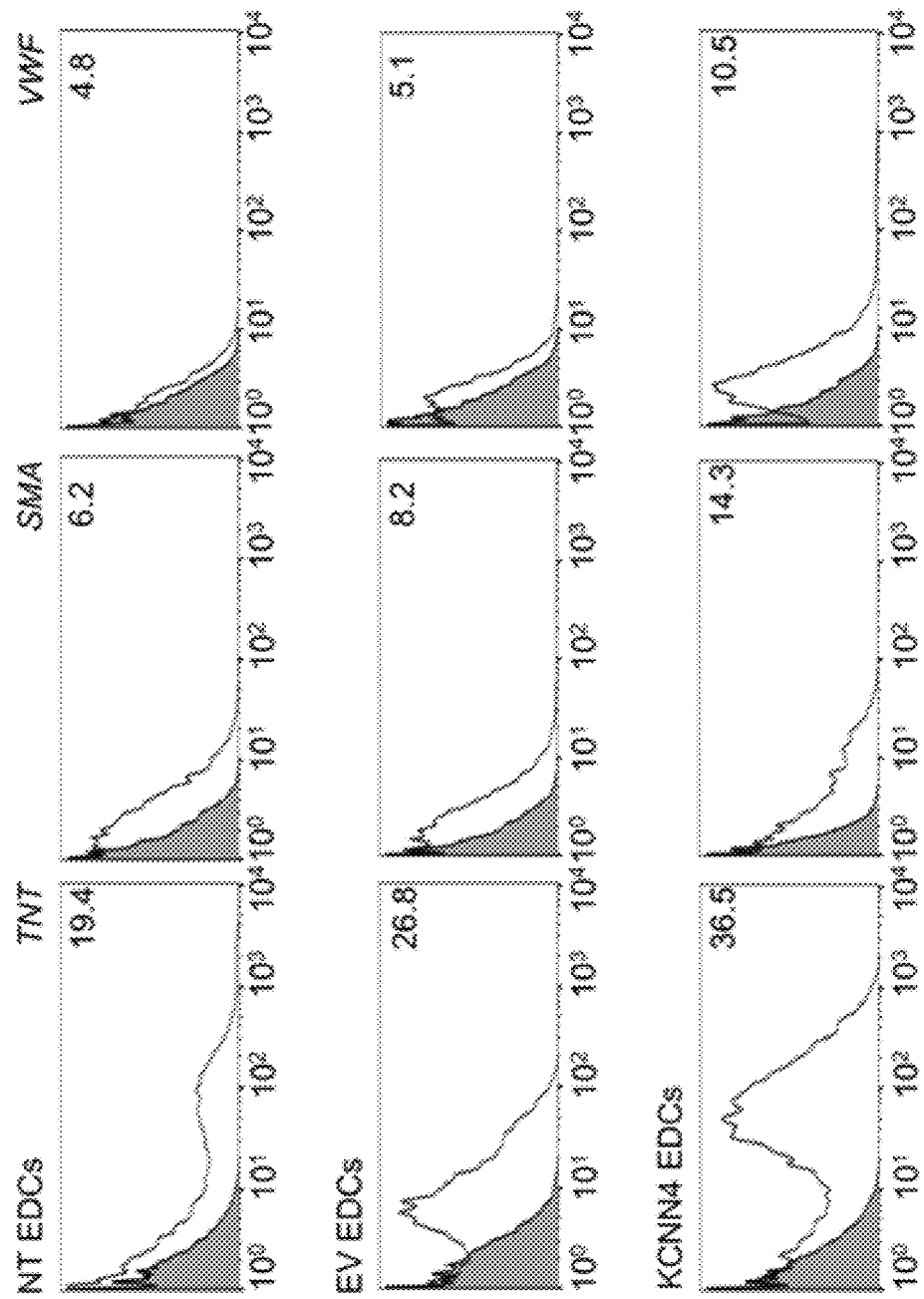
FIGS. 7A-B show the effect of KCNN4 engineering on EDC differentiation. EDCs were exposed to media conditions known to favor a cardiac lineage for 1 week prior to flow cytometric evaluation.
Figure 7B:
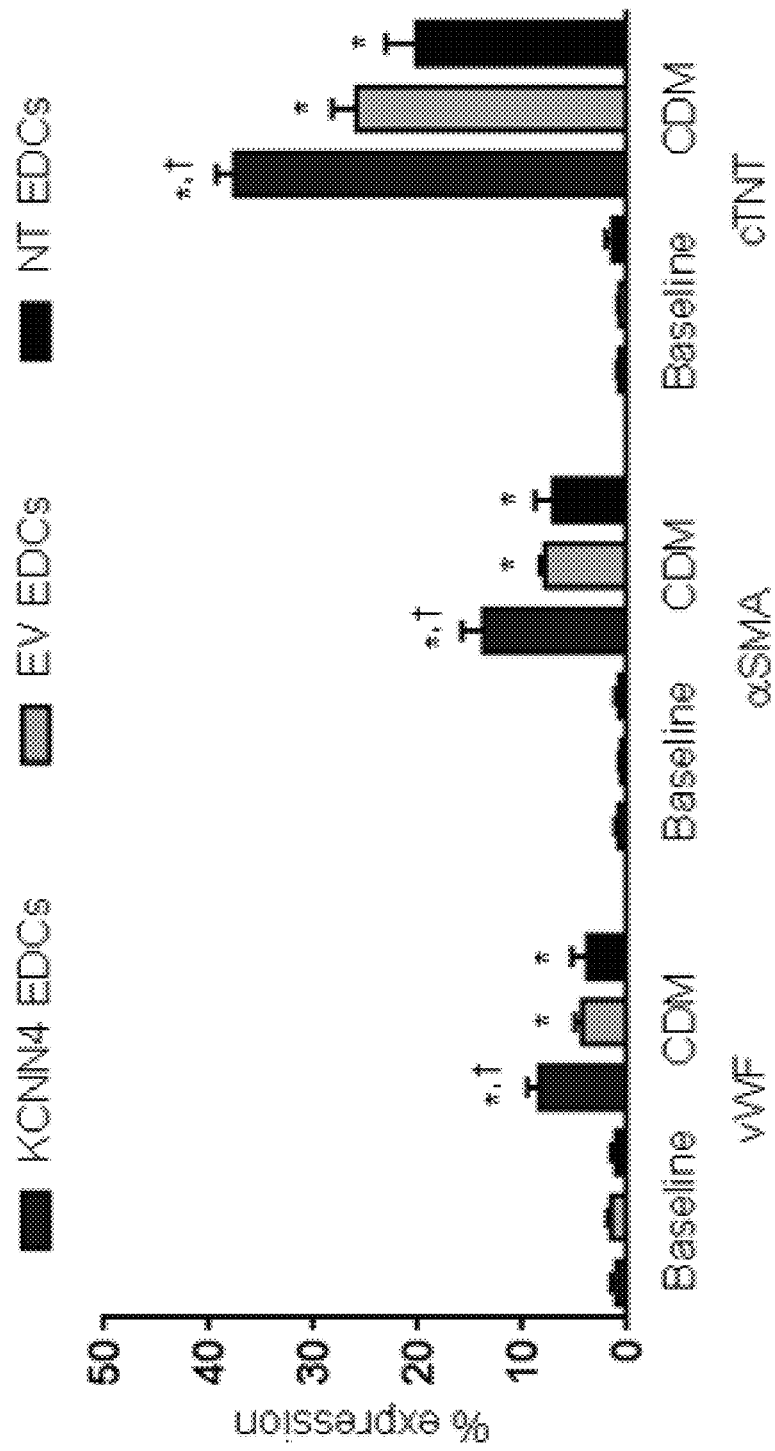
Figure 9:
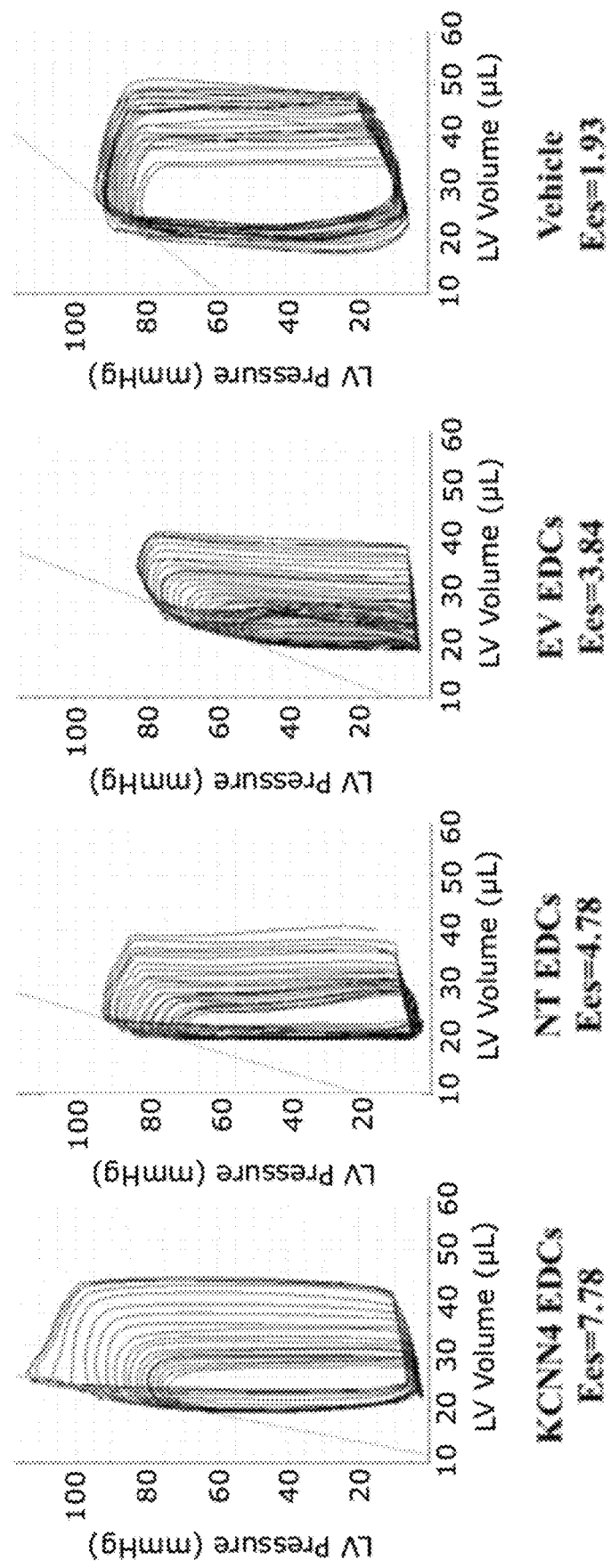
FIG. 9 shows the hemodynamic effects of transplanting KCNN4 engineered EDCs. Representative images of pressure volume loops generated during inferior vena cava compression from mice 3 weeks after receiving, KCNN4-EDCs, EV-EDCs, NT-EDCs or vehicle. Ees=end-systolic elastance.

When EDCs were exposed to in vitro culture conditions designed to mimic the harsh post-infarct environment (i.e., 1% oxygen+basal media), both EV and NT EDC numbers decreased from baseline (FIG. 5A), whereas over-expression of KCNN4 markedly increased proliferation (FIG. 5B) without conferring increased resistance to apoptosis (FIG. 3C). Despite ongoing constitutive expression of KCNN4, somatic gene transfer did not reduce the cardiogenic potential of EDCs (FIG. 7).

Transplant of KCNN4-Engineered EDCs Increases Cardiac Function

Male NOD/SCID IL2Rγ mice underwent LCA ligation, which was followed 1 week later by randomization to echocardiographically guided intra-myocardial injection of KCNN4 EDCs, EV EDCs, NT EDCs or vehicle (FIG. 8A). The time of intra-myocardial injection 1 week after LCA ligation is analogous to about 1 month after a clinical myocardial infarction in humans.

Lab staff were blinded to treatment allocations and all analysis was conducted by individuals blinded to group allotment. Group allocations were kept in a separate password protected list for unblinding after analysis of functional study outcome was completed. As shown in FIG. 8B and Table S2, all animals demonstrated equivalent degrees of pretreatment cardiac dysfunction and chamber dimensions 1 week after LCA ligation.

TABLE S2

Echocardiographic measures of left ventricular function.

| | | Endocardial Volume (μL) | | Stroke Volume | Ejection Fraction | Fractional Area Change | Cardiac Output |
|---|---|---|---|---|---|---|---|
| | | Diastolic | Systolic | (μL) | (%) | (%) | (mL/min) |
| 1 week post-LCA ligation | KCNN4 EDCs (n = 12) | 66.6 ± 1.8 | 44.2 ± 1.2 | 22.4 ± 0.8 | 33.6 ± 0.7 | 20.0 ± 0.5 | 9.0 ± 0.9 |
| | NT EDCs (n = 13) | 76.8 ± 4.9 | 51.4 ± 3.5 | 25.4 ± 1.6 | 33.3 ± 1.0 | 20.1 ± 0.6 | 9.8 ± 1.0 |
| | EV EDCs (n = 12) | 73.9 ± 6.7 | 50.8 ± 4.6 | 23.1 ± 2.3 | 31.3 ± 1.1 | 18.4 ± 0.7 | 8.6 ± 0.9 |
| | Vehicle (n = 14) | 69.5 ± 4.7 | 46.9 ± 3.4 | 22.6 ± 1.4 | 32.8 ± 0.6 | 20.3 ± 0.6 | 8.2 ± 0.6 |
| 4 weeks post-LCA ligation | KCNN4 EDCs (n = 12) | 73.8 ± 3.8 | 42.9 ± 3.1 | 30.9 ± 1.3‡ | 42.7 ± 2.2*,†,‡ | 26.8 ± 1.6†,‡ | 11.2 ± 0.4‡ |
| | NT EDCs (n = 13) | 95.6 ± 8.3 | 60.1 ± 5.6 | 35.5 ± 2.9‡ | 37.6 ± 0.9‡ | 23.4 ± 0.6‡ | 12.4 ± 0.9‡ |
| | EV EDCs (n = 12) | 93.7 ± 8.4 | 59.9 ± 6.1 | 33.7 ± 2.5‡ | 36.6 ± 1.0‡ | 22.4 ± 0.5‡ | 11.9 ± 0.6‡ |
| | Vehicle (n = 14) | 76.0 ± 4.4 | 55.4 ± 3.4 | 20.7 ± 1.2 | 27.3 ± 0.6 | 17.4 ± 0.8 | 7.3 ± 0.5 |

EDV = end diastolic volume,
ESV = end systolic volume,
SV = stroke volume,
FAC = fractional area change,
CO = cardiac output.
*p < 0.05 vs. NT EDCs,
†p < 0.05 vs. EV EDCs,
‡p < 0.05 vs. vehicle.

Mice that received EV or NT EDCs demonstrated similar improvements in echocardiographic (FIG. 4B, Table S2, p<0.05 vs. vehicle) and hemodynamic (FIG. 8C, Table S3) measures of cardiac function 4 weeks after LCA ligation, suggesting that lentiviral transduction per se had no effect on cell-mediated repair of ischemic injury. Animals that received KCNN4 EDCs demonstrated significantly improved cardiac function (FIG. 8B-C, Table S2-3) and smaller scars (FIG. 10A) 4 weeks after LCA ligation as compared to animals that received vehicle or EV/NT EDCs.

TABLE S3

Invasive hemodynamic measures of left ventricular function.

| | SW (mmHg*uL) | CO (uL/min) | SV (uL) | Vmax (uL) | Vmin (uL) | Ves (uL) | Ved (uL) | Pmax (mmHg) |
|---|---|---|---|---|---|---|---|---|
| KCNN4 EDCs (n = 12) | 1144 ± 79‡ | 9472 ± 556 | 16.6 ± 1.0 | 35.6 ± 3.8 | 17.2 ± 3.2 | 19.2 ± 3.3 | 31.5 ± 3.5 | 88.2 ± 2.2 *,†,‡ |
| NT EDCs (n = 13) | 997 ± 76 | 9445 ± 692 | 17.0 ± 1.2 | 35.0 ± 3.9 | 18.0 ± 3.7 | 19.6 ± 3.8 | 32.8 ± 4.0 | 77.8 ± 1.9‡ |
| EV EDCs (n = 12) | 981 ± 113 | 9473 ± 908 | 16.6 ± 1.7 | 34.4 ± 4.1 | 22.3 ± 3.1 | 24.8 ± 3.3 | 37.0 ± 3.6 | 80.7 ± 1.6‡ |
| Vehicle (n = 14) | 713 ± 92 | 8033 ± 1024 | 14.4 ± 1.9 | 36.4 ± 3.5 | 22.1 ± 2.7 | 24.6 ± 2.7 | 33.9 ± 2.9 | 68.0 ± 1.3 |

| | Pmin (mmHg) | Pmean (mmHg) | Pdev (mmHg) | Pes (mmHg) | Ped (mmHg) | HR (bpm) | Ea (mmHg/uL) | dP/dt max (mmHg/s) |
|---|---|---|---|---|---|---|---|---|
| KCNN4 EDCs (n = 12) | 4.0 ± 0.6‡ | 39.2 ± 1.9‡ | 84.2 ± 2.4 *,†,‡ | 82.5 ± 2.6 *,‡ | 9.5 ± 0.9‡ | 557 ± 8 | 5.3 ± 0.3 | 7934 ± 198 *,†,‡ |
| NT EDCs (n = 13) | 2.5 ± 0.6 | 34.3 ± 1.4‡ | 75.4 ± 2.0‡ | 71.3 ± 3.0 | 7.3 ± 0.9 | 557 ± 11 | 4.5 ± 0.3 | 6542 ± 356‡ |
| EV EDCs (n = 12) | 3.8 ± 0.7 | 36.1 ± 2.1‡ | 75.2 ± 1.1‡ | 76.6 ± 1.8‡ | 7.6 ± 1.2 | 575 ± 9 | 5.2 ± 0.4 | 6518 ± 196‡ |
| Vehicle (n = 14) | 1.6 ± 0.3 | 24.8 ± 1.3 | 66.5 ± 1.2 | 65.0 ± 1.2 | 4.0 ± 0.5 | 561 ± 11 | 5.5 ± 0.7 | 5674 ± 166 |

| | dP/dt min (mmHg/s) | dV/dt max (uL/s) | dV/dt min (uL/s) | P@dV/dt max (mmHg) | P@dP/dt max (mmHg) | V@dP/dt max (uL) | V@dP/dt min (uL) |
|---|---|---|---|---|---|---|---|
| KCNN4 EDCs (n = 12) | -6629 ± 282 *,†,‡ | 758 ± 40 | -796 ± 52 | 12.9 ± 3.1 | 54.3 ± 1.7 *,‡ | 32.5 ± 3.9 | 18.0 ± 3.2 |
| NT EDCs (n = 13) | -5437 ± 369 | 766 ± 85 | -893 ± 68 | 12.9 ± 5.3 | 45.1 ± 2.2‡ | 33.1 ± 4.0 | 18.8 ± 3.8 |
| EV EDCs (n = 12) | -5443 ± 144 | 745 ± 64 | -846 ± 95 | 12.7 ± 2.9 | 47.9 ± 2.0‡ | 36.8 ± 3.6 | 23.3 ± 3.2 |
| Vehicle (=14) | -4816 ± 107 | 745 ± 146 | -826 ± 151 | 8.7 ± 3.4 | 36.1 ± 0.8 | 34.1 ± 3.5 | 22.8 ± 2.7 |

| | PVA (mmHg/uL) | PE (mmHg/uL) | CE |
|---|---|---|---|
| KCNN4 EDCs (n = 12) | 2092 ± 213 | 949 ± 183 | 0.8 ± 0.2 |
| NT EDCs (n = 13) | 1980 ± 271 | 789 ± 162 | 0.6 ± 0.1 |
| EV EDCs (n = 12) | 1757 ± 229 | 801 ± 198 | 0.6 ± 0.1 |

TABLE S3-continued

Invasive hemodynamic measures of left ventricular function.

| Vehicle (=14) | 1308 ± 177 | 595 ± 112 | 0.4 ± 0.1 |

SW = stroke work,
CO = cardiac output,
SV = stroke volume,
Vmax = maximum volume,
Vmin = minimum volume,
Ves = end systolic volume,
Ved = end diastolic volume,
Pmax = maximum pressure,
Pmin = minimum pressure,
Pmean = mean pressure,
Pes = end systolic pressure,
Ped = end diastolic pressure,
HR = heart rate,
Ea = arterial elastance,
dP/dtmax = maximum derivative of pressure,
dP/dtmin = minimum derivative of pressure,
dV/dtmax = maximum derivative of volume,
dV/dtmin = minimum derivative of volume,
P@dV/dtmax = pressure at maximum derivative of volume,
P@dP/dtmax = pressure at maximum derivative of pressure,
V@dP/dtmax = volume at maximum derivative of pressure,
V@dP/dtmin = volume at minimum derivative of pressure,
PVA = pressure-volume area,
PE = potential energy,
CE = cardiac events.
*p < 0.05 vs. NT EDCs,
†p < 0.05 vs. EV EDCs,
‡p < 0.05 vs. vehicle.

Figure 11:
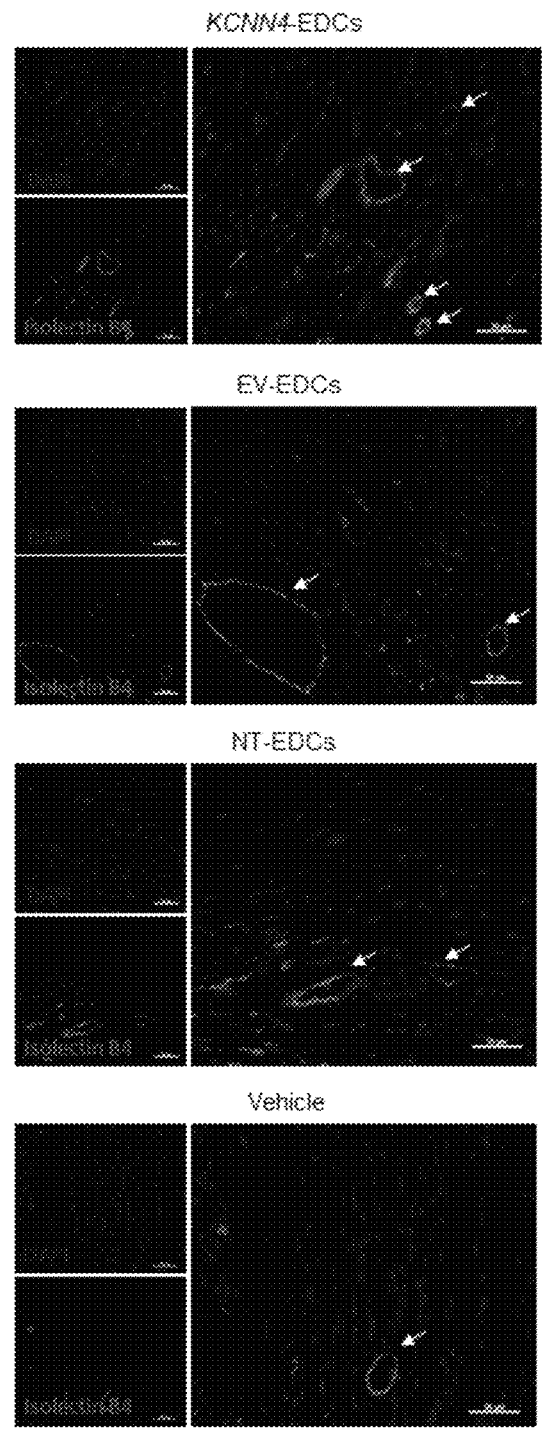
FIG. 11. Are representative images demonstrating vessel density within the peri-infarct region 4 weeks after LCA ligation. Vessels are denoted with a white arrow. Scale Bar 50 μm.
Figure 12A:
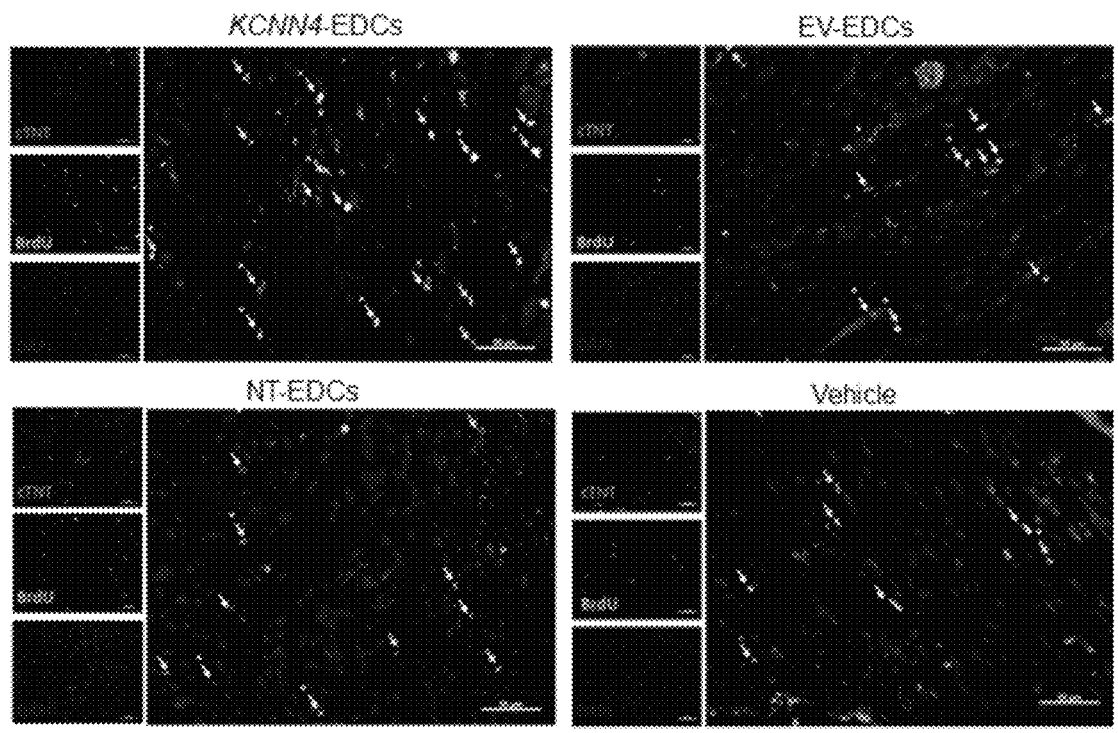
FIGS. 12A-B arerepresentative images demonstrating BrdU$^+$/DAPI$^+$ cells within the peri-infarct region 4 weeks after LCA ligation.
Figure 12B:
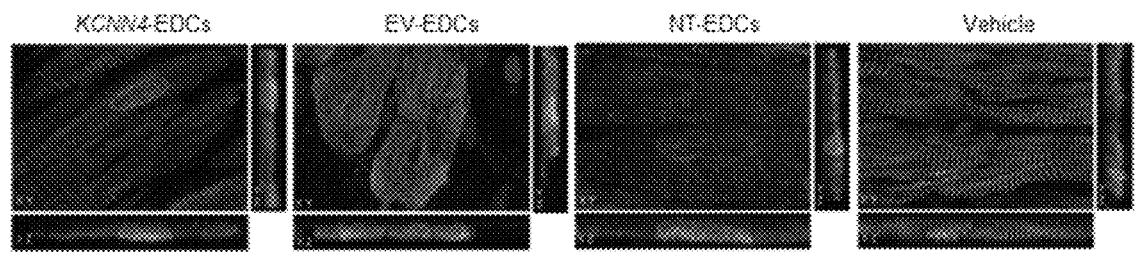

Consistent with the observed increased in vitro proliferation, over-expression of KCNN4 boosted the long-term retention of EDCs by 7±2 fold as compared to intramyocardial injection of NT EDCs (p=0.01; FIG. 10C). Histological analysis revealed that treatment with KCNN4 EDCs increased both infarct wall thickness and the amount of live tissue within the ischemic risk area (FIG. 10B). These salutary changes in cardiac structure were paralleled by increases in new blood-vessel formation (FIG. 10D and FIG. 11) and newly generated cardiomyocytes (FIG. 10E and FIG. 12) within the peri-infarct area. By surface telemetry, transplant of KCNN4 EDCs had no effect on heart rate variability or cardiac conduction (Table S4).

TABLE S4

Effect of KCNN4 over-expression on electrophysiological parameters 21 days after EDC or vehicle injection.

| | RR (ms) | PR (ms) | QRS (ms) | QT (ms) | QTc |
|---|---|---|---|---|---|
| NT EDCs | 174 ± 12 | 56 ± 2 | 31 ± 2 | 90 ± 5 | 217 ± 10 |
| EV EDCs | 157 ± 3 | 51 ± 2 | 24 ± 2 | 82 ± 2 | 208 ± 5 |
| KCNN4 EDCs | 165 ± 3 | 51 ± 3 | 27 ± 2 | 85 ± 2 | 209 ± 6 |
| Vehicle | 168 ± 5 | 47 ± 3 | 30 ± 2 | 94 ± 5 | 228 ± 9 |

Programmed electrical stimulation induced ventricular arrhythmias in a single vehicle treated animal with 2 extra-stimuli (FIG. 13) while all EDC treated animals were non-inducible.

Thus, increasing $I_{KCa3.1}$ within EDCs boosts cell engraftment and stimulation of endogenous repair without increasing susceptibility to malignant ventricular arrhythmias.

Over-Expression of KCNN4 Increases Cytokine and Extracellular Vesicle Secretion by EDCs The cytokine signature of EDCs was profiled using an unbiased proteomic array capable of detecting 102 cytokines within conditioned media after 48 hours of cell culture in 1% oxygen basal media conditions (FIG. 14A). Although KCNN4 over-expression did not significantly increase the number cytokines within conditioned media as compared to EV EDCs (39 vs. 42 cytokines, respectively; Chi square value 0.33, p=0.56 vs. the expected frequency of cytokines elevated), KCNN4 over-expression markedly increased production of cytokines already found within EDC conditioned media (6 vs. 1 cytokine levels increased respectively; Chi square value 3.78, p=0.05 vs. the expected frequency of cytokines elevated; FIG. 14A). Interestingly, amongst the cytokines increased via KCNN4 over-expression, several are implicated in angiogenesis (VEGF (23, 24)(1, 2)), post-infarct healing (angiogenin (25, 26), IGFBP3 (27), SDF-1α (9, 28)) and immune modulation (ICAM-1 (29)) were found. When evaluating the top 10 cytokines secreted by EV or KCNN4 EDCs (FIG. 14B), only minor variations in cytokine levels were noted suggesting that increased $I_{KCa3.1}$ broadens the cytokine signature of EDCs by increasing production of cytokines already produced by EDCs rather than stimulating the increase production of novel cytokines.

Given recent evidence supporting a critical role for extracellular vesicles in the salutary benefits conferred by cardiac-derived cell therapy, the effect of KCNN4 over-expression on extracellular vesicle production was profiled. Media conditioned by KCNN4 EDCs demonstrated a 1.6±0.2 fold increase in nanoparticle content (p<0.05 vs. EV or NT EDCs; FIG. 14C). Nanoparticle size was reflected norms established for therapeutic extracellular vesicles (133±5 nm, p=ns vs. EV or NT EDCs). Consistent with previous transcriptome profiling, the most abundant miRNAs found within adherent cultured EDC extracellular vesicles were associated with cardiomyocyte proliferation (e.g. miR-199a-5p), cardiomyocyte salvage (e.g. miR-125b-5p), protection against oxidative stress (e.g. miR-21-5p) or reduction of cardiac fibrosis (e.g. miR-22-3p) (Table S5).

TABLE S5

Top 10 miRNAs within adherent EDC exosomes involved with cardiomyocyte proliferation, salvage, and modulating cardiac fibrosis.

| Name | Biological role |
|---|---|
| hsa-miR-199a-5p | Promotes cardiomyocyte proliferation |
| hsa-miR-93-5p | Protects against ischemia-reperfusion injury |
| hsa-miR-23a-3p | Promotes cardiomyocyte proliferation |
| hsa-miR-125b-5p | Protects cardiomyocytes against p53 mediated apoptosis |
| hsa-miR-199a-3p + hsa-miR-199b-3p | Promotes cardiomyocyte proliferation |
| hsa-miR-21-5p | Protects cardiomyocyte from oxidative stress |
| hsa-miR-22-3p | Regulates cardiac tissue fibrosis |
| has-miR-495-3p | Promotes cardiomyocyte proliferation |
| hsa-miR-873-3p | Inhibits RIPK1/RIPK3-mediated necrotic cell death in cardiomyocytes |
| hsa-let-7b-5p | Protects transplanted mesenchymal stem cells from apoptosis |

Figure 15A:
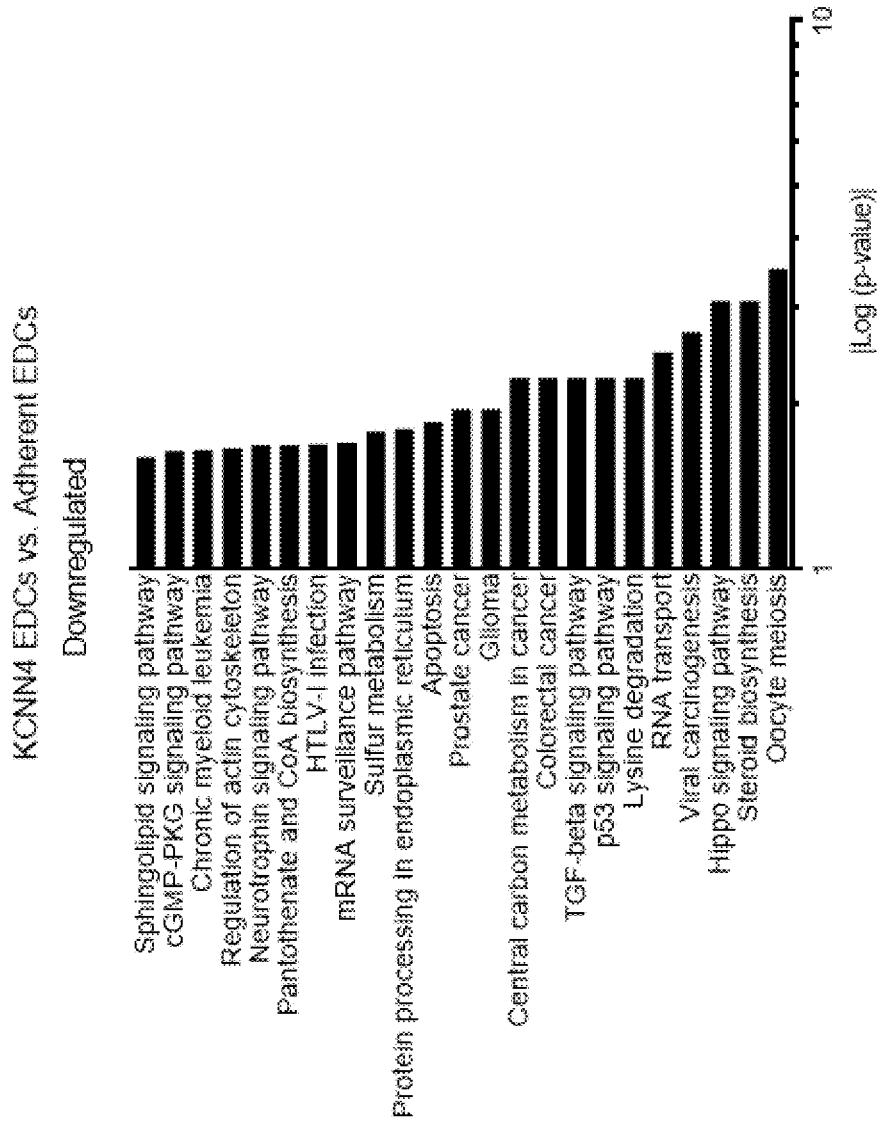
FIG. 15A-C are Kyoto Encyclopedia of Genes and Genomes (KEGG) pathway analysis for KCNN4 over-expression.
Figure 15B:
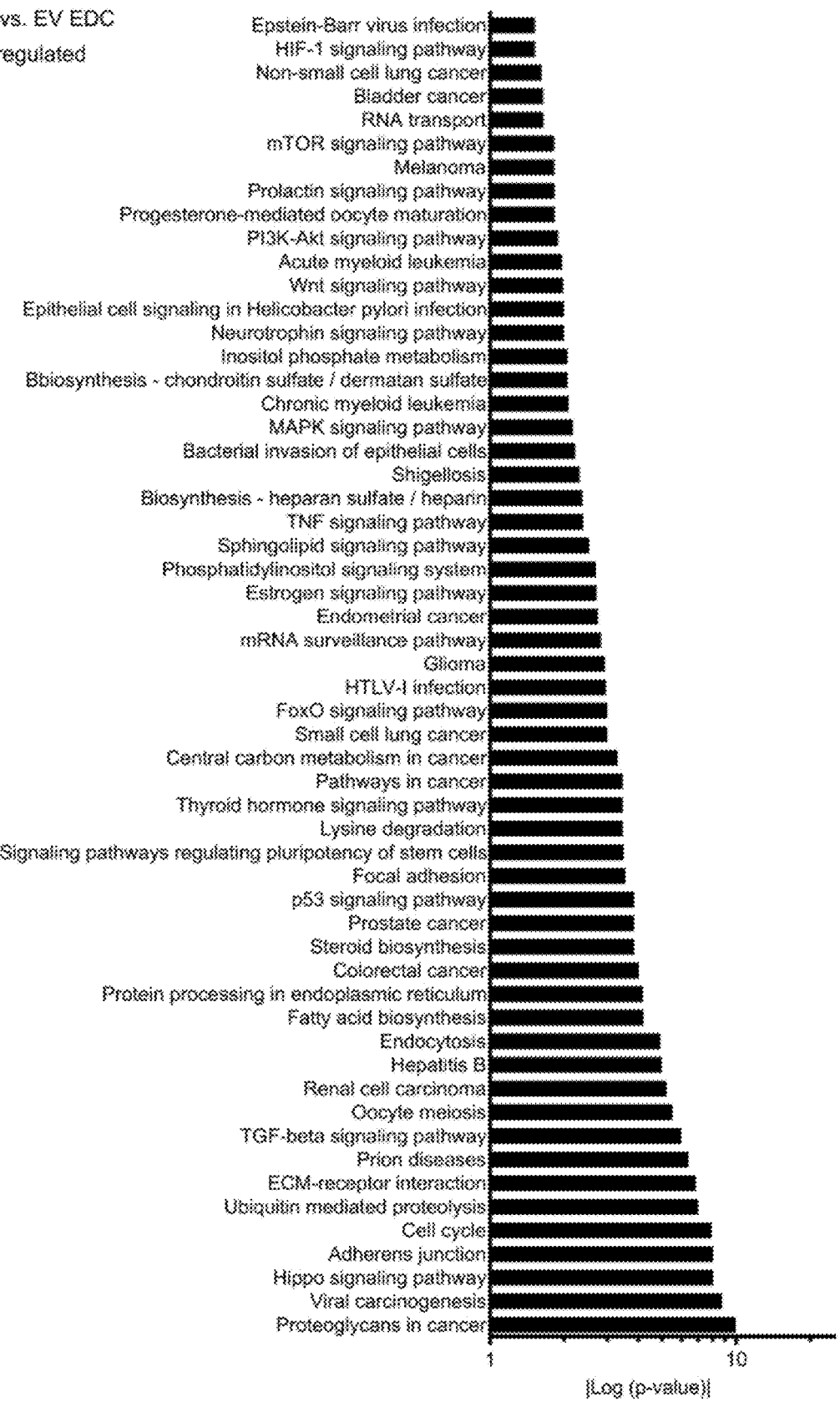
Figure 15C:
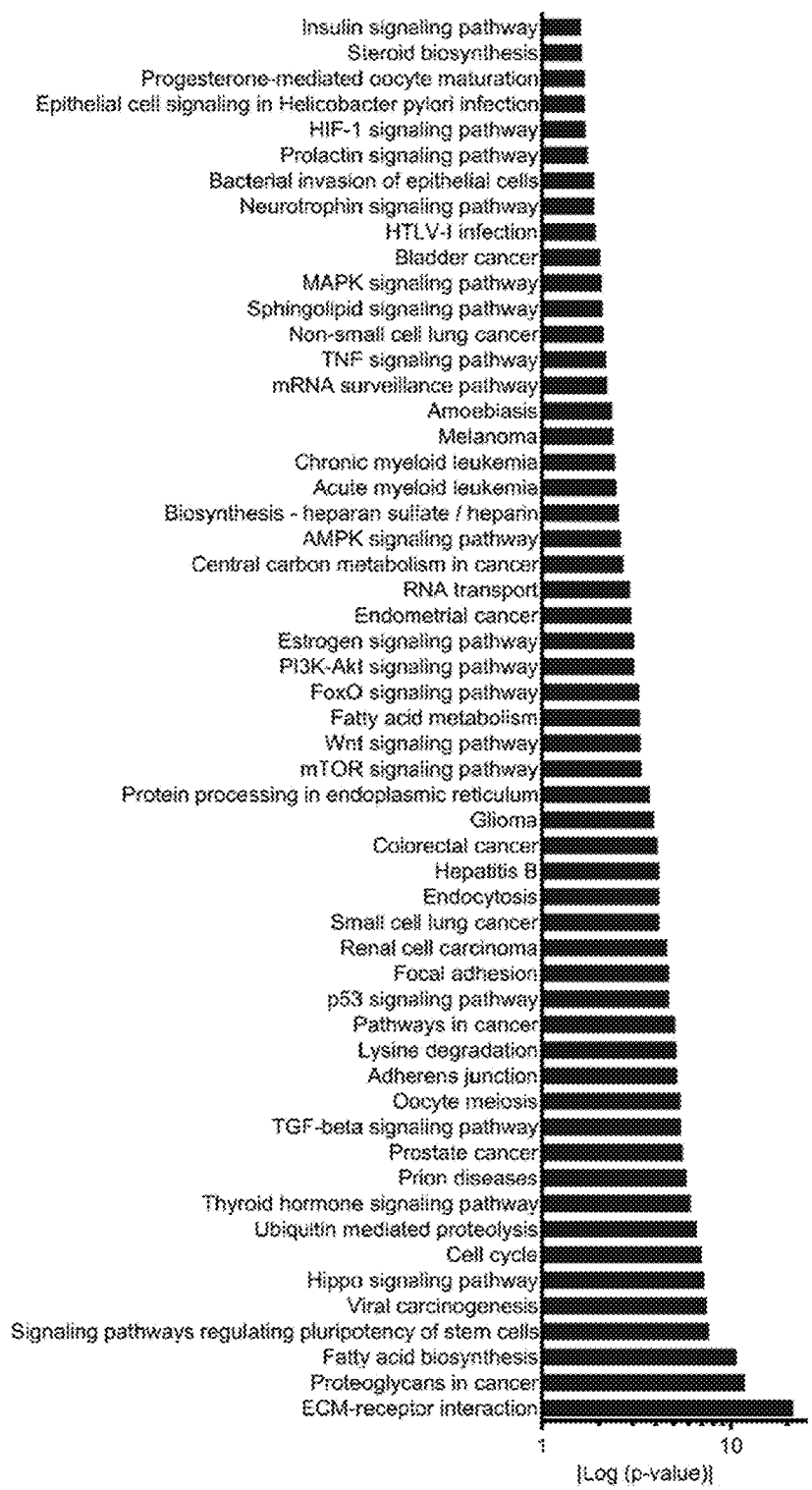

Surprisingly, somatic gene transfer of KCNN4 decreased the expression of only 4 miRNAs (KCNN4 EDCs vs. adherent EDCs, fold change >1.5, p-adjusted <0.05, FIG. 14D, Table S6). These miRNAs typically clustered within TGF-β signaling, Hippo signaling, apoptosis, steroid biosynthesis, RNA transport, protein processing, or cytoskeleton regulation (FIG. 15A). In comparison to lentiviral transduction alone, KCNN4 over-expression rescued 16 miRNAs (fold change >1.5; p-adjusted <0.05, FIG. 14E and Table S7) involved in the signaling pathway regulating pluripotency of stem cells, extra-cellular matrix biosynthesis/interactions, cell cycle, TGF-β signaling, or Hippo signaling pathways (FIG. 15B).

TABLE S6

Comparing miRNA expression in extracellular vesicles secreted from KCNN4 and NT EDCs.

| Name | p-adjusted | P-value | Log2 (Fold change) |
|---|---|---|---|
| Downregulated KCNN4 vs. NT | | | |
| hsa-miR-1246 | 0.001392 | 1.02E−05 | −6.02242 |
| hsa-miR-4531 | 0.004192 | 9.25E−05 | −5.0545 |
| hsa-miR-548n | 0.003996 | 5.88E−05 | −5.26002 |
| hsa-miR-603 | 0.006064 | 0.000178 | −4.76565 |

TABLE S7

Comparing miRNA expression in extracellular vesicles secreted from KCNN4 and NT EDCs.

| Name | p-adjusted | P-value | Log2 (Fold change) |
|---|---|---|---|
| Upregulated KCNN4 vs. EV | | | |
| hsa-let-7a-5p | 7.18E−05 | 5.28E−07 | 7.117411 |
| hsa-miR-100-5p | 0.044937 | 0.003896 | 2.640891 |
| hsa-miR-199b-5p | 0.009134 | 0.000269 | 2.600605 |
| hsa-miR-191-5p | 0.016288 | 0.000637 | 3.028148 |
| hsa-miR-181a-5p | 0.005024 | 0.000111 | 3.033296 |
| hsa-miR-21-5p | 0.040347 | 0.0027 | 2.603005 |
| hsa-miR-22-3p | 0.016288 | 0.000719 | 2.630868 |
| hsa-miR-25-3p | 0.023237 | 0.001196 | 2.517763 |
| hsa-miR-15b-5p | 0.040347 | 0.002967 | 2.307322 |
| hsa-miR-93-5p | 0.047076 | 0.005538 | 2.935141 |
| hsa-miR-99a-5p | 0.036286 | 0.002134 | 2.370586 |
| hsa-miR-15a-5p | 0.044937 | 0.004436 | 2.222103 |
| hsa-miR-29b-3p | 0.044937 | 0.004626 | 2.417488 |
| Downregulated KCNN4 vs. EV | | | |
| hsa-miR-144-3p | 0.044973 | 0.00496 | −3.26627 |
| hsa-miR-182-3p | 0.044937 | 0.003966 | −3.51073 |
| hsa-miR-451a | 0.000382 | 5.61E−06 | −5.79156 |

This data suggests that, akin to effects on cytokines already produced by EDCs, KCNN4 activity increases extracellular vesicle production while only subtlety altering the miRNA expression profile of EDC sourced extracellular vesicles to boost cardiac function after myocardial infarction.

Discussion

As disclosed herein, the therapeutic potential of EDCs is governed by the intermediate-conductance $Ca^{2+}$-activated channel KCa3.1. As was disclosed, while $Ca^{2+}$-activated $K^+$ channels were identified in all EDCs, KCa3.1-channels were exclusively expressed in the CD90⁻ subpopulation that is thought to be responsible for most of the functional benefits associated with cardiac-derived cell therapy (20, 21).

Ion channels provide the basis for generating bioelectric signals that control cell functions (30, 31). Calcium-activated potassium channels are widely distributed in stem cells from different origins (12, 32-37). Functional BKCa channels have been reported to be abundantly expressed in expanded cardiac stem and progenitors cells (37, 38). While BKCa channels have a large conductance, they show strong outward rectification and carry relatively little current in EDCs near the $K^+$ reversal potential, which explains why they do not contribute to EDC resting potential (FIG. 6).

Proliferation and differentiation are tightly controlled by changes in $V_{mem}$, as shown in mesenchymal stem cells (40-43), embryonic stem cells (44), myoblasts (45, 46) and cardiac progenitors (12, 47).

The present inventors have found that the resting membrane potential of EDCs is mainly determined by the intermediate-conductance $Ca^{2+}$-activated channel KCa3.1. This is in contrast to other cardiac derived cells such as cardiomyocytes (48) and fibroblasts (49), where the membrane potential of EDCs is not determined by Kir-channels.

The present inventors have found that KCa3.1-channels control membrane potential of EDCs during SOCE, maintaining the electrical gradient for $Ca^{2+}$ influx. In a variety of cells, $K_{Ca}$ channels are at the crossroad where $Ca^{2+}$ influx, outward ion fluxes and $V_m$ integrate to modulate a large array of cellular functions such as proliferation, migration, differentiation and hormones/cytokines secretion (50). Importantly, $IK_{Ca}$ may be important for cardiogenesis in both embryonic and induced pluripotent stem cells of mice (51-53) and humans (54). Based on these observations, our results point toward KCa3.1 regulation of $V_{mem}$ as a crucial determinant of EDC function.

As disclosed herein, genetic manipulation to enhance KCa3.1-channel expression increased the proliferation and enhanced the paracrine profile of EDCs in vitro.

According to one aspect, there is provided a cardiac explant-derived stem cell (EDC), the cell comprising a gene encoding an intermediate-conductance $Ca^{2+}$-activated $K^+$ channel, and wherein the gene causes an overexpression of the intermediate-conductance $Ca^{2+}$-activated $K^+$ channel. In one aspect, the gene comprises KCNN4 gene and the intermediate-conductance $Ca^{2+}$-activated $K^+$ channel is KCa3.1 channel.

In one aspect, the gene is configured to drive expression of the KCa3.1 channel to hyperpolarize the EDC membrane and enhance $Ca^{2+}$ signalling of the EDC. In one aspect, the gene is configured to drive expression of the KCa3.1 channel to hyperpolarize the EDC membrane and increase intracellular $Ca^{2+}$ concentration ($[Ca^{2+}]_i$) in the EDC. In one aspect, the gene is configured to drive expression of the KCa3.1 channel to increase the paracrine repertoire of the EDC relative to control EDC which do not contain the gene or contain only an empty backbone. In one aspect, the gene is configured to drive expression of the KCa3.1 channel to decrease the resting membrane potential of the cardiac cells and maintain the electrical gradient for $Ca^{2+}$ influx in the EDC relative to control EDC which do not contain the gene or contain only an empty backbone.

In one aspect, the gene is expressed from a vector comprising a promoter operably linked to the gene. In a further aspect, the promoter is a constitutive active promoter. In further aspect, the vector is a lentiviral vector. Lentiviruses are a useful tool for the engineering of adult stem cells because of their transduction efficiency toward slowly proliferating cells, and the absence of detrimental effects on cells (59).

In one aspect, the EDC is CD90$^-$. In one aspect, the EDC was isolated from cultured cardiac explant tissue and then transduced with the gene.

Genetic engineering markedly increased the ability of EDCs to proliferate and ultimately improved the long-term engraftment of transplanted cells. The number of transplanted cells that are ultimately retained 3 weeks after injection is 597±200 vs. 69±22 for KCNN4 vs. NT EDCs, respectively.

In one embodiment, KCNN4 over-expression may have negligible effects on resistance to apoptosis. Without being limited to any particular theory, the marked increase in proliferation affords transplanted cells the ability to escape ongoing attrition after myocardial injection that results from detachment induced cell death (i.e., anoikis) and the toxic post-infarct environment. Thus, KCNN4 over-expression helps to maintain a larger (yet transient) pool of transplanted cells within the myocardium to increase paracrine stimulation of endogenous repair mechanisms.

In some embodiments, benefits conferred by cardiac stem cell therapy occur through paracrine signaling that promotes angiogenesis, cardiomyogenesis, immunomodulation and myocardial salvage. In one embodiment, KCNN4 over-expression favorably broadens the paracrine repertoire of EDCs. Since KCa3.1-mediated elevation of intracellular calcium is necessary for the production of inflammatory chemokines and cytokines by various immune cells (55, 56), it is reasonable to believe, but without limited to any particular theory, that a similar mechanism takes place in EDCs. The marked functional improvement in cardiac function observed after transplant of KCNN4 EDCs is likely mediated by increased cytokine and extracellular vesicles stimulation at the site of injury through a combination of increased cell autonomous effects and increased "cell dose" within the myocardium. In one aspect, the source of cardiac explant tissue can be from the same subject to be treated or can be from another subject, such as for example, donor cardiac explant tissue.

In one aspect, the gene is configured to drive expression of the KCa3.1 channel to increase the production of cytokines relative to control EDC which do not contain the gene or contain only an empty backbone. In a further aspect, the cytokines are VEGF, angiogenin, IGFBP3, SDF-1α, ICAM-1, or combinations thereof.

Compared to non-modified cells, genetically-engineered EDCs were superior in improving cardiac function through a combination of angiogenesis, cardiomyogenesis and myocardial salvage when transplanted into a clinically relevant mouse model mirroring post-infarct healing.

Further disclosed herein is a method for treating or ameliorating a damaged myocardium in a subject, the method comprising: administering a cardiac explant-derived stem cell (EDC) to the damaged myocardium of the subject. In one aspect, before the step of administering, obtaining the EDC by extracting a cardiac explant tissue from the subject, isolating the EDC from the extracted cardiac explant tissue, and introducing the KCNN4 gene to increase the expression of KCa3.1 channels in the EDC. In one aspect, the source of the cardiac explant tissue is from the same subject to be treated or from a donor subject. In one aspect, the EDC increases angiogenesis; increases cytokine production; increases post-infarct healing; promotes immunomodulation; increases cardiomyocyte proliferation and/or salvage; protects against oxidative stress; reduces cardiac fibrosis, increases transplanted-cell engraftment; or any combination thereof. In one aspect, the administering is by injection, and preferably, by intra-myocardial injection. In one aspect, the administering is done about 1 month after a clinical myocardial infarction. In another aspect, the administering is done when the myocardium is scarred and/or remodeled.

Further disclosed herein is a method for producing engineered cardiac explant-derived stem cells (EDCs) having a modulated bioelectric property, the method comprising: obtaining cardiac explant-derived stem cells (EDCs); introducing a KCNN4 gene into the EDCs to increase the expression of KCa3.1 channels, to produce engineered EDCs. In one aspect, the modulated bioelectric property is a hyperpolarized cell membrane and an increased driving force for $Ca^{2+}$-entry. In one aspect, the step of obtaining comprises extracting cardiac explant tissue from a subject and isolating the cardiac explant-derived stem cells (EDCs) from the extracted cardiac explant tissue. In one aspect, the step of isolating comprises digesting the extracted cardiac explant tissue with collagenase, growing the EDCs in cell culture containing cell culture media and oxygen, and harvesting the EDCs from the cell culture. In one aspect, the EDCs are maintained under ischemic conditions, the EDCs demonstrate one or more of: an increase in proliferation; an increase expression of cytokines implicated in angiogenesis, post-infarct healing, immune modulation, or combinations thereof an increase number of extracellular vesicles; and an increase in miRNA associated with cardiomyocyte proliferation, cardiomyocyte salvage, protection against oxidative stress, reducing cardiac fibrosis, increased transplanted-cell engraftment, or combinations thereof. In one aspect, the extracellular vesicles comprise VEGF, angiogenin, IGFBP3, SDF-1α, ICAM-1, or combinations thereof. In one aspect, the extracellular vesicles comprise miR-199a-5p, miR-125b-5p, miR-21-5p, miR-22-3p, or combinations thereof.

Further disclosed herein is a method for treating or ameliorating a damaged myocardium in a subject, the method comprising: introducing a KCNN4 gene into cardiac explant-derived stem cells (EDCs) to increase the expression of KCa3.1 channels, to produce engineered EDCs; culturing the engineered EDCs in conditions sufficient for the engineered EDCs to produce extracellular vesicles; isolating the extracellular vesicles; and administering the extracellular vesicles to the subject to treat or ameliorate the damaged myocardium. In one aspect, the step of isolating comprises collecting the cell culture media containing extracellular vesicles secreted into the cell culture media and then separating the extracellular vesicles from the cell culture media. In one aspect, the step of culturing comprises maintaining the EDCs in conditions mimicking the environment of the ischemic heart. In one aspect, the conditions are one or more of low oxygen and the absence of growth factor supplementation in the cell culture media. In one aspect, the low oxygen is about 1% oxygen. In one aspect, the step of maintaining is around 48 hours. In one aspect, the extracellular vesicles comprise cytokines, preferably, the cytokines are those implicated in angiogenesis, post-infarct healing, immune modulation, or combinations thereof; and miRNA, preferably the miRNA are those associated with cardiomyocyte proliferation, cardiomyocyte salvage, protection against oxidative stress, reducing cardiac fibrosis, increases transplanted-cell engraftment, or combinations thereof. In one aspect, the extracellular vesicles comprise VEGF, angiogenin, IGFBP3, SDF-1α, ICAM-1, or combinations thereof. In one aspect, the extracellular vesicles comprise miR-199a-5p, miR-125b-5p, miR-21-5p, miR-22-3p, or combinations thereof.

In various embodiments, the extracellular vesicles are isolated from the supernatants of the EDCs. This includes, for example, extracellular vesicles secreted into media as conditioned by a population of EDCs in culture.

In several embodiments, the extracellular vesicles secreted by the EDCs and/or in media as conditioned by a population of EDCs in culture contain microRNAs. In various embodiments, these microRNAs can include: miR-199a-5p, miR-125b-5p, miR-21-5p and/or miR-22-3p.

In several embodiments, the extracellular vesicles secreted by a population of EDCs and/or in media as conditioned by a population of EDCs in culture contain VEGF, angiogenin, IGFBP3, SDF-1α, and/or ICAM-1.

In some embodiments, the cardiovascular disease is coronary artery disease, myocardial infarction, ischemic heart disease or heart failure. In one embodiment, the cells are administered via a parenteral route, for example, intravenously, or via direct injection into the heart of the subject.

A further embodiment of the present invention is a pharmaceutical composition comprising a therapeutically effective amount of the isolated stem cells admixed with a pharmaceutically acceptable carrier.

Another embodiment of the present invention comprises a method of treating heart failure or preventing the progression of heart failure in a subject comprising the step of administering to the subject an effective amount of engineered EDCs overexpressing KCa3.1 channels, wherein the amount is effective in at least partially restoring cardiac function. The heart failure may comprise the loss of cardiomyocytes. More specifically, the administration of the engineered EDCs overexpressing KCa3.1 channels at least partially improves tissue salvage and/or function.

Further disclosed herein is a method for manufacturing a medicament for treating or ameliorating a damaged myocardium in a subject, the method comprising: obtaining cardiac explant-derived stem cells (EDCs); introducing a KCNN4 gene into the EDCs to increase the expression of KCa3.1 channels, to produce engineered EDCs, wherein when the engineered EDCs are administered to the damaged myocardium, the engineered EDCs increases angiogenesis; increases cytokine production; increases post-infarct healing; promotes immunomodulation; increases cardiomyocyte proliferation and/or salvage; protects against oxidative stress; reduces cardiac fibrosis, increases transplanted-cell engraftment; or any combination thereof. In one aspect, the step of obtaining comprises extracting cardiac explant tissue from a subject and isolating the EDCs from the extracted cardiac explant tissue. In one aspect, the source of the cardiac explant tissue is from the same subject to be treated or from a donor subject. In one aspect, the step of isolating comprises digesting the extracted cardiac explant tissue with collagenase, growing the EDCs in cell culture containing cell culture media and oxygen, and harvesting the EDCs from the cell culture. In one aspect, the step of harvesting comprises dislodging the EDCs from cultureware. In one aspect, the EDCs are dislodged from the cultureware by using trypsin. Trypsin can include, but is not limited to, TrypLE®.

Further disclosed herein is a composition for treating or ameliorating a damaged myocardium in a subject, the composition comprising extracellular vesicles isolated from cultures of engineered cardiac explant-derived stem cells (EDCs), the engineered EDCs comprising a gene encoding an intermediate-conductance $Ca^{2+}$-activated $K^+$ channel, and wherein the gene causes an overexpression of the intermediate-conductance $Ca^{2+}$-activated $K^+$ channel.

Further disclosed herein is a method for treating or ameliorating a damaged myocardium in a subject, the method comprising: administering a composition comprising extracellular vesicles isolated from cultures of engineered cardiac explant-derived stem cells (EDCs), the engineered cardiac explant-derived stem cells (EDCs) comprising a gene encoding an intermediate-conductance $Ca^{2+}$-activated $K^+$ channel, and wherein the gene causes an overexpression of the intermediate-conductance $Ca^{2+}$-activated $K^+$ channel, wherein the composition increases angiogenesis; increases cytokine production; increases post-infarct healing; promotes immunomodulation; increases cardiomyocyte proliferation and/or salvage; protects against oxidative stress; reduces cardiac fibrosis, increases transplanted-cell engraftment; or any combination thereof. In one aspect, the administering comprises myocardial injection or myocardial infusion. In one aspect, the injection is intramyocardial injection and the myocardial infusion is intra-arterial or intra-venous.

Another embodiment of the present invention comprises a method to treat or ameliorate conditions for which increase in expression of intermediate-conductance $Ca^{2+}$-activated $K^+$ channel is to be effective to treat or ameliorate the conditions in a subject.

In one aspect, the method comprises administering to the subject an effective amount of engineered stem cells overexpressing intermediate-conductance $Ca^{2+}$-activated $K^+$ channel. In one aspect, the effective amount at least partially promotes at least one or more of survival, proliferation, and paracrine stimulation. In one aspect, the method comprises introducing a KCNN4 gene into stem cells to increase the expression of KCa3.1 channels, to produce the engineered stem cells.

In one embodiment, the stem cells are mesenchymal stem cells (MSCs), endothelial cells or adipose stem cells and the engineered mesenchymal stem cells (MSCs), the engineered endothelial cells or the engineered adipose stem cells overexpress KCa3.1 channels.

Another embodiment of the present invention comprises a medicament to treat or ameliorate conditions for which increase in expression of intermediate-conductance $Ca^{2+}$-activated $K^+$ channel is to be effective treat or ameliorate the conditions in a subject, wherein the medicament comprises engineered stem cells overexpressing intermediate-conductance $Ca^{2+}$-activated $K^+$ channel or cellular products produced and/or secreted by the engineered stem cells, or a combination thereof.

Another embodiment of the present invention comprises a method to treat or ameliorate conditions for which the administration of engineered stem cells having increase in expression of intermediate-conductance $Ca^{2+}$-activated $K^+$ channel is indicated.

In some aspects, conditions are cardiovascular diseases (such as angina), peripheral vascular diseases, musculoskeletal diseases (MSK), neurological, and/or hepatic diseases.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown.

REFERENCES

1. G. Savarese, L. H. Lund, Global Public Health Burden of Heart Failure, Card. Fail. Rev. 3, 7-11 (2017).
2. P. K. Nguyen, J.-W. Rhee, J. C. Wu, Adult stem cell therapy and heart failure, 2000 to 2016: a systematic review, JAMA Cardiol. 1, 831-841 (2016).
3. D. R. Davis, E. Kizana, J. Terrovitis, A. S. Barth, Y. Zhang, R. R. Smith, J. Miake, E. Marban, Isolation and expansion of functionally-competent cardiac progenitor cells directly from heart biopsies, J. Mol. Cell. Cardiol. 49, 312-321 (2010).
4. R. Jackson, S. Mount, B. Ye, A. E. Mayfield, V. Chan, M. Boodhwani, R. A. Davies, H. Haddad, D. R. Davis, Isolation of human explant derived cardiac stem cells from cryopreserved heart tissue, PloS One 12, e0176000 (2017).
5. R. Jackson, E. L. Tilokee, N. Latham, S. Mount, G. Rafatian, J. Strydhorst, B. Ye, M. Boodhwani, V. Chan, M. Ruel, T. D. Ruddy, E. J. Suuronen, D. J. Stewart, D. R. Davis, Paracrine Engineering of Human Cardiac Stem Cells With Insulin-Like Growth Factor 1 Enhances Myocardial Repair, J. Am. Heart Assoc. 4, e002104 (2015).
6. A. E. Mayfield, M. E. Fitzpatrick, N. Latham, E. L. Tilokee, M. Villanueva, S. Mount, B.-K. Lam, M. Ruel, D. J. Stewart, D. R. Davis, The impact of patient co-morbidities on the regenerative capacity of cardiac explant-derived stem cells, Stem Cell Res. Ther. 7, 60 (2016).
7. A. E. Mayfield, P. Kanda, A. Nantsios, S. Parent, S. Mount, S. Dixit, B. Ye, R. Seymour, D. J. Stewart, D. R. Davis, Interleukin-6 Mediates Post-Infarct Repair by Cardiac Explant-Derived Stem Cells, Theranostics 7, 4850-4861 (2017).
8. A. E. Mayfield, E. L. Tilokee, N. Latham, B. McNeill, B.-K. Lam, M. Ruel, E. J. Suuronen, D. W. Courtman, D. J. Stewart, D. R. Davis, The effect of encapsulation of cardiac stem cells within matrix-enriched hydrogel capsules on cell survival, post-ischemic cell retention and cardiac function, Biomaterials 35, 133-142 (2014).
9. E. L. Tilokee, N. Latham, R. Jackson, A. E. Mayfield, B. Ye, S. Mount, B.-K. Lam, E. J. Suuronen, M. Ruel, D. J. Stewart, D. R. Davis, Paracrine Engineering of Human Explant-Derived Cardiac Stem Cells to Over-Express Stromal-Cell Derived Factor 1a Enhances Myocardial Repair, Stem Cells Dayt. Ohio 34, 1826-1835 (2016).
10. S. Choi, S. Jung, T. Asahara, W. Suh, S.-M. Kwon, S. Baek, Direct comparison of distinct cardiomyogenic induction methodologies in human cardiac-derived c-kit positive progenitor cells, Tissue Eng. Regen. Med. 9, 311-319 (2012).
11. M. Levin, Molecular bioelectricity: how endogenous voltage potentials control cell behavior and instruct pattern regulation in vivo, Mol. Biol. Cell 25, 3835-3850 (2014).
12. P. Vigneault, P. Naud, X. Y. Qi, J. Xiao, L. Villeneuve, D. R. Davis, S. Nattel, Calcium-dependent potassium channels control proliferation of cardiac progenitor cells and bone marrow-derived mesenchymal stem cells, J. Physiol. In Press, doi:10.1113/JP275388.
13. T.-S. Li, K. Cheng, K. Malliaras, N. Matsushita, B. Sun, L. Marbán, Y. Zhang, E. Marban, Expansion of human cardiac stem cells in physiological oxygen improves cell production efficiency and potency for myocardial repair, Cardiovasc. Res. 89, 157-165 (2011).
14. N. Latham, B. Ye, R. Jackson, B.-K. Lam, D. Kuraitis, M. Ruel, E. J. Suuronen, D. J. Stewart, D. R. Davis, Human blood and cardiac stem cells synergize to enhance cardiac repair when cotransplanted into ischemic myocardium, Circulation 128, S105-112 (2013).
15. D. Burkhoff, I. Mirsky, H. Suga, Assessment of systolic and diastolic ventricular properties via pressure-volume analysis: a guide for clinical, translational, and basic researchers, Am. J. Physiol. Heart Circ. Physiol. 289, H501-512 (2005).
16. J. H. Cho, R. Zhang, P. J. Kilfoil, R. Gallet, G. de Couto, C. Bresee, J. I. Goldhaber, E. Marbán, E. Cingolani, Delayed Repolarization Underlies Ventricular Arrhythmias in Rats With Heart Failure and Preserved Ejection Fraction, Circulation 136, 2037-2050 (2017).
17. X.-L. Tang, G. Rokosh, S. K. Sanganalmath, F. Yuan, H. Sato, J. Mu, S. Dai, C. Li, N. Chen, Y. Peng, B. Dawn, G. Hunt, A. Leri, J. Kajstura, S. Tiwari, G. Shirk, P. Anversa, R. Bolli, Intracoronary administration of cardiac progenitor cells alleviates left ventricular dysfunction in rats with a 30-day-old infarction, Circulation 121, 293-305 (2010).
18. J. R. Munoz, B. R. Stoutenger, A. P. Robinson, J. L. Spees, D. J. Prockop, Human stem/progenitor cells from bone marrow promote neurogenesis of endogenous neural stem cells in the hippocampus of mice, Proc. Natl. Acad. Sci. U. S. A. 102, 18171-18176 (2005).

19. T. E. Robey, M. K. Saiget, H. Reinecke, C. E. Murry, Systems approaches to preventing transplanted cell death in cardiac repair, J Mol Cell Cardio! 45, 567-81 (2008).

20. K. Cheng, A. Ibrahim, M. T. Hensley, D. Shen, B. Sun, R. Middleton, W. Liu, R. R. Smith, E. Marbán, Relative Roles of CD90 and c-Kit to the Regenerative Efficacy of Cardiosphere-Derived Cells in Humans and in a Mouse Model of Myocardial Infarction, J. Am. Heart Assoc. Cardiovasc. Cerebrovasc. Dis. 3 (2014), doi:10.1161/JAHA.114.001260.

21. D. Shen, M. Shen, H. Liang, J. Tang, B. Wang, C. Liu, P. Wang, J. Dong, L. Li, J. Zhang, T. G. Caranasos, Therapeutic benefits of CD90-negative cardiac stromal cells in rats with a 30-day chronic infarct, J. Cell. Mol. Med. 22, 1984-1991 (2018).

22. M. Guéguinou, A. Chantôme, G. Fromont, P. Bougnoux, C. Vandier, M. Potier-Cartereau, KCa and Ca(2+) channels: the complex thought, Biochim. Biophys. Acta 1843, 2322-2333 (2014).

23. J. Wu, F. Zeng, X.-P. Huang, J. C.-Y. Chung, F. Konecny, R. D. Weisel, R.-K. Li, Infarct stabilization and cardiac repair with a VEGF-conjugated, injectable hydrogel, Biomaterials 32, 579-586 (2011).

24. R. Matsumoto, T. Omura, M. Yoshiyama, T. Hayashi, S. Inamoto, K.-R. Koh, K. Ohta, Y. Izumi, Y. Nakamura, K. Akioka, Y. Kitaura, K. Takeuchi, J. Yoshikawa, Vascular endothelial growth factor-expressing mesenchymal stem cell transplantation for the treatment of acute myocardial infarction, Arterioscler. Thromb. Vasc. Biol. 25, 1168-1173 (2005).

25. H. Reich, E. Tseliou, G. de Couto, J. Angert, J. Valle, Y. Kubota, D. Luthringer, J. Mirocha, B. Sun, R. R. Smith, L. Marbán, E. Marbán, Repeated transplantation of allogeneic cardiosphere-derived cells boosts therapeutic benefits without immune sensitization in a rat model of myocardial infarction, J. Heart Lung Transplant. Off. Publ. Int. Soc. Heart Transplant. 35, 1348-1357 (2016).

26. L. Grigorian-Shamagian, W. Liu, S. Fereydooni, R. C. Middleton, J. Valle, J. H. Cho, E. Marbán, Cardiac and systemic rejuvenation after cardiosphere-derived cell therapy in senescent rats, Eur. Heart J. 38, 2957-2967 (2017).

27. Q. Xiang, Y. Liao, H. Chao, W. Huang, J. Liu, H. Chen, D. Hong, Z. Zou, A. P. Xiang, W. Li, ISL1 overexpression enhances the survival of transplanted human mesenchymal stem cells in a murine myocardial infarction model, Stem Cell Res. Ther. 9, 51 (2018).

28. K. Cheng, K. Malliaras, R. R. Smith, D. Shen, B. Sun, A. Blusztajn, Y. Xie, A. Ibrahim, M. A. Aminzadeh, W. Liu, T.-S. Li, M. A. De Robertis, L. Marbán, L. S. C. Czer, A. Trento, E. Marban, Human cardiosphere-derived cells from advanced heart failure patients exhibit augmented functional potency in myocardial repair, JACC Heart Fail. 2, 49-61 (2014).

29. A. M. Salvador, T. Nevers, F. Velázquez, M. Aronovitz, B. Wang, A. Abadia Molina, I. Z. Jaffe, R. H. Karas, R. M. Blanton, P. Alcaide, Intercellular Adhesion Molecule 1 Regulates Left Ventricular Leukocyte Infiltration, Cardiac Remodeling, and Function in Pressure Overload-Induced Heart Failure, J. Am. Heart Assoc. 5, e003126 (2016).

30. D. J. Blackiston, K. A. McLaughlin, M. Levin, Bioelectric controls of cell proliferation: ion channels, membrane voltage and the cell cycle, Cell Cycle 8, 3519-28 (2009).

31. S. Sundelacruz, M. Levin, D. L. Kaplan, Role of membrane potential in the regulation of cell proliferation and differentiation, Stem Cell Rev 5, 231-46 (2009).

32. S. Liebau, B. Vaida, C. Proepper, S. Grissmer, A. Storch, T. M. Boeckers, P. Dietl, O. H. Wittekindt, Formation of cellular projections in neural progenitor cells depends on SK3 channel activity, J. Neurochem. 101, 1338-1350 (2007).

33. K. Wang, T. Xue, S. Y. Tsang, R. Van Huizen, C. W. Wong, K. W. Lai, Z. Ye, L. Cheng, K. W. Au, J. Zhang, G. R. Li, C. P. Lau, H. F. Tse, R. A. Li, Electrophysiological properties of pluripotent human and mouse embryonic stem cells, Stem Cells 23, 1526-34 (2005).

34. B. Subramani, S. Subbannagounder, S. Palanivel, C. Ramanathanpullai, S. Sivalingam, A. Yakub, M. SadanandaRao, A. Seenichamy, A. K. Pandurangan, J. J. Tan, R. Ramasamy, Generation and characterization of human cardiac resident and non-resident mesenchymal stem cell, Cytotechnology 68, 2061-2073 (2016).

35. X. Bai, J. Ma, Z. Pan, Y. H. Song, S. Freyberg, Y. Yan, D. Vykoukal, E. Alt, Electrophysiological properties of human adipose tissue-derived stem cells, Am J Physiol Cell Physiol 293, C1539-50 (2007).

36. R. Tao, C. P. Lau, H. F. Tse, G. R. Li, Functional ion channels in mouse bone marrow mesenchymal stem cells, Am J Physiol Cell Physiol 293, C1561-7 (2007).

37. Y.-Y. Zhang, G. Li, H. Che, H.-Y. Sun, X. Li, W.-K. Au, G.-S. Xiao, Y. Wang, G.-R. Li, Characterization of functional ion channels in human cardiac c-kit+ progenitor cells, Basic Res. Cardiol. 109, 407 (2014).

38. O. Ayad, C. Magaud, S. Sebille, J. Bescond, C. Mimbimi, C. Cognard, J.-F. Faivre, P. Bois, A. Chatelier, Functional BKCa channel in human resident cardiac stem cells expressing W8B2, FEBS J. 285, 518-530 (2018).

39. F. Angelini, V. Ionta, F. Rossi, F. Miraldi, E. Messina, A. Giacomello, Foetal bovine serum-derived exosomes affect yield and phenotype of human cardiac progenitor cell culture, BioImpacts BI 6, 15-24 (2016).

40. S. Sundelacruz, M. Levin, D. L. Kaplan, Membrane potential controls adipogenic and osteogenic differentiation of mesenchymal stem cells, PLoS One 3, e3737 (2008).

41. S. Sundelacruz, M. Levin, D. L. Kaplan, Depolarization alters phenotype, maintains plasticity of predifferentiated mesenchymal stem cells, Tissue Eng. Part A 19, 1889-1908 (2013).

42. M. You, M. S. Song, S. K. Lee, P. D. Ryu, S. Y. Lee, D. Kim, Voltage-gated K+ channels in adipogenic differentiation of bone marrow-derived human mesenchymal stem cells, Acta Pharmacol. Sin. 34, 129-136 (2013).

43. A. Diehlmann, S. Bork, R. Saffrich, R. W. Veh, W. Wagner, C. Derst, KATP channels in mesenchymal stromal stem cells: strong up-regulation of Kir6.2 subunits upon osteogenic differentiation, Tissue Cell 43, 331-6 (2011).

44. S.-Y. Ng, C.-H. Chin, Y.-T. Lau, J. Luo, C.-K. Wong, Z.-X. Bian, S.-Y. Tsang, Role of voltage-gated potassium channels in the fate determination of embryonic stem cells, J. Cell. Physiol. 224, 165-177 (2010).

45. V. Hinard, D. Belin, S. Konig, C. R. Bader, L. Bernheim, Initiation of human myoblast differentiation via dephosphorylation of Kir2.1 K+ channels at tyrosine 242, Dev. Camb. Engl. 135, 859-867 (2008).

46. S. Konig, V. Hinard, S. Arnaudeau, N. Holzer, G. Potter, C. R. Bader, L. Bernheim, Membrane hyperpolarization triggers myogenin and myocyte enhancer factor-2 expression during human myoblast differentiation, J. Biol. Chem. 279, 28187-28196 (2004).
47. P. van Vliet, T. P. de Boer, M. A. van der Heyden, M. K. El Tamer, J. P. Sluijter, P. A. Doevendans, M. J. Goumans, Hyperpolarization induces differentiation in human cardiomyocyte progenitor cells, Stem Cell Rev 6, 178-85 (2010).
48. L. Chilton, S. Ohya, D. Freed, E. George, V. Drobic, Y. Shibukawa, K. A. Maccannell, Y. Imaizumi, R. B. Clark, I. M. C. Dixon, W. R. Giles, K+ currents regulate the resting membrane potential, proliferation, and contractile responses in ventricular fibroblasts and myofibroblasts, Am. J. Physiol. Heart Circ. Physiol. 288, H2931-2939 (2005).
49. X.-Y. Qi, H. Huang, B. Ordog, X. Luo, P. Naud, Y. Sun, C.-T. Wu, K. Dawson, A. Tadevosyan, Y. Chen, M. Harada, D. Dobrev, S. Nattel, Fibroblast inward-rectifier potassium current upregulation in profibrillatory atrial remodeling, Circ. Res. 116, 836-845 (2015).
50. H. Berkefeld, B. Fakler, U. Schulte, Ca2+-activated K+ channels: from protein complexes to function, Physiol. Rev. 90, 1437-1459 (2010).
51. A. Kleger, S. Liebau, Calcium-activated potassium channels, cardiogenesis of pluripotent stem cells, and enrichment of pacemaker-like cells, Trends Cardiovasc. Med. 21, 74-83 (2011).
52. S. Liebau, M. Tischendorf, D. Ansorge, L. Linta, M. Stockmann, C. Weidgang, M. Iacovino, T. Boeckers, G. von Wichert, M. Kyba, A. Kleger, An Inducible Expression System of the Calcium-Activated Potassium Channel 4 to Study the Differential Impact on Embryonic Stem Cells, Stem Cells Int. 2011, 1-12 (2011).
53. A. Kleger, T. Seufferlein, D. Malan, M. Tischendorf, A. Storch, A. Wolheim, S. Latz, S. Protze, M. Porzner, C. Proepper, C. Brunner, S.-F. Katz, G. Varma Pusapati, L. Bullinger, W.-M. Franz, R. Koehntop, K. Giehl, A. Spyrantis, O. Wittekindt, Q. Lin, Q. Lin, M. Zenke, B. K. Fleischmann, M. Wartenberg, A. M. Wobus, T. M. Boeckers, S. Liebau, Modulation of calcium-activated potassium channels induces cardiogenesis of pluripotent stem cells and enrichment of pacemaker-like cells, Circulation 122, 1823-1836 (2010).
54. M. Muller, M. Stockmann, D. Malan, A. Wolheim, M. Tischendorf, L. Linta, S.-F. Katz, Q. Lin, S. Latz, C. Brunner, A. M. Wobus, M. Zenke, M. Wartenberg, T. M. Boeckers, G. von Wichert, B. K. Fleischmann, S. Liebau, A. Kleger, Ca2+ activated K channels-new tools to induce cardiac commitment from pluripotent stem cells in mice and men, Stem Cell Rev. 8, 720-740 (2012).
55. S. Ghanshani, H. Wulff, M. J. Miller, H. Rohm, A. Neben, G. A. Gutman, M. D. Cahalan, K. G. Chandy, Up-regulation of the IKCa1 potassium channel during T-cell activation. Molecular mechanism and functional consequences, J. Biol. Chem. 275, 37137-37149 (2000).
56. S. Mark Duffy, P. Berger, G. Cruse, W. Yang, S. J. Bolton, P. Bradding, The K+ channel iKCA1 potentiates Ca2+ influx and degranulation in human lung mast cells, J. Allergy Clin. Immunol. 114, 66-72 (2004).
57. S. P. Yu, Z. Wei, L. Wei, Preconditioning strategy in stem cell transplantation therapy, Transl Stroke Res 4, 76-88 (2013).
58. K. A. McLaughlin, M. Levin, Bioelectric signaling in regeneration: Mechanisms of ionic controls of growth and form, Dev. Biol. 433, 177-189 (2018).
59. L. McGinley, J. McMahon, P. Strappe, F. Barry, M. Murphy, D. O'Toole, T. O'Brien, Lentiviral vector mediated modification of mesenchymal stem cells & enhanced survival in an in vitro model of ischaemia, Stem Cell Res. Ther. 2, 12 (2011).

What is claimed is:

1. An adult cardiac explant-derived stem cell (EDC), the adult cardiac explant-derived stem cell comprising a gene encoding an intermediate-conductance $Ca^{2+}$-activated K+ channel or functional fragment thereof, and wherein the gene causes an overexpression of the intermediate-conductance $Ca^{2+}$-activated $K^+$ channel or functional fragment thereof, wherein the adult cardiac explant-derived stem cell is $CD90^-$.

2. The adult cardiac explant-derived stem cell of claim 1, wherein the gene comprises KCNN4 gene or functional fragment thereof and the intermediate-conductance $Ca^{2+}$-activated $K^+$ channel is KCa3.1 channel or functional fragment thereof.

3. The adult cardiac explant-derived stem cell of claim 2, wherein the gene is configured to drive expression of the KCa3.1 channel: to hyperpolarize an adult cardiac explant-derived stem cell membrane and enhance $Ca^{2+}$ signaling of the adult cardiac explant-derived stem cell; to hyperpolarize an adult cardiac explant-derived stem cell membrane and increase intracellular $Ca^{2+}$ concentration ($[Ca^{2+}]i$) in the adult; to increase a paracrine repertoire of the adult cardiac explant-derived stem cell relative to control adult cardiac explant-derived stem cell which do not contain the gene or contain only an empty backbone; to decrease a resting membrane potential of the adult cardiac explant-derived stem cell and maintain an electrical gradient for $Ca^{2+}$ influx in the adult cardiac explant-derived stem cell relative to control adult cardiac explant-derived stem cell which do not contain the gene or contain only an empty backbone; to increase miRNA associated with cardiomyocyte proliferation, cardiomyocyte salvage, protection against oxidative stress, reduction of cardiac fibrosis, or increased transplanted-cell engraftment, or combinations thereof relative to control adult cardiac explant-derived stem cell which do not contain the gene or contain only an empty backbone; to increase number of extracellular vesicles relative to control adult cardiac explant-derived stem cell which do not contain the gene or contain only an empty backbone; and/or to increase the production of cytokines relative to control adult cardiac explant-derived stem cell which do not contain the gene or contain only an empty backbone.

4. The adult cardiac explant-derived stem cell of claim 3, wherein the cytokines are VEGF, angiogenin, IGFBP3, SDF-1α, or ICAM-1, or combinations thereof.

5. A method for treating or ameliorating a damaged myocardium in a subject, the method comprising the step of:
administering an adult cardiac explant-derived stem cell (EDC) of claim 1 to the damaged myocardium of the subject.

6. A method of producing the adult cardiac explant-derived stem cells of claim 1 having a modulated bioelectric property, the method comprising the steps of:
obtaining an adult cardiac explant-derived stem cell (EDC);
introducing a gene encoding an intermediate-conductance $Ca^{2+}$-activated $K^+$ channel or functional fragment thereof into the EDC to increase an expression of the intermediate-conductance $Ca^{2+}$-activated $K^+$ channel or functional fragment thereof; and
selecting a transfected EDC for CD90.

7. The method of claim 6, wherein the gene comprises KCNN4 gene and the intermediate-conductance $Ca^{2+}$-activated $K^+$ channel is KCa3.1 channel.

8. The method of claim 6, wherein when the adult cardiac explant-derived stem cell is maintained under ischemic conditions, the EDC& demonstrate one or more of: an increase in proliferation; an increase expression of cytokines implicated in angiogenesis, post-infarct healing, or immune modulation, or combinations thereof; an increase number of extracellular vesicles; and an increase in miRNA associated with cardiomyocyte proliferation, cardiomyocyte salvage, protection against oxidative stress, reduction of cardiac fibrosis, or increased transplanted-cell engraftment, or combinations thereof.

9. The method of claim 8, wherein the extracellular vesicles comprise VEGF, angiogenin, IGFBP3, SDF-1α, or ICAM-1, or combinations thereof; and/or the extracellular vesicles comprise miR-199a-5p, miR-125b-5p, miR-21-5p, or miR-22-3p, or combinations thereof.

10. A method for producing extracellular vesicles to treat or ameliorate a damaged myocardium in a subject, the method comprising the steps of:
culturing the adult cardiac explant-derived stem cell of claim 1 in conditions sufficient for the adult cardiac explant-derived stem cell to produce extracellular vesicles; and isolating the extracellular vesicles.

11. The method of claim 10, wherein the gene comprises KCNN4 gene or functional fragment thereof and the intermediate-conductance $Ca^{2+}$-activated $K^+$ channel is KCa3.1 channel or functional fragment thereof.

12. The method of claim 10, wherein the step of culturing comprises maintaining the adult cardiac explant-derived stem cell in conditions mimicking an environment of an ischemic heart.

13. The method of claim 10, wherein the conditions are one or more of low oxygen and an absence of growth factor supplementation in a cell culture media.

14. The method of claim 10, wherein the extracellular vesicles comprise cytokines, preferably, the cytokines are those implicated in angiogenesis, post-infarct healing, or immune modulation, or combinations thereof; and miRNA, preferably the miRNA are those associated with cardiomyocyte proliferation, cardiomyocyte salvage, protection against oxidative stress, reduction of cardiac fibrosis, or increased transplanted-cell engraftment, or combinations thereof.

15. The method of claim 10, wherein the extracellular vesicles comprise VEGF, angiogenin, IGFBP3, SDF-1α, or ICAM-1, or combinations thereof; and/or the extracellular vesicles comprise miR-199a-5p, miR-125b-5p, miR-21-5p, or miR-22-3p, or combinations thereof.

16. A medicament for treating or ameliorating a damaged myocardium in a subject, the medicament comprising: extracellular vesicles produced according to the method of claim 10; the adult cardiac explant-derived stem cell produced according to the method of claim 6; or a cell culture media obtained after the culturing of the adult cardiac explant-derived stem cell produced according to the method of claim 10.

17. A method for treating or ameliorating a damaged myocardium in a subject comprising the step of administering the medicament of claim 16 to a subject in need thereof.

18. The adult cardiac explant-derived stem cell of claim 1, wherein the adult cardiac explant-derived stem cell is a human cell.

19. The adult cardiac explant-derived stem cell of claim 3, wherein the extracellular vesicles comprise VEGF, angiogenin, IGFBP3, SDF-1α, or ICAM-1, or combinations thereof; and/or the extracellular vesicles comprise miR-199a-5p, miR-125b-5p, miR-21-5p, or miR-22-3p, or combinations thereof.

\* \* \* \* \*